(12) United States Patent
Barmes et al.

(10) Patent No.: US 11,389,253 B2
(45) Date of Patent: Jul. 19, 2022

(54) LASER-BASED IMPLANT ALIGNMENT AND RESECTION GUIDE SYSTEMS AND RELATED METHODS

(71) Applicant: Paragon 28, Inc., Englewood, CO (US)

(72) Inventors: Francis D. Barmes, Parker, CO (US); Daniel J. Lee, Englewood, CO (US); Leonard Daniel Latt, Tucson, AZ (US); Randy Allard, Golden, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 17/084,155

(22) Filed: Oct. 29, 2020

(65) Prior Publication Data

US 2021/0059769 A1 Mar. 4, 2021

Related U.S. Application Data

(63) Continuation of application No. PCT/US2019/029978, filed on Apr. 30, 2019.
(Continued)

(51) Int. Cl.
*A61B 17/58* (2006.01)
*A61B 17/60* (2006.01)
(Continued)

(52) U.S. Cl.
CPC .......... *A61B 34/20* (2016.02); *A61B 17/1707* (2013.01); *A61B 17/1764* (2013.01);
(Continued)

(58) Field of Classification Search
CPC combination set(s) only.
See application file for complete search history.

(56) References Cited

U.S. PATENT DOCUMENTS

| 7,468,075 B2 | 12/2008 | Lang |
| 7,534,263 B2 | 5/2009 | Burdulis, Jr. |

(Continued)

FOREIGN PATENT DOCUMENTS

| WO | 2010122034 A1 | 10/2010 |
| WO | 2019/213122 A1 | 11/2019 |
| WO | 2020123899 A1 | 6/2020 |

OTHER PUBLICATIONS

International Search Report and Written Opinion of the International Searching Authority for International Application No. PCT/US2019/029978 dated Jul. 8, 2019.

(Continued)

*Primary Examiner* — Sameh R Boles
(74) *Attorney, Agent, or Firm* — Heslin Rothenberg Farley & Mesiti P.C.

(57) ABSTRACT

Laser-based implant guide systems and methods that align an implant with an axis of an anatomical structure of interest are disclosed. The systems include a target base configured to couple to a patient in alignment with the axis, and a target member configured to couple to the target base that includes a visual indication of the location of the axis. The systems further include an implant guide that includes a laser device and a resection guide. The implant guide is configured to adjust at least one of the position and the orientation of the laser device with respect to the anatomical structure of interest such that a laser line projecting from the laser device is aligned with the visual indication of the target member, and the resection guide facilities implantation of the implant in a resected portion of the anatomical structure of interest in alignment with the axis.

23 Claims, 36 Drawing Sheets

Related U.S. Application Data

(60) Provisional application No. 62/664,663, filed on Apr. 30, 2018.

(51) Int. Cl.
*A61F 2/00* (2006.01)
*A61B 34/20* (2016.01)
*A61B 90/00* (2016.01)
*A61B 17/17* (2006.01)

(52) U.S. Cl.
CPC .......... *A61B 17/1775* (2016.11); *A61B 90/39* (2016.02); *A61B 2034/2068* (2016.02); *A61B 2090/3983* (2016.02)

(56) References Cited

U.S. PATENT DOCUMENTS

| | | |
|---|---|---|
| 7,618,451 B2 | 11/2009 | Berez |
| 7,981,158 B2 | 7/2011 | Fitz |
| 8,062,302 B2 | 11/2011 | Lang |
| 8,083,745 B2 | 12/2011 | Lang |
| 8,105,330 B2 | 1/2012 | Fitz |
| 8,357,166 B2 | 1/2013 | Aram |
| 8,366,771 B2 | 2/2013 | Burdulis, Jr. |
| 8,460,304 B2 | 6/2013 | Fitz |
| 8,585,708 B2 | 11/2013 | Fitz |
| 8,617,172 B2 | 12/2013 | Fitz |
| 8,657,827 B2 | 2/2014 | Fitz |
| 8,951,259 B2 | 2/2015 | Fitz et al. |
| 8,951,260 B2 | 2/2015 | Lang |
| 8,965,088 B2 | 2/2015 | Tsougarakis et al. |
| 9,023,050 B2 | 5/2015 | Lang |
| 9,066,728 B2 | 6/2015 | Burdulis, Jr. |
| 9,072,531 B2 | 7/2015 | Fitz et al. |
| 9,107,680 B2 | 8/2015 | Fitz et al. |
| 9,125,672 B2 | 9/2015 | Fitz et al. |
| 9,125,673 B2 | 9/2015 | Fitz et al. |
| 9,186,161 B2 | 11/2015 | Lang |
| 9,220,517 B2 | 12/2015 | Lang |
| 9,326,780 B2 | 5/2016 | Wong et al. |
| 9,358,018 B2 | 6/2016 | Fitz |
| 2005/0070897 A1 | 3/2005 | Petersen |
| 2007/0043375 A1 | 2/2007 | Anissian |
| 2007/0073296 A1 | 3/2007 | Panchbhavi |
| 2008/0015599 A1 | 1/2008 | D'Alessio et al. |
| 2008/0269757 A1 | 10/2008 | McMinn |
| 2009/0234360 A1 | 9/2009 | Alexander |
| 2010/0217338 A1 | 8/2010 | Carroll |
| 2010/0331848 A1 | 12/2010 | Smith et al. |
| 2011/0218542 A1 | 9/2011 | Lian |
| 2012/0277745 A1 | 11/2012 | Lizee |
| 2013/0060253 A1 | 3/2013 | Couture et al. |
| 2014/0025127 A1 | 1/2014 | Richter et al. |
| 2014/0236157 A1 | 8/2014 | Tochigi et al. |
| 2015/0157339 A1 | 6/2015 | McGinley et al. |
| 2015/0305753 A1 | 10/2015 | McGinley et al. |
| 2017/0112586 A1 | 4/2017 | Dhupar |
| 2017/0238946 A1 * | 8/2017 | van der Walt ......... A61B 34/25 |
| 2017/0354425 A1 | 12/2017 | Zaima |
| 2018/0221074 A1 | 8/2018 | Dacosta et al. |
| 2018/0280069 A1 | 10/2018 | Barmes et al. |

OTHER PUBLICATIONS

Wright Medical Technology, Inc., Prophecy Infinity Preoperative Navigation Guides, Surgical Technique, https://www.wightemedia.com/ProductFiles/Files/PDFs/011940_EN_LR_LE.pdf, 39 pages, Feb. 8, 2018 (retrieved from the Internet on Mar. 16, 2020).

International Search Report and Written Opinion of the International Searching Authority for PCT/US2019/066336, dated Apr. 1, 2020, 17 pages.

Extended European Search Report issued in European Patent Application No. 19796024.8, dated Dec. 13, 2021, 10 pages.

International Search Report and Written Opinion for international patent application No. PCT/US2019/066149 (published as WO 2020/123899), 12 pages, dated Apr. 14, 2020.

International Preliminary Report on Patentability for International Application No. PCT/US2019/029978, dated Nov. 3, 2020, 9 pages, International Bureau of WIPO.

* cited by examiner

LASER-BASED IMPLANT ALIGNMENT AND RESECTION GUIDE SYSTEMS AND RELATED METHODS

CROSS REFERENCE TO RELATED APPLICATION

This application is a continuation of PCT/US2019/029978 filed on Apr. 30, 2019 and entitled Laser-Based Implant Alignment And Resection Guide Systems And Related Methods, which claims priority benefit under 35 U.S.C. § 119(e) to U.S. provisional application No. 62/664,663 filed on Apr. 30, 2018 and entitled Laser-Based Implant Alignment Systems And Methods, which are incorporated herein by reference in their entireties.

FIELD OF DISCLOSURE

The present disclosure is generally directed to laser alignment or guidance systems and methods for the implantation of implants. More particularly, the present disclosure is directed to laser alignment or guidance systems and methods that facilitate the alignment of an implant with the mechanical axis of an extremity of a patient.

BACKGROUND

Typically, implant alignment or guide systems invasively attach to a patient, such as to one or more bones of an extremity of the patient. For example, in an ankle joint replacement system or surgery, an alignment guide is typically attached to the patient's foot and along the length of the tibia bone (e.g., via pins, k-wire or other removable mechanical fasteners). Typical alignment guides thereby necessitate one or more incisions that result in post-operative pain and/or sites for infection. Still further, many current alignment systems physically extend along one or more associated bones of the patient, and thereby introduce inaccuracy. For example, alignment systems that physically extend along one or more associated bones of a patient tend to shift or otherwise become misaligned during installation and/use (e.g., due to the weight of their numerous physical components).

Many current implant alignment or guide systems attempt to align an axis of a respective implant with the anatomical axis of one or more associated bones. For example, in an ankle joint replacement system or surgery, a typical alignment guide is configured to attempt to align an axis of an implant with the anatomical axis of the patient's tibia bone. However, the Applicant has recognized that such an anatomical alignment may cause pain, injury, deformity of one or more anatomical structure of the foot and/or ankle, and, as a result, may diminish the quality of life of the patient.

Therefore, non-invasive or minimally invasive implant alignment or guide systems and methods are desirable. Implant alignment or guide systems and methods that are stable and do not tend to shift or otherwise become misaligned are also desirable. Still further, implant alignment or guide systems and methods that properly align an associated implant with the anatomical construct of a patient are also desirable.

While certain aspects of conventional technologies have been discussed to facilitate disclosure, Applicant in no way disclaims these technical aspects, and it is contemplated that the claimed and/or disclosed inventions may encompass one or more conventional technical aspects.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

The present disclosure may address one or more of the problems and deficiencies of the art discussed above. However, it is contemplated that the present disclosure may prove useful in addressing other problems and deficiencies in a number of technical areas. Therefore, the claimed and/or disclosed inventions and present disclosure should not necessarily be construed as limited to addressing any of the particular problems or deficiencies discussed herein.

Briefly, the present disclosure satisfies the need for stable non- or minimally invasive, implant alignment or guide systems and methods that properly align an associated implant with the anatomical construct of a patient. The present disclosure provides laser alignment or guidance systems and methods to facilitate the implantation of implants. The laser alignment or guidance systems and methods facilitate proper alignment of the implant with the mechanical axis of an extremity of a patient. In some embodiments, the laser alignment or guidance systems and methods facilitate bone resection and implantation of the implant into one or more bones so that the implant is properly aligned with the mechanical axis (or another axis or anatomical axis or reference point) of the extremity of a patient. In one embodiment, the laser alignment or guidance systems and methods are ankle arthroplasty laser alignment systems and methods that properly align an ankle joint implant with the mechanical axis of the patient's leg. However, the laser alignment systems and methods of the present disclosure may be utilized with any anatomical structure(s) of a patient to align an implant with an axis (e.g., mechanical axis, weight-bearing axis, anatomical axis, etc.) of one or more anatomical structures of interest.

The laser alignment systems and methods of the present disclosure may be configured to provide alignment (e.g., manipulation to achieve alignment) in three planes (e.g., along or in the sagittal, coronal and transverse planes), covering six degrees of freedom. As noted above, the laser alignment systems and methods may facilitate proper alignment of an implant with a mechanical axis of one or more anatomical structures (e.g., a lower extremity), as opposed to the anatomical or weight bearing axis thereof, to provide an accurate and advantageous alignment.

In one aspect, the present disclosure provides a surgical method. The method comprises attaching a target base to the exterior a patient in a first location that is in substantial alignment with an alignment axis associated with an anatomical structure of interest of the patient. The method also comprises positioning a sterility barrier over the patient and the target base. The method further comprises coupling a target member to the target base such that the sterility barrier is positioned between the target member and the target base, the target member comprising a visual indicator or indication of the location of the alignment axis. The method also comprises coupling an implant guide to the patient proximate to the anatomical structure of interest. The method further comprises projecting a laser line from a laser device coupled to the guide. The method also comprises adjusting the guide such that the laser line is substantially aligned with the visual indication of the target member. The method further comprises utilizing the guide to implant an implant configured for the anatomical structure of interest in alignment with the alignment axis.

In some embodiments, the guide of the system is configured such that at least one outer engagement surface of the implanted implant that engages with bone and/or tissue of the anatomical structure of interest is substantially centered along the alignment axis. In some such embodiments, the alignment axis is a mechanical axis associated with the anatomical structure of interest. In some such embodiments, anatomical structure of interest is an ankle joint, and the alignment axis is the mechanical axis of the patient's lower limb extending between the patient's ankle and knee joints of the limb. In some other such embodiments, the anatomical structure of interest is an ankle joint, and the alignment axis is the mechanical axis of the patient's leg extending between the patient's ankle and hip joints of the limb. In some such embodiments, the first location is aligned with the center of the femoral head of the patient's leg.

In some embodiments, utilizing the guide to implant the implant comprises utilizing a resection guide coupled to the guide to resect at least one portion of the anatomical structure of interest. In some such embodiments, the method further comprises adjusting the guide to position the resection guide with respect to the anatomical structure of interest. In some embodiments, adjusting the guide such that the laser line is substantially aligned with the visual indication of the target member comprises adjusting the laser device along at least one of the medial-lateral direction and/or the varus-valgus direction. In some embodiments, the target base comprises a radiopaque portion that facilitates alignment of the target base along the alignment axis via radiography.

In another aspect, the present disclosure provides an implant alignment system. The system may comprise a target base configured to couple to the exterior of a patient in a first location that is in substantial alignment with an alignment axis associated with an anatomical structure of interest of a patient. The system may comprise a target member configured to couple to the target member that includes a visual indication of the location of the alignment axis. The system may comprise an implant guide configured to couple to the patient proximate to the anatomical structure of interest (such as to a distal tibia of an ankle joint).

The system may further comprise a laser device configured to project a laser light. The laser device may be configured to removably couple to the guide. For example, the laser device may include a tang, tab or projection configured to removably, but securely, fit within a slot or aperture of the guide. In some embodiments, the laser device may be configured to automatically activate the laser source of the laser device and emit the laser light/line when the laser device is coupled with the guide. The laser device may thereby be configured to automatically activate and would not need be to be physically engaged, and thereby potentially physically moved or disturbed, after it is coupled to the guide. For example, the tang of the laser device may include an electrical contact switch that is moved or deflected into an "on" position when the tang is inserted/positioned within the corresponding slot of the guide that activates the laser device such that the laser line is emitted.

The guide of the system may be configured to adjust the laser device (and a portion of the guide coupled thereto) such that the laser line is substantially aligned with the visual indication of the target member or another visual indication (such as an anatomical structure of interest (e.g., a tibial crest, a center of a knee, a femoral head of a hip, etc.)). For example, the guide may adjustable in a plurality of degrees of freedom such that the laser line, and potentially at least a portion of the guide itself, is properly aligned to the anatomical configuration/structures of the patient (e.g., to the alignment axis (e.g., an anatomical or mechanical axis) of anatomical structures of interest).

The guide may include adjustable portions that are configured to assist in aligning the guide to the anatomical configuration/structures of the patient (e.g., to the alignment axis (e.g., an anatomical or mechanical axis) of anatomical structures of interest) above that provided by the laser device. For example, the guide may include a radiolucent guide block that includes radiopaque members or portions that allow a user to determine/evaluate the orientation of the guide block (and/or one or more resections formed via the guide block) with respect to the anatomical configuration/structures of the patient under x-ray/fluoroscopy.

The guide may also include indications (e.g., externally-visible indications and/or radiopaque indications) that allow a user to determine/evaluate the size of the guide block (and/or one or more resections formed via the guide block) with respect to the anatomical configuration/structures of the patient. In some guide embodiments that include a guide block, the laser device may be configured to couple (e.g., removably couple) with the guide block, such as with a slot of the guide block representing a joint line of the anatomical configuration/structures of the patient (and/or of an implant replacing such configuration/structures).

As another example, the system may include a flat/planar wing member that extends from the laser device or guide and at least partially about at least one anatomical structure of interest (e.g., extends in at least two directions, such as medial-laterally and anteriorly-posteriorly) that allows a user to determine/evaluate the orientation (e.g., slope) of the guide block (and/or one or more resections formed via the guide block) with respect to the anatomical configuration/structures of the patient. For example, the wing member (itself or a flat surface thereof) may extend along a plane aligned with the joint line of the anatomical configuration/structures of the patient (e.g., an ankle joint) and/or of a particular implant replacing such configuration/structures (e.g., a total ankle replacement implant) implanted on/in a resected bone that is resected (at least partially) via the guide block or another portion of the guide.

The wing member may thereby allow a user to determine/evaluate the orientation (e.g., slope) of the joint line of the anatomical configuration/structures of the patient (e.g., an ankle joint) and/or of a particular implant replacing such configuration/structures (e.g., a total ankle replacement implant) implanted on/in a resected bone that is resected (at least partially) via the guide block or another portion of the guide along at least two directions (such as medial-laterally and anteriorly-posteriorly), potentially with respect to the mechanical or other alignment axis (e.g., an anatomical axis). In some such embodiments, the wing member may extend from the laser device, while in other embodiments the wing member may be configured to couple (e.g., removably couple) with the guide block, such as with a slot of the guide block representing the joint line of the anatomical configuration/structures of the patient (and/or of an implant replacing such configuration/structures).

If the guide includes a wing member, the guide may further include an elongate auxiliary alignment member or rod coupled to the wing member. The auxiliary alignment member may be movably coupled to the wing member, such as within a slot of the wing member (which may extend anteriorly-posteriorly). The auxiliary alignment member may be oriented perpendicular (in at least one direction) or normal to the wing member, and thereby perpendicular (in at least one direction) or normal to the joint line referenced by the wing member (as discussed above). The auxiliary alignment member may thereby allow a user to determine/evaluate the alignment (e.g., sagittal alignment) and/or orientation (e.g., sagittal slope and/or coronal slope) of the joint line of the anatomical configuration/structures of the patient (e.g., an ankle joint) and/or of a particular implant replacing such configuration/structures (e.g., a total ankle replacement implant) implanted on/in a resected bone that is resected (at least partially) via the guide block or another portion of the guide, potentially with respect to the mechanical or other alignment axis (e.g., an anatomical axis).

The laser device may be removably coupled to the guide such that after the guide and laser are properly aligned to the visual indication, the guide can be fixed to the patient (e.g., fixed to a bone of the patient via a k-wire or other fixation member) and the laser device decoupled or otherwise removed therefrom. The guide (after being properly aligned via the laser line of the laser device) may be utilized to facilitate implantation of a prosthesis. For example, at least a portion of the guide may be utilized to resect at least one portion of a bone or other anatomical structure of interest (e.g., a distal tibia) after the guide is aligned via the laser line (and potentially other mechanisms, such as via the indications of the guide block and/or the wing member discussed above) such that the resected surface(s) are configured in a manner that the implantation or coupling of a particular prosthesis thereon/therein is properly aligned to the anatomical configuration/structures of the patient (e.g., to the alignment axis (e.g., an anatomical or mechanical axis) of the anatomical structures of interest). In this way, the guide is configured such that when the laser line is substantially aligned with the visual indication, resection of an anatomical structure of interest via a resection guide portion of the guide facilities implantation of an implant on the anatomical structure of interest in alignment with an alignment axis.

In some embodiments, the system further comprises a sterility barrier configured to extend over the patient and the target base to maintain the sterility thereunder, and the target base and the target member are configured to couple together such that the sterility barrier is positioned therebetween. In some embodiments, the guide is configured such that when the laser line is substantially aligned with the visual indication, resection of the anatomical structure of interest via the resection guide facilities implantation of the implant such that at least one outer engagement surface of the implant that engages with bone and/or tissue of the anatomical structure of interest is substantially centered along the alignment axis. In some embodiments, the guide is configured to adjust the laser device along at least one of the medial-lateral direction and/or in the varus-valgus direction such that the laser line is substantially aligned with the visual indication. In some embodiments, the guide is further configured to adjusting the resection guide with respect to the anatomical structure of interest.

In some embodiments, the target base comprises a radiopaque portion that facilitates alignment of the target base along the alignment axis via radiography. In some embodiments, the laser device is configured to project a fan shaped laser light plane such that the incident laser light forms a substantially linear line. In some embodiments, the laser device is removably coupled with the guide. In some embodiments, at least one of the laser device and the resection guide are configured to be removably coupled with the guide.

In some embodiments, the implant is an ankle joint implant, and the guide is configured such that when the laser line is substantially aligned with the visual indication of the target member, resection of a distal tibia and/or talus of an ankle of the patient's leg via the resection guide facilities implantation of the implant therein in alignment with the mechanism axis of the patient's leg.

In one aspect, the present disclosure provides an implant alignment and resection guide system. The system comprises a target base configured to couple to the exterior of a patient in a first location that is in substantial alignment with an alignment axis associated with an anatomical structure of interest of a patient. The system also comprises a target member configured to couple to the target member, comprising a visual indication of the location of the alignment axis. The system also comprises a laser device configured to project a laser light. The system also comprises an implant guide configured to couple to the patient proximate to the anatomical structure of interest and couple with the laser device. The implant guide comprises a resection guide configured to resect at least one portion of the anatomical structure of interest. The implant guide is configured such that when the laser line is substantially aligned with the visual indication of the target member, resection of the anatomical structure of interest via the resection guide facilities implantation of an implant in the resected anatomical structure of interest such that the implant is in alignment with the alignment axis.

In some embodiments, the system further comprises a sterility barrier configured to extend over the patient and the target base, and the target base and the target member are configured to couple such that the sterility barrier is positioned therebetween. In some embodiments, the implant guide is configured such that when the laser line is substantially aligned with the visual indication of the target member, resection of the anatomical structure of interest via the resection guide facilities placement of the implant such that at least one outer engagement surface of the implant that engages with a bone and/or tissue of the anatomical structure of interest is substantially centered along the alignment axis. In some embodiments, the implant guide is configured to adjust the laser device and the resection guide along at least one of a medial-lateral direction and a varus-valgus direction such that the laser line is substantially aligned with the visual indication of the target member.

In some embodiments, the implant guide is further configured to adjust at least one of the position and the orientation of the laser device and the resection guide with respect to the anatomical structure of interest and the visual indication of the target member. In some embodiments, the target base comprises a radiopaque portion that facilitates alignment of the target base along the alignment axis. In some embodiments, the laser device is configured to project a fan shaped laser light plane such that the incident laser light forms a substantially linear line. In some embodiments, the laser device is removably coupled with the implant guide. In some embodiments, at least one of the laser device and the resection guide are configured to removably couple with the implant guide.

In some embodiments, the implant guide comprises a guide block that comprises a slot and the resection guide, the resection guide comprising at least one resection guide aperture configured to resect a portion of the anatomical structure of interest. In some embodiments, the laser device comprises a tang configured to removably mate within the slot of the guide block to removably couple the laser device and the guide block together. In some embodiments, the tang comprises a switch configured to energize the laser device from an energy storage device of the laser device such that the laser device projects the laser light therefrom in an activated state thereof and deenergizes the laser device such it does not project the laser light therefrom in a deactivated state thereof, and the tang and the slot are configured such that the switch is moved into the activated state from the deactivated state when the tang is seated within the slot.

In some embodiments, the system further comprises a planar wing member configured to removably couple with the slot of the guide block, the wing member being elongated along a pathway that extends in a first direction and a second direction. In some embodiments, the wing member comprises a second tang configured to removably mate within the slot of the guide block to removably couple the wing member and the guide block together. In some embodiments, the wing member extends from the tang of the laser device to removably couple the laser device and the wing member and the guide block together. In some embodiments, the system further comprises an elongate alignment rod configured to engage with the planar wing member in a normal orientation.

In some embodiments, the guide block and the laser device are configured such that when the laser device and the guide block are coupled together, the laser device projects a laser light line that is aligned with a center of the resected portion of the anatomical structure of interest. In some embodiments, the resected portion of the anatomical structure of interest is configured to engage with an implant, and the guide block and the laser device are configured such that when the laser device and the guide block are coupled together, the laser device projects a laser light line that is aligned with a center of the implant when the implant is mated with the resected portion of the anatomical structure of interest. In some embodiments, the implant guide is further configured to adjust at least one of the position and the orientation of the laser device and the resection guide with respect to the anatomical structure of interest and the visual indication of the target member In some embodiments, the guide block comprises a radiolucent material, and the guide block comprises a plurality of radiopaque guide members that identify at least one of an outer edge, position and orientation of the resected portion of the anatomical structure of interest. In some embodiments, the alignment guide further comprises adjustment components configured to adjust at least one of the position and the orientation of the laser device and the guide block when the laser device and the guide block are coupled together along a plurality of degrees of freedom. In some embodiments, the alignment guide further comprises adjustment components configured to adjust at least one of the position and the orientation of the laser device and the guide block when the laser device and the guide block are coupled together along a medial-lateral direction and a varus-valgus direction.

In some embodiments, the implant is an ankle joint implant, and the alignment guide is configured such that when the laser line is substantially aligned with the visual indication of the target member, resection of a distal tibia and/or talus of an ankle of the patient's leg via the resection guide facilitates positioning of the implant therein along the mechanical axis of the patient's leg.

In some embodiments, the system further comprises a reference member configured to couple to the patient such that the laser light projects thereon, and the reference member includes a plurality of visual indications as reference points to at least one of the position and orientation of the laser light. In some embodiments, the alignment axis is a mechanical axis or an anatomical axis of the anatomical structure of interest.

In one aspect, the present disclosure provides a surgical method comprising attaching a target base to the exterior a patient in a first location that is in substantial alignment with an alignment axis associated with an anatomical structure of interest of the patient. The method further comprises positioning a sterility barrier over the patient and the target base. The method further comprises coupling a target member to the target base such that the sterility barrier is positioned between the target member and the target base, the target member comprising a visual indication of the location of the alignment axis. The method further comprises coupling an implant guide to the patient proximate to the anatomical structure of interest. The method further comprises projecting a laser line from a laser device coupled to the implant guide. The method further comprises adjusting at least one of the position and orientation of the alignment guide such that the laser line is substantially aligned with the visual indication of the target member. The method further comprises utilizing a resection guide portion of the implant to resect a portion of the anatomical structure of interest for implantation of an implant therein that is in alignment with the alignment axis.

In some embodiments, the alignment guide is configured such that at least one outer engagement surface of the placed implant that engages with a bone and/or tissue of the anatomical structure of interest is substantially centered along the alignment axis. In some embodiments, the alignment axis is a mechanical axis associated with the anatomical structure of interest. In some embodiments, the anatomical structure of interest is an ankle joint, and the alignment axis is the mechanical axis of the patient's leg. In some embodiments, the first location is aligned with the center of the femoral head of the patient's leg. In some embodiments, the anatomical structure of interest is an ankle joint, and the alignment axis is the mechanical axis of the patient's lower limb extending between the patient's ankle and knee joints of the limb.

In some embodiments, the target base comprises a radiopaque portion that facilitates alignment of the target base along the alignment axis via radiography. In some embodiments, adjusting at least one of the position and orientation of the alignment guide such that the laser line is substantially aligned with the visual indication of the target member comprises adjusting at least a portion of the alignment guide along at least one of a medial-lateral direction and a varus-valgus direction.

In some embodiments, coupling an implant guide to the patient proximate to the anatomical structure of interest comprises coupling a guide block that comprises a slot and the resection guide proximate to the anatomical structure of interest, the resection guide comprising at least one resection guide aperture configured to resect a portion of the anatomical structure of interest.

In some embodiments, the laser device comprises a tang, and the method further comprises removably mating the tang within the slot of the guide block to removably couple the laser device and the guide block together. In some embodiments, the tang comprises a switch configured to energize the laser device from an energy storage device of the laser device such that the laser device projects the laser light therefrom in an activated state thereof and deenergizes the laser device such it does not project the laser light therefrom in a deactivated state thereof, and removably mating the tang within the slot of the guide block moves the switch into the activated state from the deactivated state.

In some embodiments, the method further comprises removably coupling a planar wing member with the slot of the guide block, the wing member being elongated along a pathway that extends in a first direction and a second direction. In some embodiments, the method further comprises adjusting at least one of the position and orientation of the guide block with reference to at least one of the position and orientation of the wing member with respect to the anatomical structure of interest.

In some embodiments, the guide block is formed of a radiolucent material and comprises a plurality of radiopaque guide members that identify at least one of an outer edge, position and orientation of the resected portion of the anatomical structure of interest, and further comprising adjusting at least one of the position and orientation of the guide block with reference to at least one of the position and orientation of the radiopaque guide members with respect to the anatomical structure of interest under fluoroscopy. In some embodiments, the alignment axis is a mechanical axis or an anatomical axis of the anatomical structure of interest.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the laser-based implant alignment or guidance systems and methods disclosed herein, there is shown illustrative embodiments. These illustrative embodiments are in no way limiting in terms of the precise arrangement and operation of the disclosed laser-based implant alignment or guidance systems and methods, and other similar embodiments are envisioned within the spirit and scope of the present disclosure.

DETAILED DESCRIPTION

Figure 1:
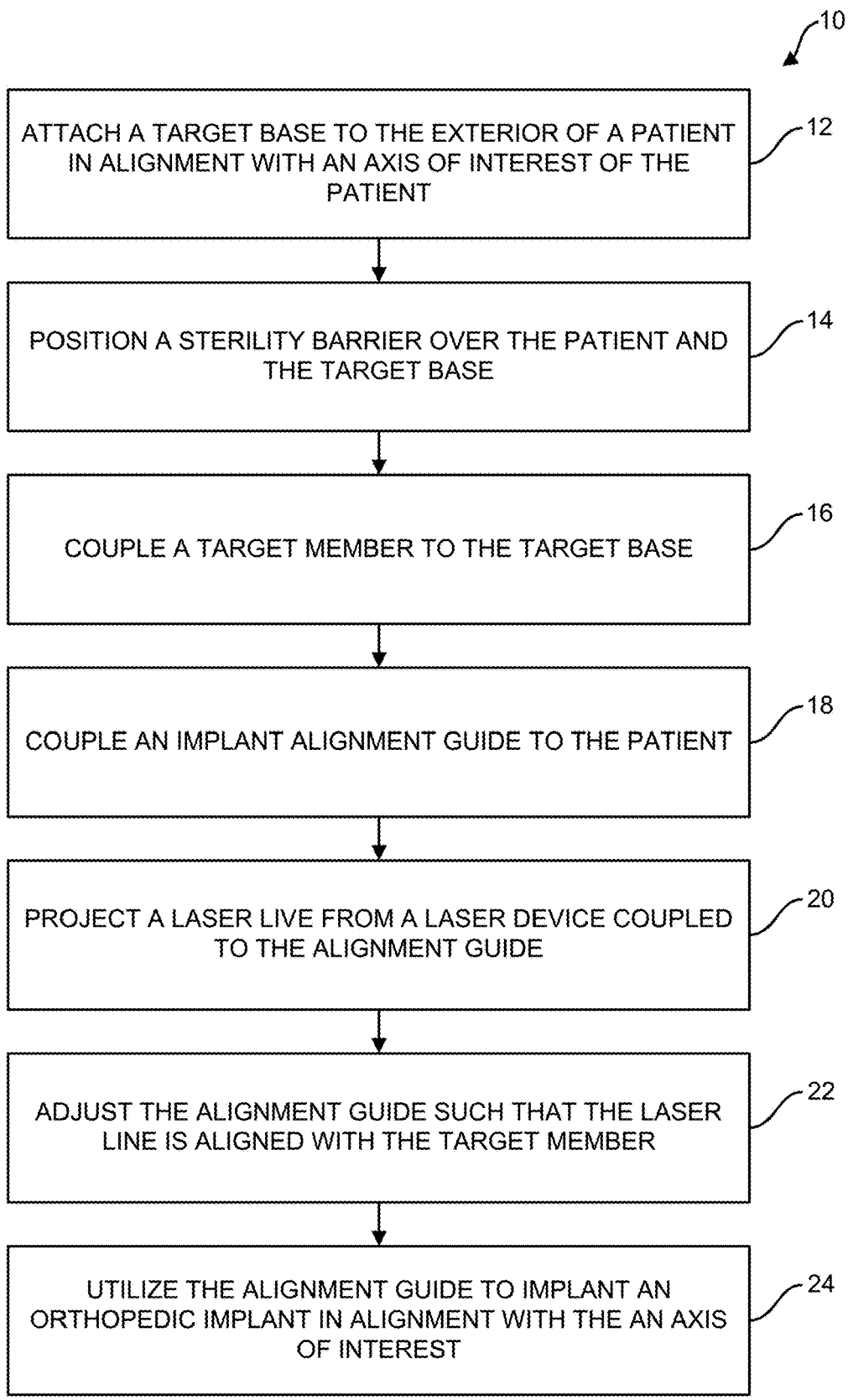
FIG. 1 is a flow chart illustrating an implant alignment and guide method utilizing a laser-based implant alignment system according to the present disclosure.

Aspects of the present disclosure and certain features, advantages, and details thereof are explained more fully below with reference to the non-limiting embodiments illustrated in the accompanying drawings. Descriptions of well-known materials, fabrication tools, processing techniques, etc., are omitted to not unnecessarily obscure the present disclosure in detail. It should be understood, however, that the detailed description and the specific example(s), while indicating embodiments of the present disclosure, are given by way of illustration only, and are not by way of limitation. Various substitutions, modifications, additions and/or arrangements within the spirit and/or scope of the underlying inventive concepts will be apparent to those skilled in the art from this disclosure.

The present disclosure provides stable laser-based implant alignment or guide systems and methods that properly align an associated implant with an anatomical construct of a patient. The systems and methods do not require additional incisions or trauma above that associated with the implantation process of the implant. Thereby, the laser-based implant guide systems and methods do not necessitate guide-specific incisions or trauma to the patient.

The laser-based implant alignment systems and methods of the present disclosure may be configured to provide alignment of the implant with an anatomical structure or construct of a patient in at least three planes (e.g., in or along the sagittal, coronal and transverse planes), covering six degrees of freedom, such as via user selectable manipulation or variation in bone resection and/or implant implantation (e.g., via bone drilling, cutting or other bone preparation), as explained further below.

The laser-based implant alignment or guidance systems and methods facilitate proper alignment of an implant with, for example, an "alignment" axis of one or more anatomical structure or construct of interest. For example, the systems and methods may be utilized to align an implant with the mechanical axis, weight bearing axis, anatomical axis or any other axis of one or more anatomical structure or construct of a patient, such as that of an extremity of a patient, generally referred to herein as an "alignment axis." However, the laser-based implant alignment systems and methods of the present disclosure may be utilized with any anatomical structure(s) of a patient to align an implant with an axis (e.g., mechanical axis, weight-bearing axis, anatomical axis, etc.) of one or more anatomical structures of interest. In some embodiments, the laser-based implant alignment systems and methods provide alignment of an implant with the mechanical axis of a lower extremity (i.e., a leg) of a patient, as explained further below. For example, the laser-based implant alignment systems and methods may be configured to facilitate bone resection and implantation of an implant into/to the tibia and/or talus bones so that the implant is properly aligned with the mechanical axis of the leg of the patient. In this way, the laser-based implant alignment systems and methods may comprise ankle arthroplasty laser alignment systems and methods that properly align an ankle joint implant with the mechanical axis of a patient's leg.

The mechanical axis of a lower extremity or leg, as used herein, refers to the axis or straight line that passes through the center of the femoral head to the center of the ankle joint. This mechanical axis may also be referred to as the weight bearing axis of one's lower extremity (and is used interchangeably herein). The mechanical axis typically does not pass through the three-dimensional anatomic center of the knee, and commonly corresponds to an approximate 3° slope compared to the vertical axis.

One's lower extremity may also be divided into a femoral mechanical axis that runs from the center of the femoral head to the center of the distal end of the femur (e.g., at the intercondylar notch), and a tibial mechanical axis that extends from the center of the proximal end of the tibia to the center of the distal end of the tibia. The anatomical axis of an extremity is typically defined as a line that bisects the medullary canal of one or more bones thereof. For example, the anatomical axis of one's lower extremity is typically identified as the line that bisects the medullary canal of the tibia and/or the femur.

In some individuals, the anatomic axis of the femur is about 6 degrees valgus or varus from the mechanical axis of the leg, and/or about 9 degrees valgus or varus from the vertical axis (although such relative orientations vary according to individual body habitus). In some individuals, the anatomic axis of their tibia is about 2 or 3 degrees valgus or varus from the mechanical axis of the leg (although such relative orientation varies according to individual body habitus). The anatomic axes of a tibia and femur commonly intersect at the knee at an angle of about 6 degrees (although such relative orientation varies according to individual body habitus).

The laser-based implant alignment systems and methods may facilitate proper alignment of an implant with the mechanical/weight bearing axis of one or more anatomical structures (e.g., a lower extremity), as opposed to one or more anatomical axis thereof, to provide an accurate and advantageous alignment. With respect to an ankle arthroplasty, the laser-based implant alignment systems and methods may be configured to properly align an ankle joint implant with the mechanical axis of the patient's leg. For example, the laser-based implant alignment systems and methods may facilitate or determine bone resection and/or ankle joint implant implantation with respect to the tibia and/or talus bones of a patient's leg (i.e., completion of an ankle arthroplasty) so that the ankle joint (e.g., the coronal plane thereof) formed at least in part by the implant is aligned with the mechanical axis of the leg, as explained further below.

As described above, the Applicant has determined that alignment of an ankle joint with the mechanical/weight bearing axis of a patient, formed at least in part by an implant, advantageously mechanically transfers load during ambulation from the ground, through the foot, through the knee and into the hip. The Applicant has recognized that malalignment of an ankle joint from the mechanical axis of the patient's leg can cause pain, injury, deformity, implant failure, and, thereby, a diminished quality of life.

FIG. 1 is a flow diagram of an exemplary laser-based implant alignment and guide method 10 according to the present disclosure. The alignment method 10 of FIG. 1 is generally illustrated in FIGS. 2, 4, 7 and 13 with respect to a human patient (although the patient may be non-human (e.g., another mammal). The alignment method 10 of FIG. 1 is generally demonstrated in FIGS. 2-17 with respect to an exemplary laser-based implant alignment or guide system according to the present disclosure. While the exemplary laser-based implant alignment and guide method 10 and exemplary laser-based implant alignment or guide system are shown and described with respect alignment of an ankle joint implant with the mechanical axis of a patient's leg, the implant alignment and guide method 10 and system are not limited to such embodiments and may equally or similarly be applied and configured with respect to other anatomical structures or constructs of a patient without departing from the general spirit and scope thereof, as one of ordinary skill in the art would appreciate.

Figure 2:
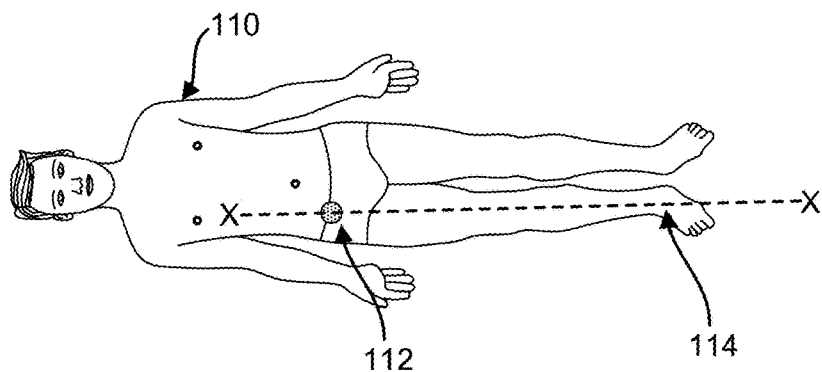
FIG. 2 illustrates placement of a target base of the alignment system on a patient according to the alignment method of FIG. 1.

As shown in FIGS. 1-2, the laser-based implant alignment and guide method 10 may include placing, removably or temporarily attaching 12, a target base 112 of the alignment or guide system to the skin or exterior of a patient 110. As shown in FIG. 2, the target base 112 may be placed on the exterior of the patient 110 such that its center (and/or an axis indication of a target member 118 that is ultimately coupled to the target base 112, as described further below) is substantially aligned with an axis X-X associated with at least one anatomical aspect or construct of interest 114 of the patient 110. In some embodiments, the target base 112 may be temporarily or removably attached 12 to the exterior of the patient 110 along or aligned with the mechanical or weight bearing axis X-X of at least one anatomical structure or construct 114 of the patient 110, as shown in FIGS. 1 and 2.

With respect to an ankle joint 114 of a lower extremity or leg of a patient 110, the target base 112 may be attached 12 to the exterior of the patient 110 along or aligned the mechanical axis X-X of the patient's lower extremity, as shown in FIG. 2. For example, the user may examine the patient 110 (e.g., via palpation) to locate the center of patient's femoral head, and attach 12 the target base 112 to this location on the exterior or skin of the patient 110, as shown in FIG. 2. If the axis X-X is not present at the exterior of the patient, the target base 112 may be removably attached 12 to the exterior of the patient 110 in a location that approximates the axis X-X or is substantially aligned with the axis X-X in as many planes or directions as possible (e.g., substantially aligned along the medial-lateral and proximal-distal directions but spaced along the anterior-posterior direction).

Figure 3:
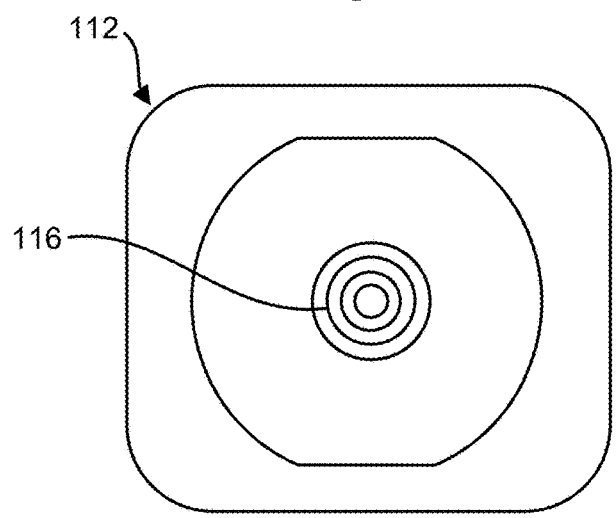
FIG. 3 illustrates an exemplary target base according to FIG. 2.

As shown in FIG. 3, the target base 112 may be configured to removably attach to the exterior of a patient 110 to avoid an incision into, or other trauma to, the patient 110. The target base 112 may thereby be pre-operatively applied to the patient 110. In some embodiments, the target base 112 may include an adhesive on an engagement surface thereof that is configured to be removably attached to the exterior of a patient (e.g., the skin of the patient 110). In some embodiments, the target base 112 may include at least one radiopaque component or aspect. In such embodiments, the method 10 may include imaging (e.g., x-ray imaging) the patient 110 after the target base 112 is coupled 12 to the patient 110 to ensure the target base 112 is aligned with or approximates the axis X-X. For example, with respect to an ankle arthroplasty, the patient 110 may be imaged to ensure the target base 112 is located at, or aligned with, the center of the patient's femoral head so that the target base 112 is aligned with the mechanical axis X-X of the patient's leg, as shown in FIG. 2.

As shown in FIG. 3, the target base 112 may include an attachment or coupling member 116 configured to removably mate with that of a target member 118, such as via an indirect connection through a sterility barrier 120 as described further below with respect to FIGS. 4-6. The coupling member 116 of the target base 112 may be provided at an opposing side of the target base 112 relative to the patient engagement surface. In some embodiments, the coupling member 116 may be configured to form a mechanical connection (e.g., an indirect connection) with the target member 118. For example, as shown in FIG. 3, the coupling member 116 may form one component or half of a snap button or other similar coupling mechanism. However, the coupling member 116 of the target base 112 may form any mechanical connection mechanism for coupling (e.g., removably, indirectly coupling) with the target member 118 (potentially through a sterility barrier 120).

In another embodiment (not shown), the coupling member 116 of the target base 112 may be configured to form a magnetic connection (e.g., an indirect connection) with a target member 118. For example, the coupling member 116 may be magnetic and the target member 118 may include an aspect or material that is attracted to the magnetic field of the coupling member 116, or vice versa. In some embodiments, the coupling member 116 may comprise the radiopaque component of the target base 112.

Figure 4:
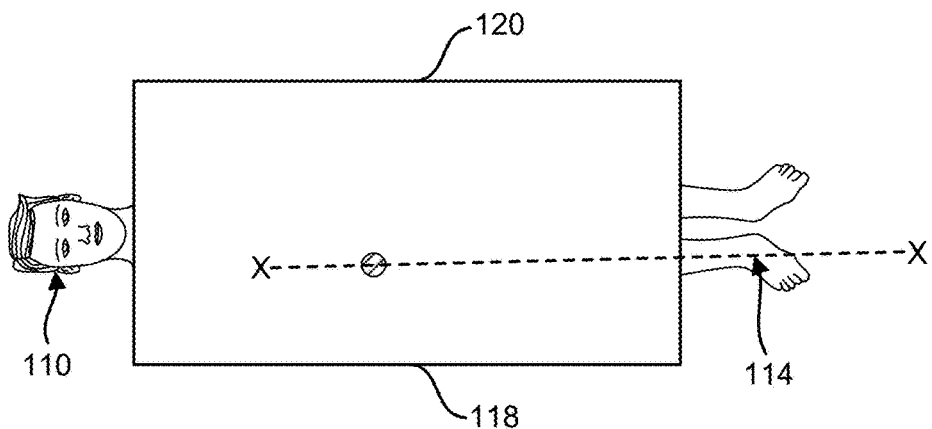
FIG. 4 illustrates placement of a sterility barrier and target member of the alignment system on the patient according to the alignment method of FIG. 1.

As shown in FIGS. 1 and 4, the laser-based implant alignment and guide method 10 may include positioning or placing 14 a sterility barrier 120 over the patient 110 and the target base 112. The sterility barrier 120 may be a surgical drape or other barrier that overlaps or overlies at least a portion of the patient 110 and the target base 112 to maintain, or at least help maintain, the sterility thereunder and/or the sterility of the least one anatomical aspect or construct of interest 114, as shown in FIG. 4. As also shown in FIG. 4, with respect to an ankle arthroplasty, the sterility barrier 120 may cover a proximal portion of the patient 110 and the target base 112, while leaving the distal ankle area 114 of the patient 110 exposed.

As shown in FIGS. 1 and 4-6, the laser-based implant alignment and guide method and system 10 may include coupling 16 (e.g., removably coupling) the target member 118 to the target base 112. In some embodiments, target member 118 may be indirectly coupled to the target base 112 via the coupling member 116 through the sterility barrier 120. For example, the target member 118 may include a coupling member 126 that is configured to mate with the coupling member 116 of the base target 116 with the sterility barrier 120 positioned there-between. The coupling members 116, 126 may thereby trap the sterility barrier 120 there-between and couple (e.g., removably couple) the target member 118, the target base 112 and the sterility barrier 120 together. The target member 118 may thereby couple to the target base 116 through the sterility barrier 120 without disrupting the sterile field formed beneath the sterility barrier 120. In other embodiments, at least one of the target base 112 and the target member 118 may pass through the sterility barrier 120 such that the coupling members 116, 126 directly couple together.

Figure 5:
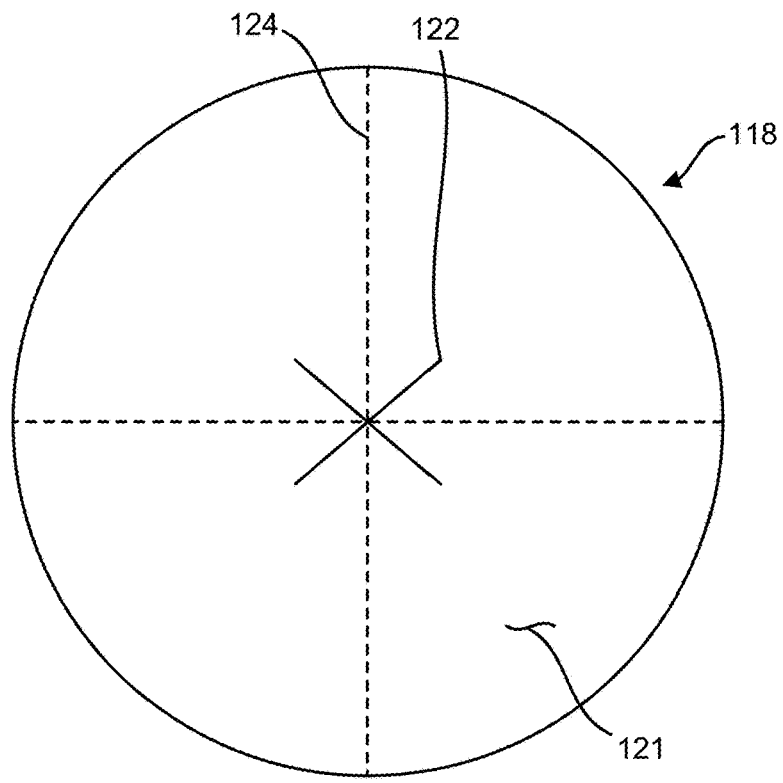
FIG. 5 illustrates a top view of an exemplary target member according to FIG. 4.
Figure 6:
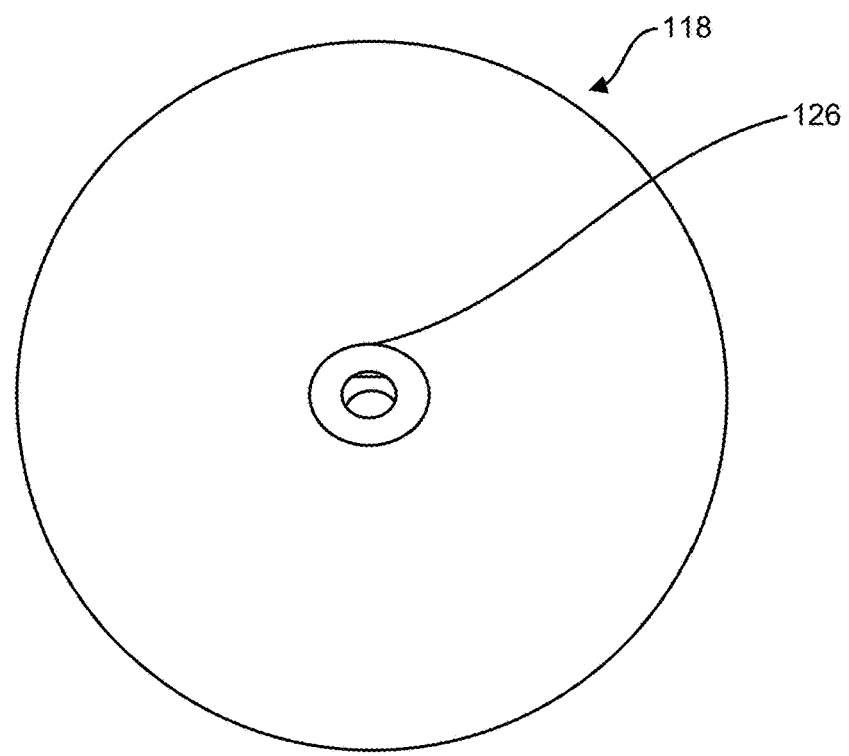
FIG. 6 illustrates a bottom view of an exemplary target member according to FIG. 4.

As shown in FIG. 6 and as discussed above with respect to the coupling member 116 of the base target 112, the coupling member 126 of the target member 118 may be configured to removably mate with coupling member 116 of the base target 112. The coupling member 126 may be provided at an opposing side of the target member 118 than a target indication surface 121 thereof, as shown in FIGS. 5 and 6. In some embodiments, the coupling member 126 may be configured to form a mechanical connection (e.g., an indirect connection) with the target base 112. For example, as shown in FIG. 6, the coupling member 126 may form one component or half of a snap button or other similar coupling mechanism. However, the coupling member 126 of the target member 118 may form any mechanical connection mechanism for coupling (e.g., removably, indirectly coupling) with the coupling member 116 of the target base 112 (potentially through a sterility barrier 120). In another embodiment (not shown), the coupling member 126 of the target member 118 may be configured to form a magnetic connection (e.g., an indirect connection) with the target base 112. For example, the coupling member 126 may be magnetic and the target base 112 may include an aspect or material that is attracted to the magnetic field of the coupling member 126, or vice versa.

The target indication surface 121 of the target member 118 may include a visual indicator or indication 122 of the location of the axis X-X (which was previously located and then indicated via placement of the target base 116), as shown in FIG. 5. In some embodiments, the visual indication 122 may identify the center of the target member 118, such as with a dot, crossed lines, "X" indication or any other visual indication. The visual indication 122 of the target indication surface 121 of the target member 118 may thereby indicate the location of the axis X-X of interest through the sterility barrier 120 without disrupting the sterile field. The target indication surface 121 and/or the visual indication 122 of the target member 118 may be configured such that a laser line is clearly visible when projected thereon. For example, the color, surface finish, and/or material of the target indication surface 121 and/or the visual indication 122 of the target member 118 may be configured such that a laser line projected thereon is clearly discernable.

As also shown in FIG. 5, to facilitate determination of alignment and/or calibration of the laser device 132, the target indication surface 121 of the target member 118 may include at least one visual axis indication 124 that passes through the visual indication 122 that indicates the location of the axis X-X of the anatomical structure of interest 114. One more visual axis indications 124 of the target indication surface 121 of the target member 118 may be utilized as a reference of the location and/or orientation of the laser light 138 from the laser device 132 that is incident of the target member 118 (e.g., with respect to the visual indication 122). The visual indication 122 may thereby correspond to the axis X-X of the anatomical structure of interest 114 when the target member 118 is coupled to the patient 110. In some embodiments, the axis indication 124 may be a line (dashed or solid), crossed lines or an "X" indication, or any other linear or axial visual indication.

Figure 7:
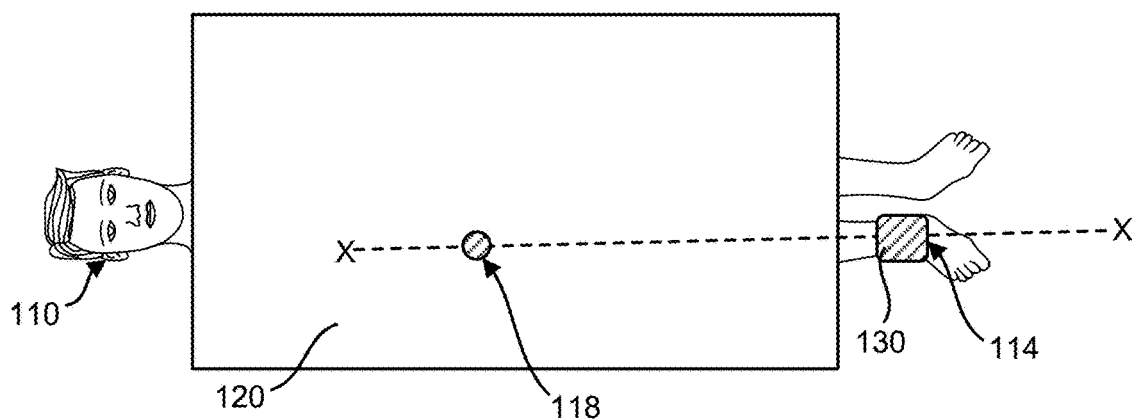
FIG. 7 illustrates attachment of an exemplary laser-including implant alignment device of the alignment system according to the alignment method of FIG. 1.

As shown in FIGS. 1 and 7, the alignment method 10 may include coupling 18 an implant alignment guide 130 to the patient 110, such as to the at least one anatomical structure or construct 114 of the patient 110. In some embodiments, the implant alignment guide 130 may be removably coupled to the at least one anatomical structure or construct 114 of the patient 110. For example, the implant alignment guide 130 may be removably coupled to a bone and/or tissue via at least one pin, k-wire, nail, screw, suture or any other biologically-compatible removable coupling mechanism. It is noted that the alignment guide 130 may be coupled to at least one anatomical structure or construct 114 of the patient 110 in a neutral or "zeroed-out" state. From the neutral state, the guide 130 may be utilized to properly align an implant to the axis X-X, as described further below.

As shown in FIG. 7, in some embodiments the implant alignment guide 130 may be coupled to the patient 110 at least generally along or about the axis X-X of interest. For example, one or more incisions may be made into the patient 110 to expose the at least one anatomical structure or construct 114 of interest. In some embodiments, the anatomical structure or construct 114 may be two or more bones that form a joint, and the incision(s) may expose at least a portion of the bones and the joint. In an ankle arthroplasty, for example, incision(s) may expose at least a portion of the distal tibia and the talus. In some such embodiments, the alignment guide 130 may be attached to at least the distal tibia of the patient 110. In some embodiments if the anatomical structure or construct 114 of interest is a joint, the joint may be retracted after it is exposed.

Figure 8:
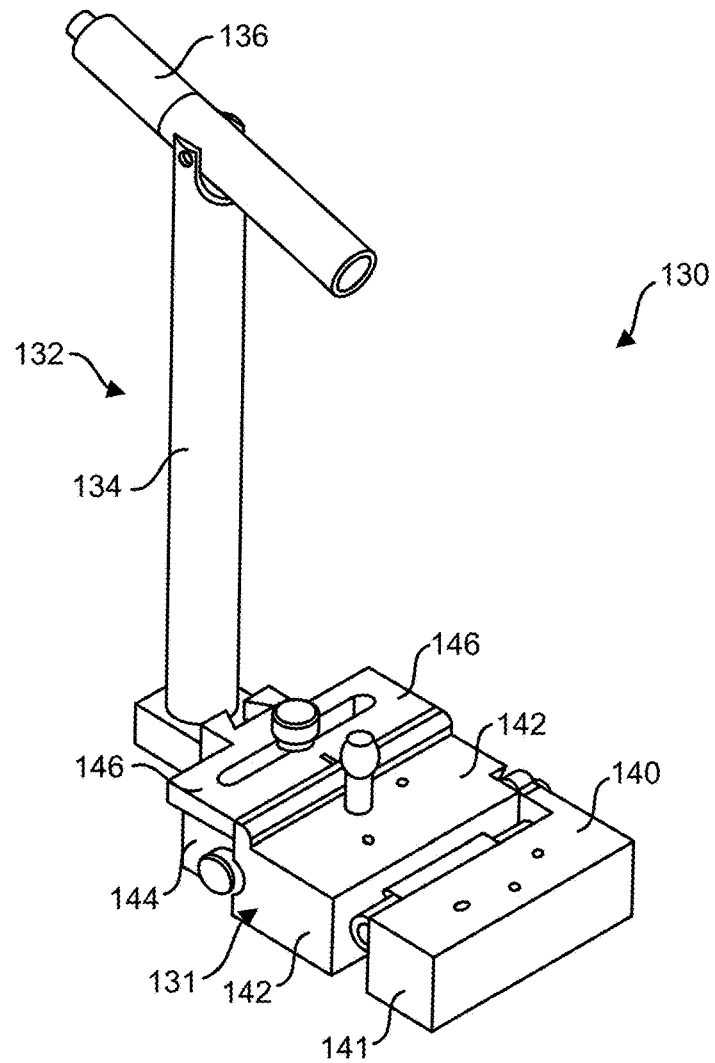
FIG. 8 illustrates an elevational perspective view of an exemplary implant alignment device with an attached laser device.
Figure 9:
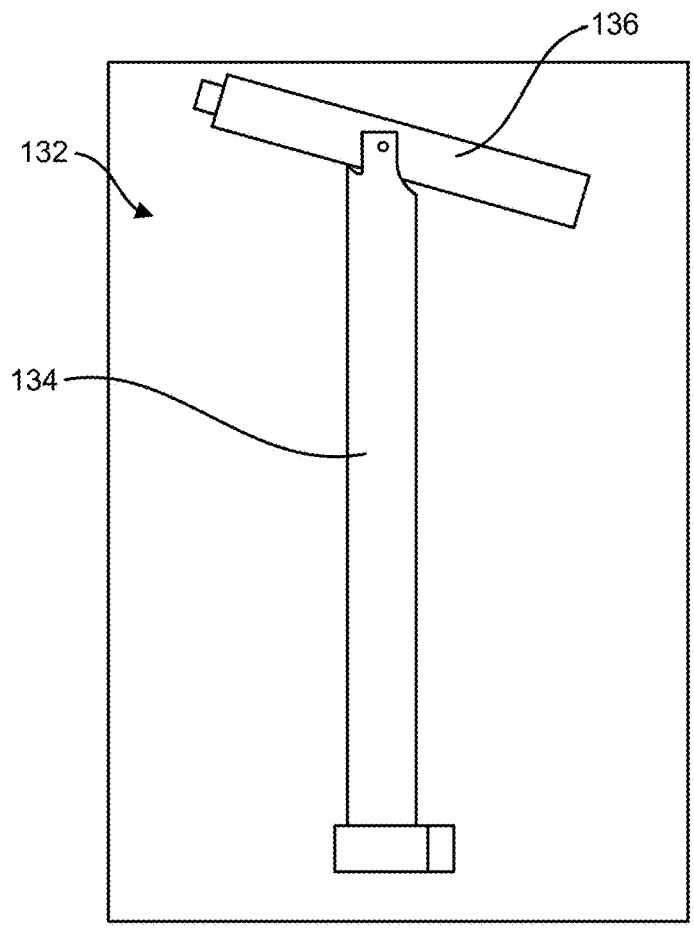
FIG. 9 is a side view of the laser device of the alignment device of FIG. 8.
Figure 12:
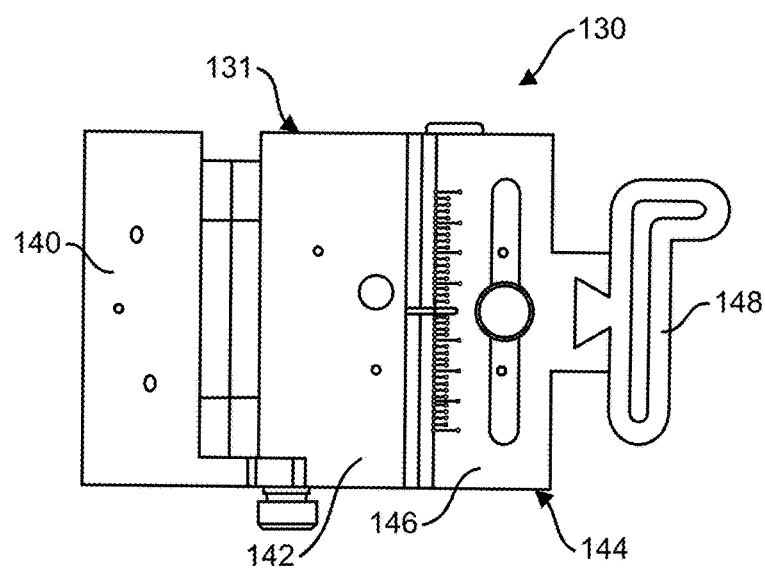
FIG. 12 illustrates a top view of the alignment device according to FIG. 10 with an exemplary cutting guide.

As shown in FIGS. 8 and 9, the alignment guide 130 may include a laser device 132. The laser device 132 may be coupled to the alignment guide 130 at a predetermined or defined fixed position and orientation with respect to other aspects of the alignment guide 130. The laser device 132 may be fixedly or permanently coupled to the alignment guide 130 or removably coupled as shown in FIGS. 8, 9 and 12. In one embodiment, as shown in FIGS. 8 and 9, the laser device 132 may couple to a base portion 131 of the alignment guide 130 via dovetail connection. However, any other attachment or coupling mechanism or configuration may equally be utilized. In some embodiments, the alignment method 10 may include coupling the laser device 132 to the base portion 131 of the alignment guide 130, such as prior to coupling 18 the implant alignment guide 130 to the patient 110 or subsequent to coupling 18 the implant alignment guide 130 to the patient 110. In some other embodiments, the alignment guide 130 may be provided or obtained with the laser device 132 coupled to the base portion 131.

Figure 10:
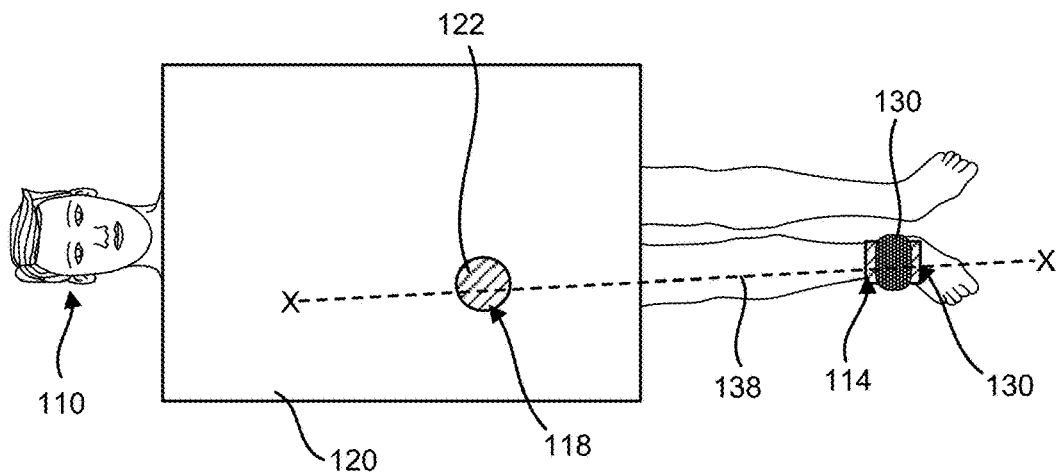
FIG. 10 illustrates alignment of the laser-including implant alignment device of the alignment system according to the alignment method of FIG. 1.
Figure 11:
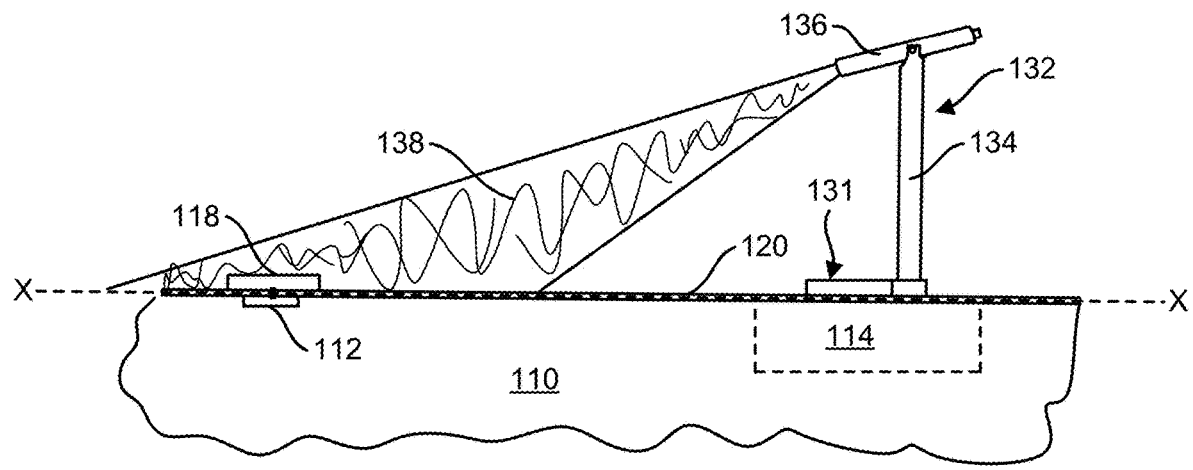
FIG. 11 illustrates a side view of FIG. 10.

As shown in FIGS. 8 and 9, the laser device 132 may include a support member, arm or post 134 that elevates a laser generating and/or projecting device 136 from the base portion 131 of the alignment guide 130 and/or the patient 110. For example, the support member 134 may elevate the laser generating and/or projecting device 136 above the base portion 131 and/or the patient 110 along an anterior direction. The support member 134 may elevate the laser generating and/or projecting device 136 above the base portion 131 and/or the patient 110 so that the device 136 is capable of projecting a laser line or point 138 that is incident on the target indication surface 121 of the target member 118, as shown in FIGS. 10 and 11. The alignment guide 130 may thereby be positioned below (in elevation) the target member 118 to at least some degree without interfering with the laser generating and/or projecting device 136 projecting a laser 138 that is incident on the target indication surface 121.

In some embodiments, the support member 134 and the laser generating and/or projecting device 136 may be fixedly coupled. In other embodiments, as shown in FIGS. 8 and 9, the support member 134 and the laser generating and/or projecting device 136 may be movably coupled. For example, as shown in FIGS. 8 and 9, the support member 134 and the laser generating and/or projecting device 136 may be pivotably or rotatably coupled such that the laser generating and/or projecting device 136 can be adjusted along an axis, but is otherwise maintained in a fixed predetermined alignment with the base portion 131 of the guide 130 (and the patient 110—as the guide 130 is securely coupled to the patient 110), such as along all other directions other than the pivot or rotation plane or axis.

As shown in FIGS. 1, 10 and 11, with the alignment guide 130 coupled to the anatomical structure or construct of interest 114 of the patient 110, and the laser device 132 coupled to the alignment guide 130, the alignment method 10 may include projecting 20 laser light 138 from the laser generating and/or projecting device 136.

With the laser light 138 projecting from the laser generating and/or projecting device 136, the alignment method 10 may include adjusting 22 the alignment guide 130 such that the laser line or point 138 is aligned with the visual indication 122 of the target indication surface 121 of the target member 118, as shown in FIGS. 1, 10 and 11. As discussed above, the visual indication 122 may identify the location of the axis X-X (which was previously located indicated via placement of the target base 116) associated with the anatomical structure or construct of interest 114, such as the mechanical or weight bearing axis of a lower extremity. Adjusting 22 the alignment guide 130 such that the laser line or point 138 is aligned with the visual indication 122 of the target indication surface 121 of the target member 118 may thereby properly align the alignment guide 130 to the axis X-X of the anatomical structure or construct of interest 114 of the patient 110.

Figure 13:
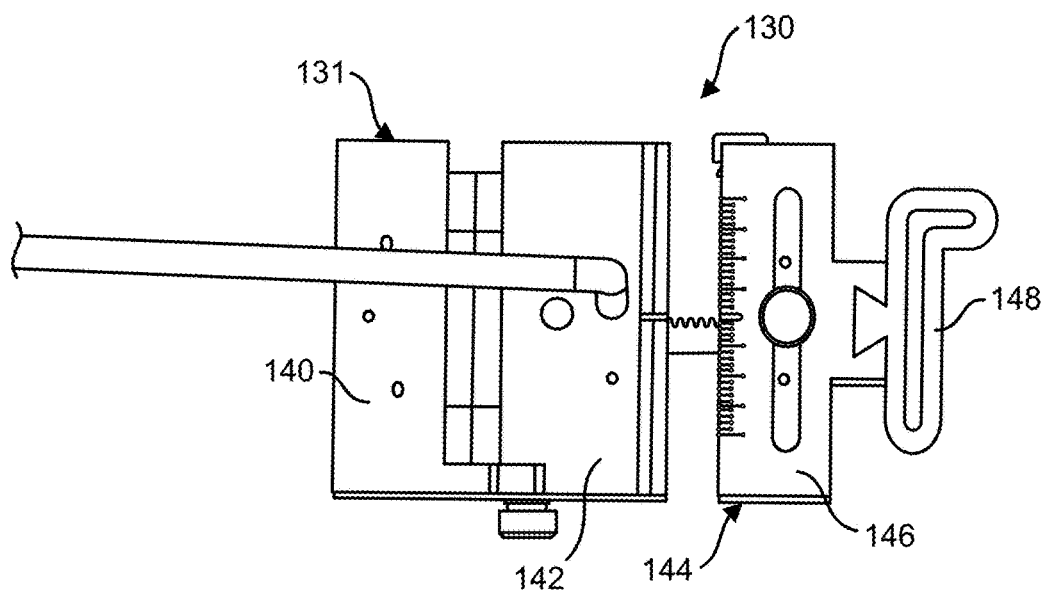
FIG. 13 illustrates a top view of the alignment device according to FIG. 12 being adjusted.
Figure 14:
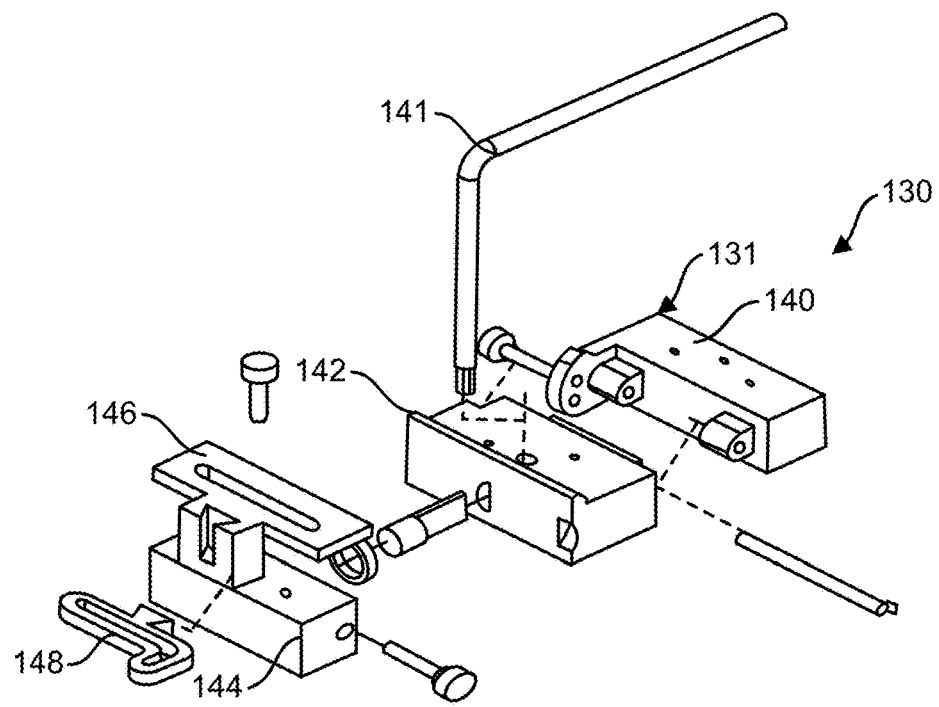
FIG. 14 illustrates an elevational perspective exploded view of the alignment device according to FIG. 12.
Figure 15:
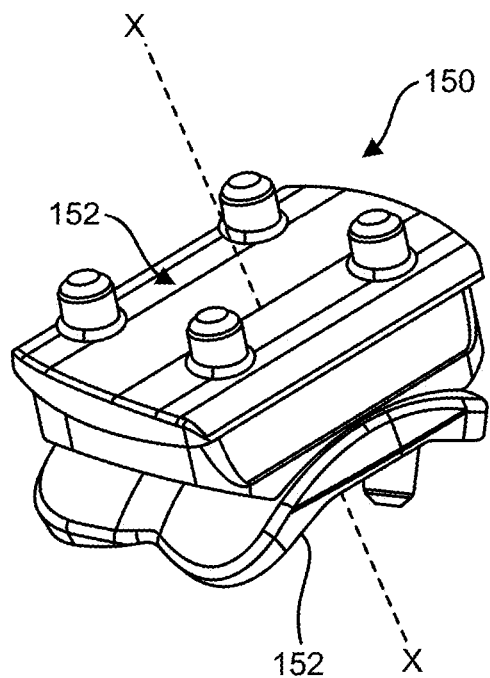
FIG. 15 illustrates a rear elevational perspective view of an exemplary implant that may be aligned via the alignment system and method according to the present disclosure.
Figure 16:
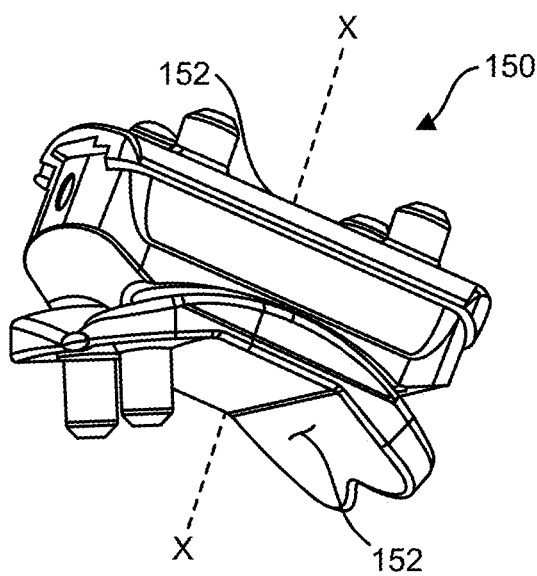
FIG. 16 illustrates a side perspective view of the implant of FIG. 15.
Figure 17:
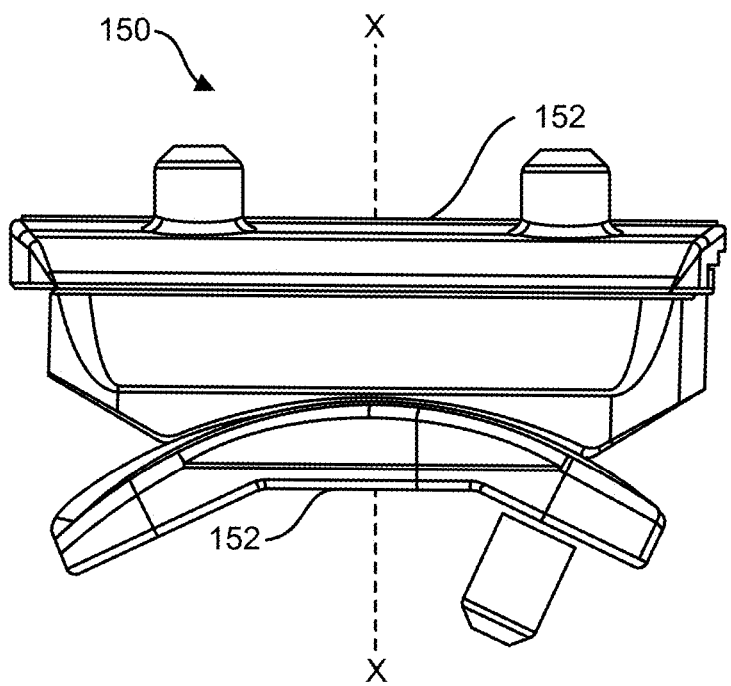
FIG. 17 illustrates a side view of the implant of FIG. 15.
Figure 18:
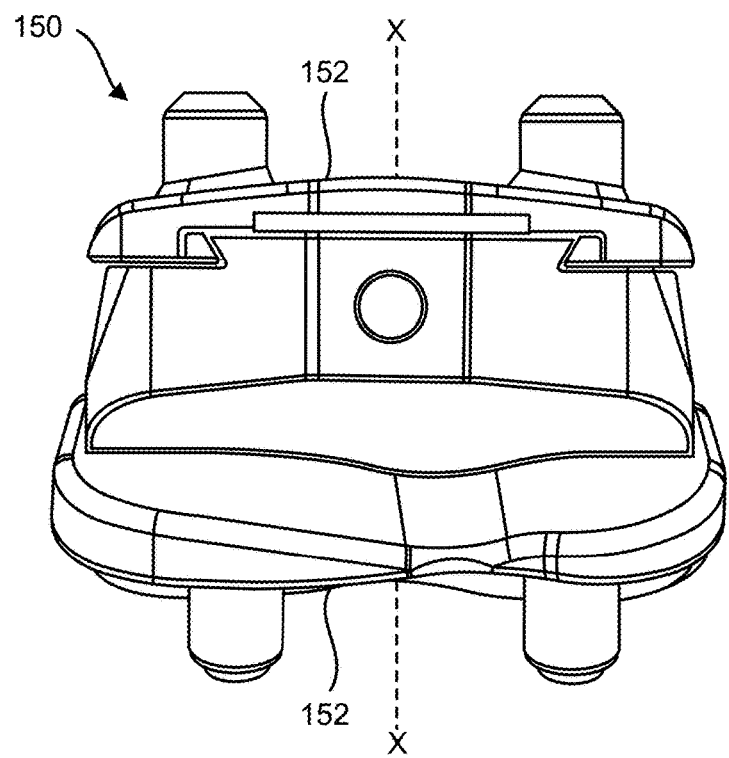
FIG. 18 illustrates a front view of the implant of FIG. 15.

The alignment guide 130 may be configured to be adjusted in at least one degree of freedom. In some embodiments, the alignment guide 130 may be configured to adjust in a plurality of degrees of freedom. For example, as shown in FIGS. 12-14, the alignment guide 130 may be configured to adjust in five (5) degrees of freedom. In some embodiments, the alignment guide 130 may be adjustable in or with respect to a first direction or plane, which may extend along or correspond to a sagittal plane when the alignment guide 130 is positioned on the anterior side of the patient 110 (i.e., flexion/extension adjustment) (e.g., when utilized in an ankle arthroplasty). In one such embodiment, the alignment guide 130 may be rotationally or angularly adjustable at least 10 or 20 degrees in or with respect to the first direction or plane. For example, the alignment guide 130 may be configured to provide about 26 degrees of total rotational/angular movement/adjustment in the first direction or plane.

In some embodiments, the alignment guide 130 may be adjustable in or with respect to a second direction or plane, which may extend along or correspond to the transverse plane when the alignment guide 130 is positioned on the anterior side of the patient 110 (i.e., internal/external adjustment) (e.g., when utilized in an ankle arthroplasty). In one such embodiment, the alignment guide 130 may be rotationally or angularly adjustable at least 20 degrees in or with respect to the second direction or plane. For example, the alignment guide 130 may be configured to provide about 24 or 90 degrees of total rotational/angular movement/adjustment in the third direction or plane, such as depending upon if the guide 130 is not adjusted or fully adjusted in flexion/extension.

In some embodiments, the alignment guide 130 may be adjustable in or with respect to a third direction or plane, which may extend along or correspond to the coronal plane when the alignment guide 130 is positioned on the anterior side of the patient 110 (i.e., varus/valgus adjustment) (e.g., when utilized in an ankle arthroplasty). In one such embodiment, the alignment guide 130 may be rotationally or angularly adjustable at least 10 or 20 degrees in or with respect to the third direction or plane (i.e., at least 20 degrees of total movement/adjustment is provided). For example, the alignment guide 130 may be configured to provide about 90 degrees of total rotational/angular movement/adjustment in the third direction or plane.

In some embodiments, the alignment guide 130 may be adjustable in or with respect to a fourth direction or plane, which may extend along or correspond to the superior-inferior direction when the alignment guide 130 is positioned on the anterior side of the patient 110 (e.g., when utilized in an ankle arthroplasty). In one such embodiment, the alignment guide 130 may be axially or translatably adjustable at least 10 mm in or along the fourth direction or plane. For example, the alignment guide 130 may be configured to provide about 15 mm of total axial/translational movement/adjustment in the fourth direction or plane.

In some embodiments, the alignment guide 130 may be adjustable in or along a fifth direction or plane, which may extend along or correspond to the medial-lateral direction when the alignment guide 130 is positioned on the anterior side of the patient 110 (e.g., when utilized in an ankle arthroplasty). In one such embodiment, the alignment guide 130 may be axially or translatably adjustable at least 20 mm in or along the fifth direction or plane.

In some embodiments, the alignment guide 130 may be coupled to the patient 110 proximate to the anatomical structure or construct of interest 114. Adjusting 22 the alignment guide 130 such that the laser line or point 138 is aligned with the visual indication 122 of the target member 118, so as to align the guide 130 with the axis X-X, may thereby adjust the position and/or orientation of the laser device 132 (and/or another portion of the alignment guide 130) with respect to the anatomical structure or construct of interest 114. Adjusting 22 the alignment guide 130 to align the guide 130 with the axis X-X may include adjusting a portion of the guide 130 (e.g., a bone resection guide portion, as explained further below) in the medial-lateral and varus-valgus directions (e.g., in the coronal or frontal plane), such as when utilized for/in an ankle arthroplasty.

In some embodiments, in addition to adjusting 22 the guide so that the laser 138 is aligned with the target member 118, the alignment guide 130 may be adjusted in consideration of the anatomical structure or construct of interest 114. For example, the alignment guide 130 may be adjusted such that the guide 130 facilitates bone resection and/or implant implantation in consideration of the configuration of the anatomical structure or construct of interest 114 and/or the implant itself (in addition to alignment of the implant with the axis X-X). In this way, the alignment guide 130 may facilitate, dictate or otherwise determine, at least in part, the implantation of an implant with respect to the axis X-X of the anatomical structure or construct of interest 114 so that the implant is properly aligned with the axis X-X.

In some embodiments, a first portion or aspect 140 of the alignment guide 130 may be configured to removably couple to the patient 110 proximally to the anatomical structure or construct of interest 114 as shown in the exemplary embodiment illustrated in FIGS. 8 and 12-14. The first portion 140 of the alignment guide 130 may be removably coupled to the patient 110 (e.g., bone and/or tissue) via any biocompatible mechanism, such as but not limited to one or more pins, nails, screws or k-wire. For example, as shown in FIGS. 12 and 13, the first portion 140 of the alignment guide 130 may include one or more through-holes configured to accommodate passage of a pin or like member there-through and into bone and/or tissue of the patient 110. The first portion 140 of the alignment guide 130 may be positioned at a proximal end or portion of the alignment guide 130, as shown in FIGS. 8 and 12-14.

In some embodiments, the first portion 140 may be an end portion of the alignment guide 130. For example, as shown in FIGS. 8 and 12-14, the first portion 140 may define or form the proximal end of the guide 130. The laser device 132 may be coupled to a differing portion of the guide 130 than the first portion which can be physically, selectively adjusted with respect to the first portion 140. As the first portion 140 is coupled to the patient 110, the laser device 132 may thereby also be physically, selectively adjusted with respect to the patient 110 (e.g., the at least one anatomical structure or construct of interest 114).

For example, as shown in FIGS. 8 and 12-14, the alignment guide 130 may include a second portion or aspect 142 movably coupled to the first portion 140. The first and second portions 140, 142 may allow adjustability therebetween (i.e., selective relative movement) along at least one degree of freedom. As the first portion 140 may be fixed or coupled to the patient 110, the second portion 142 may thereby be adjusted or moved with respect to the first portion 140 and patient 110.

In some embodiments, the first and second portions 140, 142 may be pivotably coupled about an axis to allow selective relative angular adjustment between therebetween. For example, as shown in FIGS. 8 and 12-14, the first and second portions 140, 142 of the guide 130 may be pivotably coupled such that relative angular movement therebetween along or in the sagittal plane (i.e., anterior-posterior slope) may be adjusted or selected when the alignment guide 130 is positioned on the anterior side of the patient 110 (e.g., when utilized in an ankle arthroplasty). Such angular adjustment in the sagittal plane may be selected in consideration of the anatomical structure or construct 114, such as in consideration of bone resection via the guide 130. For example, with respect to an ankle arthroplasty, the angular adjustment of the second portion 142 with respect to the first portion 140 in the sagittal plane may be selected to ensure proper resection of a distal portion of the tibia (and/or proper resection of a proximate portion of the talus), such as to form the resected surface(s) are substantially perpendicular to the axis of the respective bone(s) and/or the axis X-X.

As also shown in FIGS. 8 and 12-14, the alignment guide 130 may further include a third portion or aspect 144 movably coupled to the second portion 142. The third and second portions 144, 142 may allow adjustability therebetween (i.e., selective relative movement) along at least one degree of freedom. As the first portion 140 may be fixed or coupled to the patient 110, the third portion 142 may also be adjusted or moved with respect to the first portion 140 and the patient 110. In some embodiments, the third and second portions 144, 142 may be translatably coupled along an axis to allow selective relative linear or axial adjustment therebetween. For example, as shown in FIGS. 8 and 12-14, the third and second portions 144, 142 of the guide 130 may be translatably coupled such that relative movement therebetween along or in the proximal-distal or dorsal-plantar direction may be adjusted or selected when the alignment guide 130 is positioned on the anterior side of the patient 110 (e.g., when utilized in an ankle arthroplasty). In some embodiments, the third and second portions 144, 142 may be rotatably coupled along an axis to allow selective relative angular or rotational adjustment therebetween (potentially in addition to the axial proximal-distal adjustment). For example, as shown in FIGS. 8 and 12-14, the second and third portions 142, 144 of the guide 130 may be rotatably coupled such that relative movement therebetween in or along the transverse plane may be adjusted or selected when the alignment guide 130 is positioned on the anterior side of the patient 110 (e.g., when utilized in an ankle arthroplasty).

Such axial adjustment along the proximal-distal direction and/or rotational adjustment in the transverse plane may be selected to align the laser 138 with the target member 118 (and thereby the guide along the axis X-X and/or in consideration of the anatomical structure or construct 114, such as in consideration of bone resection via the guide 130. For example, with respect to an ankle arthroplasty, the proximal-distal adjustment and/or rotational adjustment in the transverse plane of the third portion 144 with respect to the first and second portions 140, 142 may be selected to ensure proper resection of a distal portion of the tibia (and/or proper resection of a proximate portion of the talus), such as to form the resected surface(s) form a proper amount of space for an ankle implant.

The alignment guide 130 may further include a fourth portion or aspect 146 movably coupled to the third portion 144, as shown in FIGS. 8 and 12-14. The third and fourth portions 144, 146 may allow adjustability therebetween (i.e., selective relative movement) along at least one degree of freedom. As the first portion 140 may be fixed or coupled to the patient 110, the fourth portion 146 may thereby also be adjusted or moved with respect to the first portion 140 and the patient 110. In some embodiments, the third and fourth portions 144, 146 may be translatably coupled along an axis to allow selective relative linear or axial adjustment therebetween. For example, as shown in FIGS. 8 and 12-14, the third and fourth portions 144, 146 of the guide 130 may be translatably coupled such that relative movement therebetween along or in the medial-lateral direction may be adjusted or selected when the alignment guide 130 is positioned on the anterior side of the patient 110 (e.g., when utilized in an ankle arthroplasty). Such axial adjustment along the medial-lateral direction may be selected to align the laser 138 with the target member 118 (and thereby the guide along the axis X-X), and potentially in consideration of the at least one anatomical structure or construct of interest 114 (such as in consideration of bone resection via the guide 130). For example, with respect to an ankle arthroplasty, the medial-lateral adjustment of the fourth portion 146 with respect to the third portion 144 (and the first and second portions 140, 142 and the patient 110) may be selected to align the guide 130 to the axis X-X to ensure proper resection of a distal portion of the tibia (and/or proper resection of a proximate portion of the talus), such as to ensure an ankle implant is centered on, and/or oriented such that the coronal plane of the ankle joint is aligned with, the axis X-X and/or fully engages the bone(s).

The guide 130 may also be configured to provide varus-valgus adjustment when the alignment guide 130 is positioned on the anterior side of the patient 110 (e.g., when utilized in an ankle arthroplasty). For example, a pin or like member may be inserted into the patient (e.g., into the distal tibia with respect to an ankle arthroplasty) at a specified distance from the anatomical structure or construct of interest 114 (e.g., along or adjacent to the tibial crest with respect to an ankle arthroplasty). The guide 130 may be passed over the pin member through an aperture extending though the guide 130 (e.g., a central aperture of the first portion 140 as shown in FIG. 12). The guide 130 (e.g., a distal portion thereof) may be rotated (e.g., coronal rotation) about the pin member to adjust the guide 130 along the varus-valgus direction. Once the varus/valgus alignment adjustment is made, a second and/or third pin member may be positioned through additional apertures of the guide 130 and into the patient to fix or lock the guide 130 in varus/valgus rotation. In some other embodiments, the guide 130 may be configured to provide adjustment (e.g., mechanically) or relative movement between at least two portions of the first, second, third and fourth portions 140, 142, 144, 146 along the varus-valgus direction.

Such varus/valgus adjustment may be selected to align the laser 138 with the target member 118 (and thereby the guide along the axis X-X), and potentially in consideration of the at least one anatomical structure or construct of interest 114 (such as in consideration of bone resection via the guide 130). For example, with respect to an ankle arthroplasty, the varus/valgus adjustment of the guide 130 as a whole (e.g., about an axis defined by a pin member or the like) or at least one portion thereof may be selected to align the guide 130 to the axis X-X to ensure proper resection of a distal portion of the tibia (and/or proper resection of a proximate portion of the talus), such as to ensure an ankle implant is centered on, and/or oriented such that the coronal plane of the ankle joint is aligned with, the axis X-X and/or fully engages the bone(s).

As discussed above, the alignment guide 130 may facilitate implantation of an implant by facilitating bone and/or tissue resection at the at least one anatomical structure or construct of interest 114. For example, as shown in FIGS. 12-14, the guide 130 may include a resection guide 148. The resection guide 148 may be configured to facilitate resection of the at least one anatomical structure or construct of interest 114. In some embodiments, the resection guide 148 may be configured to facilitate resection one or more bones. In some embodiments, the resection guide 148 may include at least one slot configured to facilitate resection one or more bones via a cutting implement, as shown in FIGS. 12-14.

The resection guide 148 may be fixedly coupled or removably coupled with the guide 130. In some embodiments, the resection guide 148 may be removably coupled to the fourth portion 146, as shown in FIGS. 12-14. The resection guide 148 may couple via the same mechanism as the laser device 132 couples to the guide 130. In this way, the laser device 132 may be de-coupled from the guide 130, and then the resection guide 148 may be coupled to the guide 130 at the same location. In other embodiments, the resection guide 148 may be coupled to the guide 130 via a differing mechanism and/or location as compared to the laser device 132.

The alignment guide 130 may be adjusted such that the laser 138 as projected by the laser device 132 is aligned with the target member 118, as described above. In such a configuration or orientation, the resection guide 148 may be coupled to the alignment guide 130 (if not already coupled), and the alignment guide 130 may be configured such that the resection guide 148 is aligned with the axis X-X of the anatomical structure or construct of interest 114. The alignment guide 130 may then be further adjusted such that the resection guide 148 is properly positioned with respect to the anatomical structure or construct of interest 114 to facilitate resection thereof. The alignment guide 130 may thereby be adjusted, in totality, such that the resection guide 148 is aligned with the axis X-X and positioned/orientated for proper resection of the anatomical structure or construct of interest 114 in consideration of (or with respect to) an implant for use with the anatomical structure or construct of interest 114. For example, with respect to an ankle arthroplasty, the alignment guide 130 may be adjusted such that the resection guide 148 is aligned with the axis X-X and positioned/orientated for proper resection of the distal tibia and/or proximal talus (e.g., in consideration of an ankle implant).

In some embodiments, the alignment guide 130 may be adjusted, in totality, with respect to the anatomical structure or construct of interest 114 so that when the anatomical structure or construct of interest 114 is resected via the resection guide 148, at least one resected surface thereof is aligned with and/or oriented normal or perpendicular to the axis X-X, and properly positioned/orientated with respect to a particular implant. In some such embodiments the alignment guide 130 may be adjusted so that when the anatomical structure or construct of interest 114 is resected via the resection guide 148, at least one resected surface thereof and/or an engagement surface of an implant that engages with at least one resected surface is aligned with, and/or is oriented normal or perpendicular to, the axis X-X. For example, as shown FIGS. 15-18, an implant 150 may include at least one engagement surface 152 configured to engage at least one corresponding resected portion of the anatomical structure or construct of interest 114. In such embodiments, the alignment guide 130 may be configured and adjusted so that when the anatomical structure or construct of interest 114 is resected via the resection guide 148, at least one resected surface and at least one engagement surface 152 of the implant 150 (when the engagement surface 152 of the implant 150 engages at least one resected surface) are substantially centered on, and/or are normal or perpendicular to, the axis X-X.

When the axis X-X is the mechanical axis of the patient's 110 lower extremity or leg, the mechanical forces acting through the lower extremity are thereby substantially centered and properly loaded on at least one engagement surface 152 of the implant 150 (and may thereby be substantially uniformly applied to at least one resected surface and/or at least one engagement surface 152). For example, with respect to an ankle arthroplasty, the alignment guide 130 may be configured and adjusted so that when the tibia and/or talus is resected via the resection guide 148, at least one resected surface and the engagement surface 152 of the ankle implant 150 (when the engagement surface 152 of the implant 150 engages the resected surface) are substantially centered on, and/or are normal or perpendicular to, the axis X-X (which may correspond to the mechanical axis of the patient's lower extremity).

It is noted that the implant 150 may include at least one articulation and/or bearing surface, and such surfaces may be substantially aligned or centered with respect to the engagement surface 152. In this way, at least one articulation and/or bearing surface of the implant 150 may also be substantially centered and/or aligned with, and/or are normal or perpendicular to, the axis X-X.

The laser generating and/or projecting device 136 may project a laser light plane 138 that is in the visible spectrum (e.g., within the range of about 430 nm to about 630 nm, or about 480 nm to about 580 nm, or about 500 nm to about 560 nm), as shown in FIGS. 10 and 11. In some embodiments, the laser generating and/or projecting device 136 may be configured to project a laser light plane 138 that emanates in a fan shape, as shown in FIGS. 10 and 11. The portion of the laser light 138 that is incident on the patient 110, sterility barrier 120 and target member 118 may thereby form a laser light line. In some embodiments, the guide 130 and laser device 132 may be configured such that when the guide 130 is attached to the patient 110 in a coronal plane, the laser light plane 138 extends perpendicular thereto along a sagittal plane. In some embodiments, the laser device 132 may be configured to emit a fan shaped laser light plane 138 with a fan angle within the range of about 1 degree to about 75 degrees (e.g., 1, 5, 10, 20, 30, 45, 60 or 75 degrees). In some embodiments, the laser device 132 may be configured to emit a fan shaped laser light plane 138 with a fan angle of about 60 degrees. In some embodiments, the laser device 132 may be configured to emit a laser light plane 138 with a beam angle of less than 3 rad. In alternative embodiments, the laser light 138 may emanate as a laser line (i.e., the incident light may form a point or dot).

In some embodiments, in addition to emitting a linear laser line 138 (via a fan shaped laser light plane), the laser device 132 may be configured to emit at least one secondary linear laser line (shot shown) (e.g., via a fan shaped laser light plane), which may be orientated perpendicular to the linear laser line 138. The secondary linear laser line may further assist the user in properly orienting the guide 130 with respect to the anatomical configuration/structures of the patient (e.g., to the alignment axis (e.g., an anatomical or mechanical axis) of the anatomical configuration/structures of interest).

In some embodiments, the implant alignment and guide system and method 10 may include a laser line reference member or device (not shown) for use with the laser line 138 (and at least one secondary linear laser line, if provided). The reference member is configured such that the laser line 138 (and at least one secondary linear laser line, if provided) is projected thereon, and include visual reference indications. The reference member may be affixed to the patient (directly or indirectly) such that the position and orientation of the reference guide is not affected by adjustment of the guide 130 (i.e., the position and orientation of the reference guide is not adjusted via adjustment of the guide 130).

The visual reference indications on the reference member may include a plurality of lines or markings configured to form a calibrated index, goniometer, level indicator or the like to provide a quantified indication of the position and/or orientation adjustments of the laser device 132 of the implant alignment and guide system and method 10. For example, the plurality of lines or markings of the reference member may be utilized by a user to provide a quantified indication of an amount (e.g., angular (e.g., degrees) and/or linear measurement) of adjustment the guide 130 is given to align the laser device 132 (and thereby the guide 130 itself) with respect to a target indication. As another example, the plurality of lines or markings of the reference member may be utilized by a user to provide a quantified indication of an amount (e.g., angular (e.g., degrees) and/or linear measurement) of adjustment the guide 130 is given to offset the laser device 132 (and thereby the guide 130 itself) with respect to a target indication.

The laser generating and/or projecting device 136 of the laser device 132 may be any device that emits a laser light plane or line 138 that is clearly visible (to humans under typical operating lighting conditions) when incident at least on the target indication surface 121 and/or the visual indication 122 of the target member 118 in an operating room setting (e.g., a room with illuminance of within the range of about 40,000 to about 160,000 lux). In some embodiments, the laser device 132 may be configured such to project the laser light 138 with a top-hat substantially uniform non-Gaussian line intensity profile along the line length. In some embodiments, the laser device 132 may be configured such to project the laser light 138 with Gaussian line intensity profile along the line length (e.g., via a cylindrical lens).

In some embodiments, the laser device 132 may be configured such that the projected laser light 138 visually convey alignment (e.g., rotational alignment about the sagittal plane) of the guide 130 within about 2 degrees of the axis X-X identified by the visual indication 122. In some embodiments, the laser device 132 may be configured to emit laser light 138 with a straightness of less than or equal to about 0.1%, and/or a relative intensity floor of at least 50%. In some embodiments, the laser device 132 may be configured with a beam quality of less than 1.5 $m^2$.

In some embodiments, the laser device 132 may produce a laser output power of no more than 100 mW. In some embodiments, the laser device 132 may be configured to maintain an enclosure leakage current of less than 0.1 mA when its circuit is normally closed. In some embodiments, the laser device 132 may be configured to maintain normal working conditions after gamma sterilization thereof (e.g., sterilization of at least a 25 kGy sterilization dose that achieves at least SAL of $10^{-6}$ (per ISO 11157)). In some embodiments, the laser device 132 may be configured with at least level 4 ESD protection (e.g., meet the IEC 61000-4-2 standard). In some embodiments, the laser device 132 may be configured according to IEC 60601-1 standards for electrical safety for medical devices.

Figure 19:
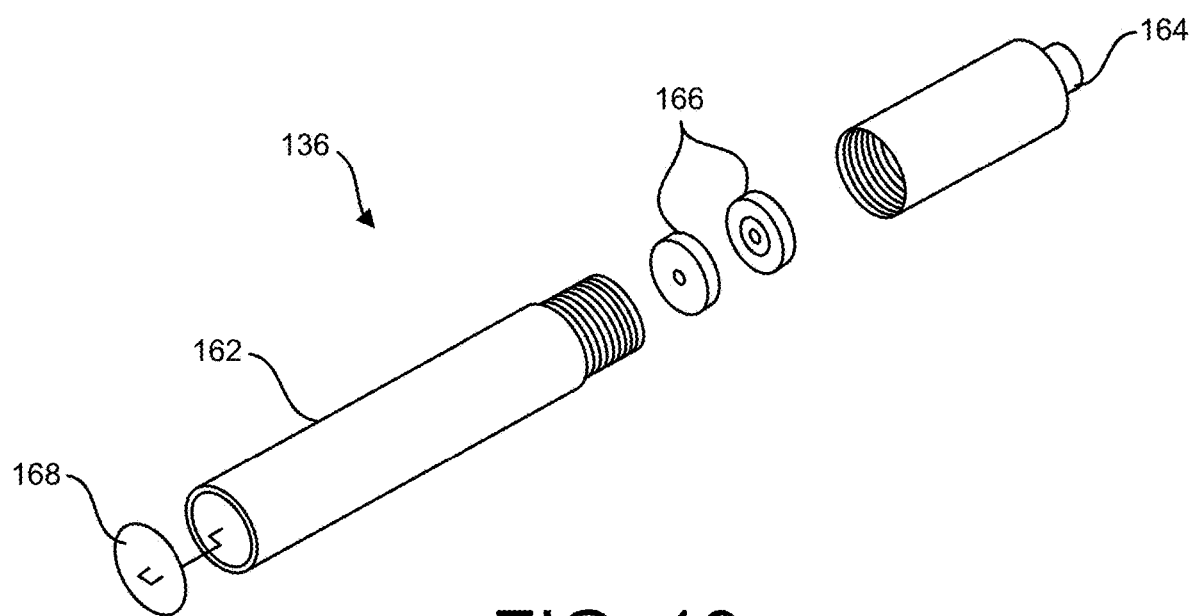
FIG. 19 illustrates a perspective exploded view of an exemplary laser device according to an alignment system and method according to the present disclosure.
Figure 20:
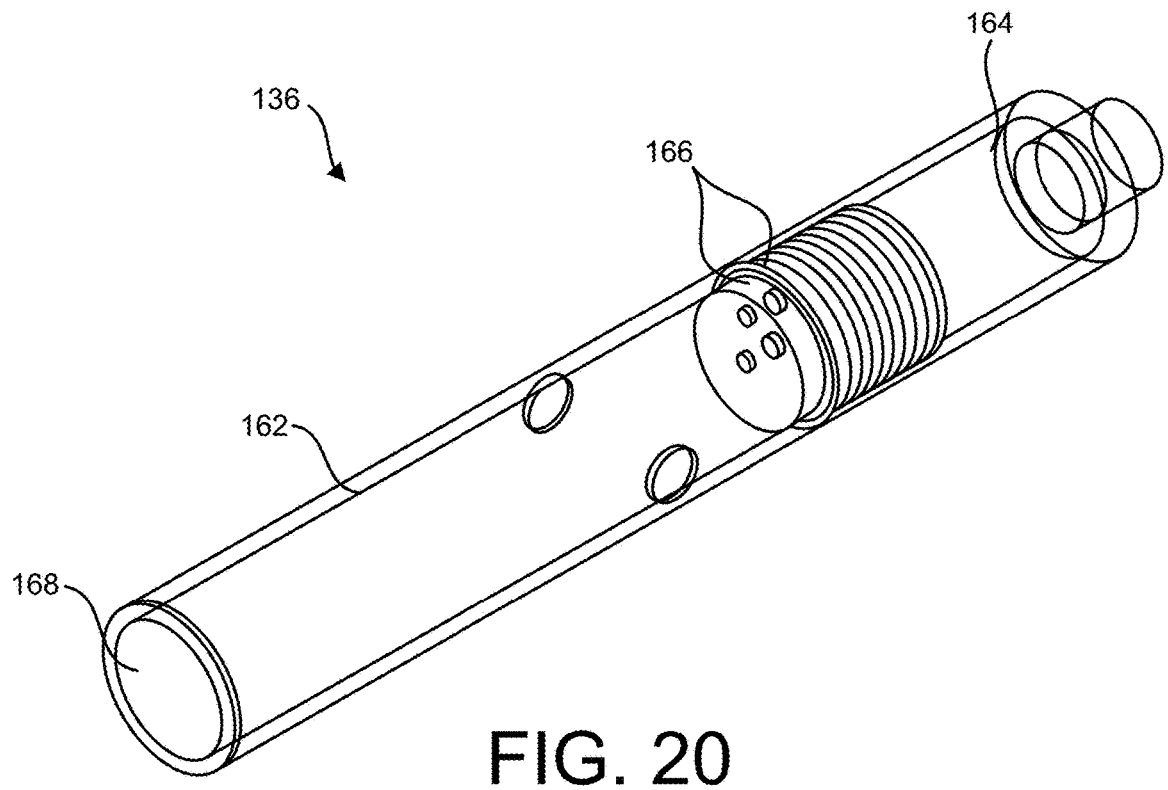
FIG. 20 illustrates an elevational perspective view of an exemplary laser device according to FIG. 19.
Figure 21:
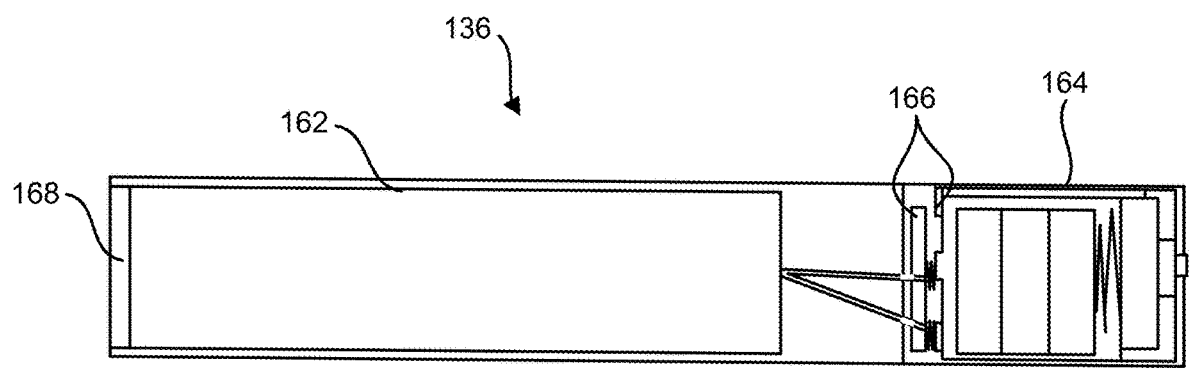
FIG. 21 illustrates a side cross-sectional perspective view of an exemplary laser device according to FIG. 19.

As shown in FIGS. 19-21, in one exemplary embodiments the laser device 132 may include a laser line module 162, a power source and switch module 164, at least one contact member 166 and a front cover 168. The laser line module 162 may be configured to mate with the power source and switch module 164 with the at least one contact member 166 positioned electrically therebetween. The power source and switch module 164 may be configured to store electrical power, and selectively provide the electrical power to the laser line module 162 via at least one contact member 166 when a switch of the module 164 is activated. When electrically powered, the laser line module 162 may be configured to emit the laser line 138 through the front cover 168. The front cover 168 may thereby be substantially transparent with respect to the laser line 138. However, in other embodiments the laser device 132 may be configured differently than illustrated in FIGS. 19-21.

Figure 22:
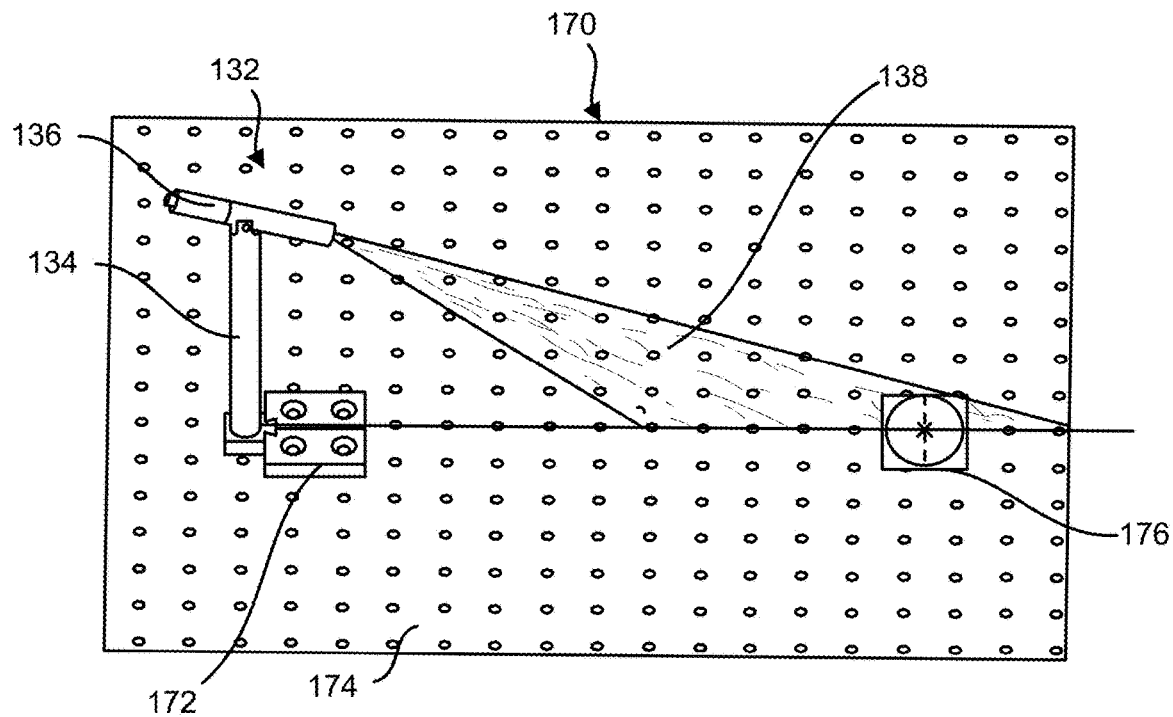
FIG. 22 illustrates a system and method of calibrating the laser device of FIG. 19.

In some embodiments, the laser-based implant alignment or guidance systems and methods of the present disclosure may include a calibration system for performing an accuracy test, and potentially a re-calibration, of the implant alignment guide 130. In some embodiments, as shown in FIG. 22, a calibration system 170 for the implant alignment guide 130 may include a calibration block 172 that couples (either fixedly or removably couples) to the calibration member 174. The calibration block 172 may couple to the calibration member 174 (e.g., via pre-formed apertures) in a predetermined fixed orientation with respect to a calibration target 176, such as the laser target 118 or a replica thereof discussed above, as shown in FIG. 22. The calibration system 170 may be configured such that when the calibration block 172 is coupled to the calibration member 174 in a predetermined fixed orientation with respect to a calibration target 176, and a properly calibrated laser device 132 is coupled to the calibration block 172 at a predetermined positioned and orientation (e.g., provided by the mechanical coupling thereof), the laser line 138 projected by the properly calibrated laser device 132 will be incident on the center or indication of the calibration target 176, as shown in FIG. 22.

In some embodiments, to facilitate determination of alignment and/or calibration of the laser device 132, the target indication surface of the calibration target 176 (e.g., target member 118 as shown in FIG. 5) may include at least one visual axis indication that passes through an indication of the center or other indication of the location of the axis X-X of the anatomical structure of interest of the calibration target 176, as shown in FIG. 22. The calibration target 176 may thereby be coupled to the calibration member 174 in an orientation with respect to the calibration block 172 and laser device 132 such that a properly calibrated laser device 132 would project a laser light pattern 138 that extends along the visual axis indication (and through the indication of the location of the axis X-X of the anatomical structure of interest), as shown in FIG. 22.

If the laser line 138 projected by the laser device 132 is not incident on the center or indication of the location of the axis X-X of the anatomical structure of interest (and thereby does not extend along the visual axis indication) of the calibration target 176, then the laser device 132 is not properly calibrated for use with the guide 130. As noted above, the visual axis indication of the calibration target 176 may be utilized to determine the degree and/or nature of misalignment. For example, the calibration system 170 system may be configured to ensure that when the laser device 132 is coupled to the guide 130 and the guide is oriented along a coronal plane, the laser line 138 projected by the laser device 132 extends along a sagittal plane. The calibration system 170 system may also be configured to ensure that when the laser device 132 is coupled to the guide 130 and the guide is coupled to the patient 110, the laser line 138 projected by the laser device 132 is incident on the laser target member 118.

Figure 23:
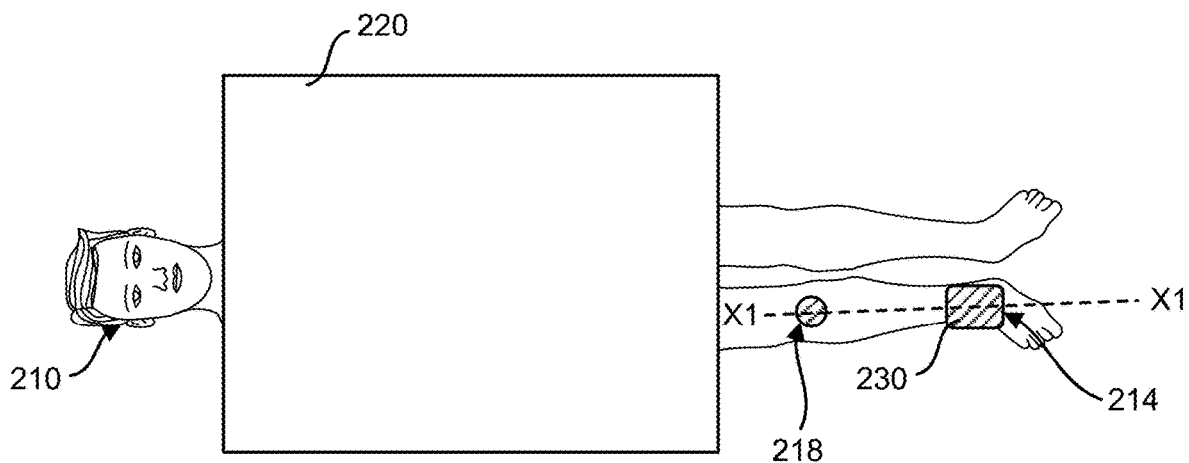
FIG. 23 illustrates an alternative implant alignment and guide method utilizing an alternative laser-based implant alignment system according to the present disclosure.

FIG. 23 illustrates another exemplary laser-based implant alignment or guidance system and method according to the present disclosure. The exemplary laser-based implant alignment and guide method and system of FIG. 23 is substantially similar to the exemplary laser-based implant alignment and guide methods 10 and systems described above with respect to FIGS. 1-22, and therefore like reference numerals preceded by the numeral "2" are used to indicate like elements, aspects, functions, actions, configurations and the like. The laser-based implant alignment system and method of FIG. 23 may include any of the elements, aspects, functions, actions, configurations and the like of the laser-based implant alignment systems and methods 10 of FIGS. 1-22. The description above with respect to the laser-based implant alignment systems and methods 10 of FIGS. 1-22 thereby equally applies to the exemplary laser-based implant alignment system and method of FIG. 23, including description regarding alternative embodiments thereto (i.e., modifications, variations or the like). The exemplary laser-based implant alignment system and method of FIG. 23 differs from the exemplary laser-based implant alignment and guide methods 10 and systems of FIGS. 1-22 with respect to the attachment and positioning of the target member 218.

As shown in FIG. 23, the laser-based implant alignment system and methods of the present disclosure may be utilized with respect to any axis X1-X1 of the anatomical structure of interest 214. For example, as shown in FIG. 23, with respect to a lower extremity, the target member 218 (and potentially the target base (not shown)) may be coupled to the exterior of the patient 210 at, or in substantial alignment with, an anatomical axis and/or a mechanical axis of or associated with the anatomical structure of interest 214. For example, with respect to an ankle arthroplasty, the target member 218 (and potentially the target base (not shown)) may be non-invasively coupled to the patient 210 at, or in substantial alignment with, the center of the patient's tibia tubercle so that the target member 218 is substantially aligned with the anatomical axis and/or the mechanical axis X1-X1 of the patient's tibia (as opposed to in alignment with the center of the femoral head of the femur, and thereby the mechanical axis X-X of the patient's leg as shown in FIGS. 2, 4, 7 and 10 and described above) with the alignment guide 230 invasively-coupled to the distal tibia and/or the talus, as shown in FIG. 23. As also shown in FIG. 23, in such an embodiment the sterility barrier 220 may not extend to such a location of the patient, and thereby the target member 218 may be directly, removably coupled or attached to the exterior of the patient 210 (i.e., a target base (not shown) may not be utilized). In some other embodiments, a target base (not shown) may be removably coupled or attached to the exterior of the patient 210, and the target member 218 may couple thereto (potentially through or over the sterility barrier 220, as discussed above).

Figure 24:
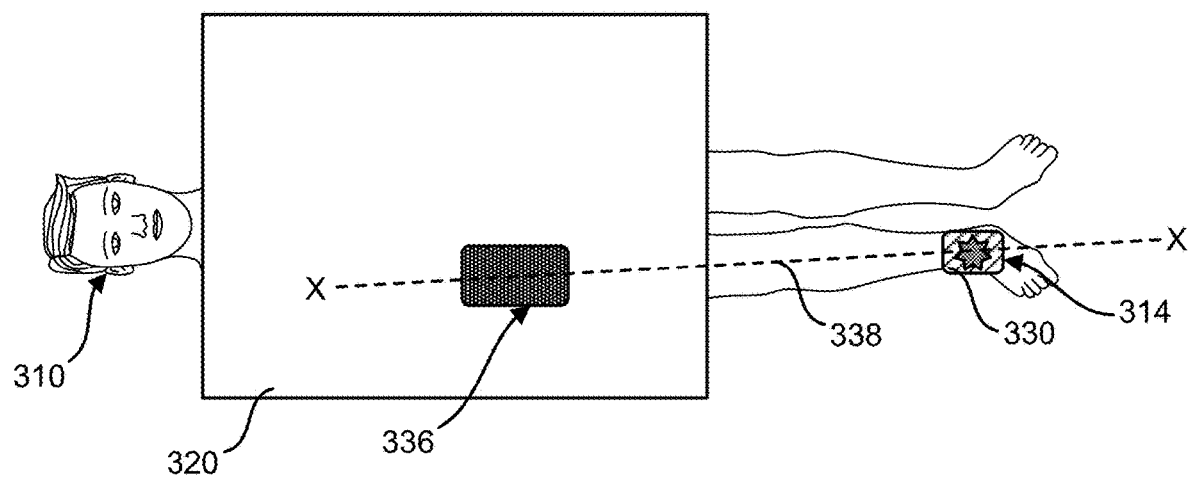
FIG. 24 illustrates another alternative implant alignment and guide method utilizing another alternative laser-based implant alignment system according to the present disclosure.
Figure 25:
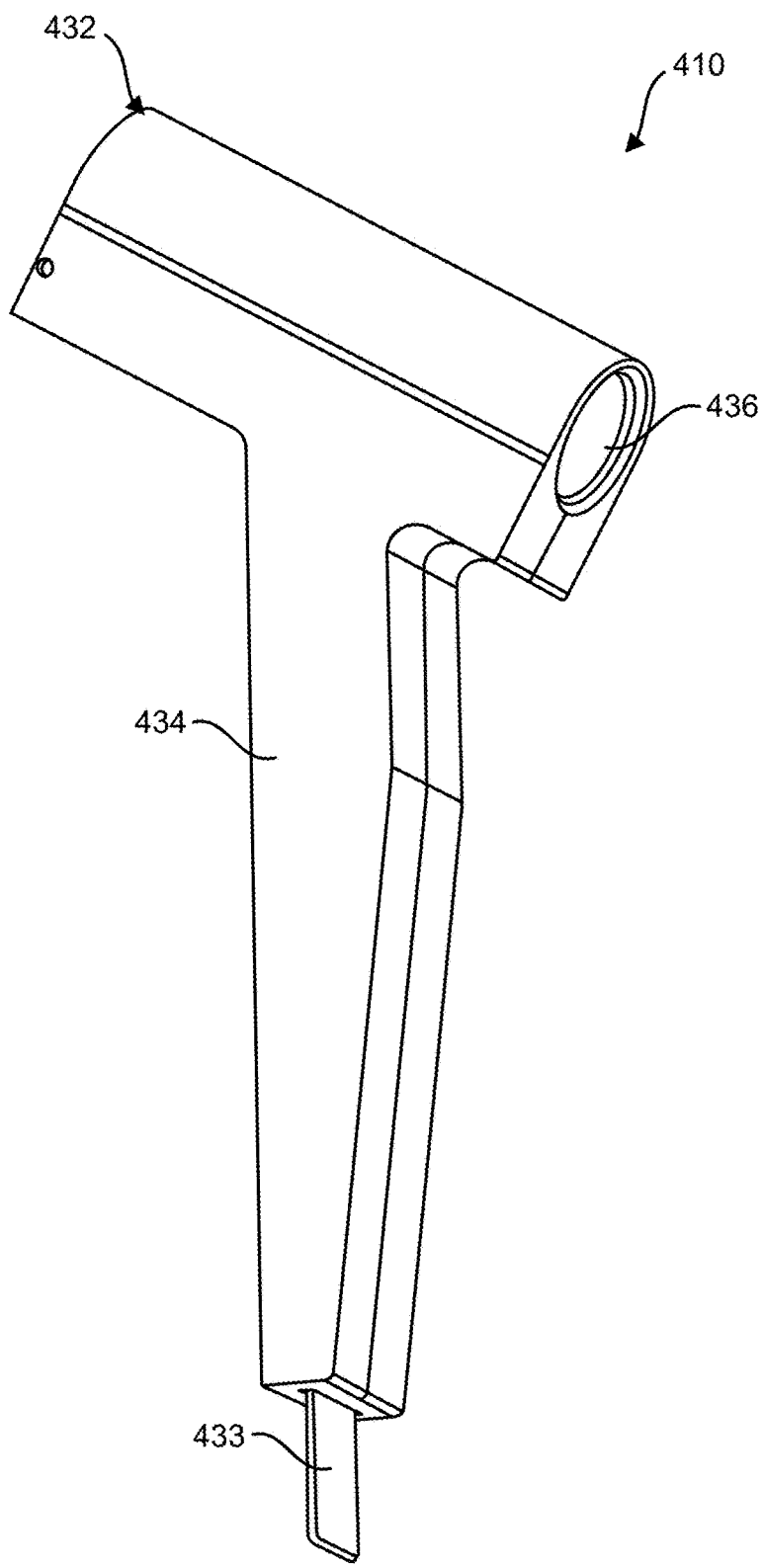
FIG. 25 illustrates a bottom perspective view of another exemplary embodiment of a laser device of a laser-based implant alignment system according to the present disclosure.
Figure 26:
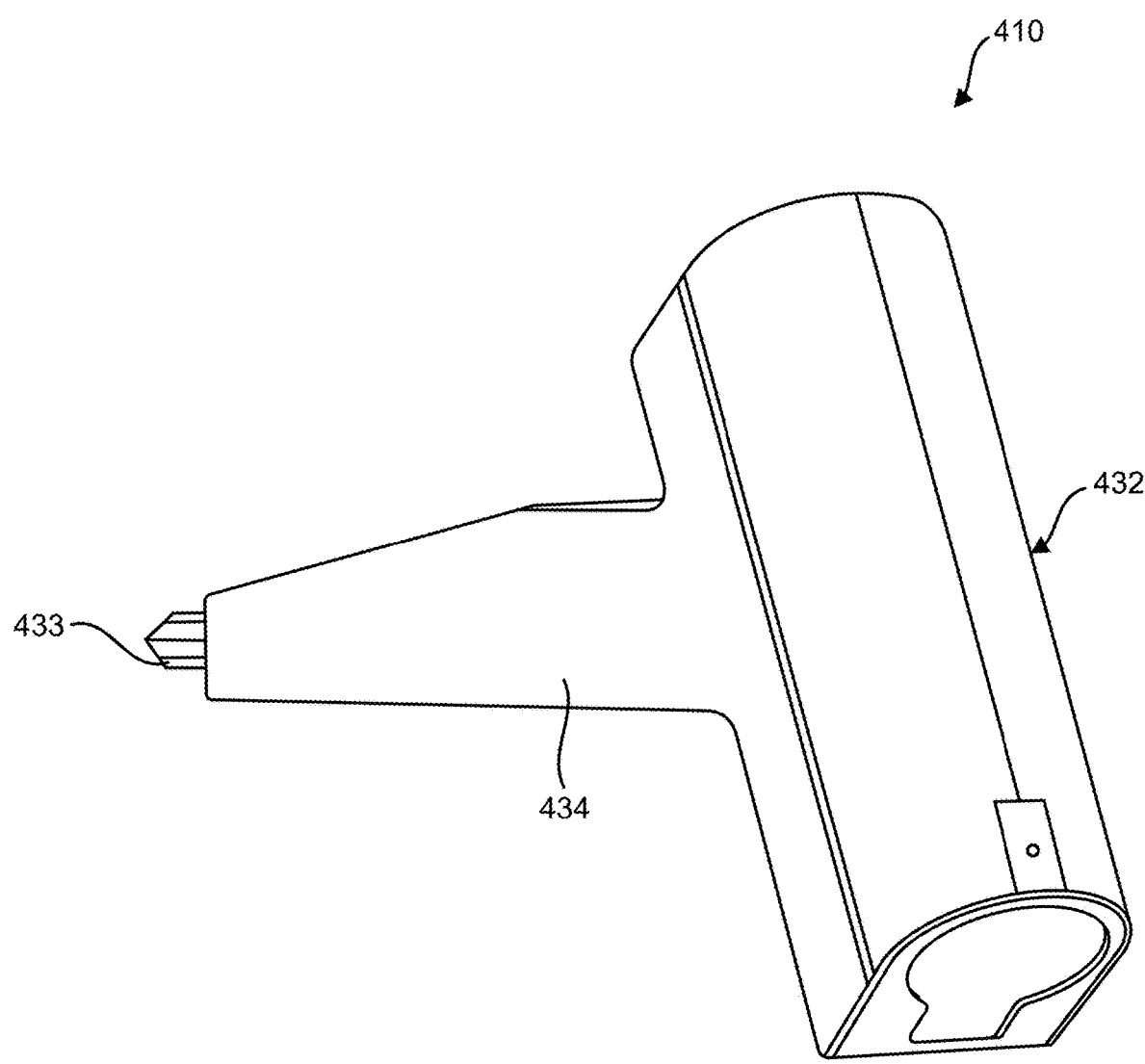
FIG. 26 illustrates an elevational perspective view of the laser device of FIG. 25.

FIG. 24 illustrates another exemplary laser-based implant alignment or guidance system and method according to the present disclosure. The exemplary laser-based implant alignment and guide method and system of FIG. 24 is substantially similar to the exemplary laser-based implant alignment and guide methods 10 and systems described above with respect to FIGS. 1-22 and the exemplary laser-based implant alignment and guide method and system described above with respect to FIG. 23, and therefore like reference numerals preceded by the numeral "3" are used to indicate like elements, aspects, functions, actions, configurations and the like. The laser-based implant alignment system and method of FIG. 24 may include any of the elements, aspects, functions, actions, configurations and the like of the laser-based implant alignment systems and methods 10 of FIGS. 1-22 and the laser-based implant alignment and guide method and system described above with respect to FIG. 23. The description above with respect to the laser-based implant alignment systems and methods 10 of FIGS. 1-22 and the laser-based implant alignment and guide method and system described above with respect to FIG. 23 thereby equally applies to the exemplary laser-based implant alignment system and method of FIG. 24, including description regarding alternative embodiments thereto (i.e., modifications, variations or the like). The exemplary laser-based implant alignment system and method of FIG. 24 differs from the laser-based implant alignment and guide methods 10 and systems of FIGS. 1-22 and the laser-based implant alignment and guide method and system described above with respect to FIG. 23 with respect to the attachment, positioning and use of the alignment guide 330 and the laser device 332.

As shown in FIG. 24, in some embodiments a laser device 332 may be removably coupled to an exterior of the patient 310 (i.e., non-invasively coupled) along an axis X-X of, or associated with, an anatomical structure of interest 314 in a spaced relationship therefrom. For example, with respect to an ankle arthroplasty, the laser device 332 may be coupled to patient 310 at or in alignment with the patient's femoral head, as shown in FIG. 24. The laser device 332 may be directly coupled to the exterior of the patient 310, or indirectly couple via at least one intervening member (not shown). For example, as discussed above with respect to FIGS. 3-6, at least one base member (not shown) may be directly coupled to the patient's skin, and a sterility barrier 320 may extend thereover. The laser device 332 may thereby couple with the at least one base member through or over the sterility barrier 320, as shown in FIG. 24.

The laser device 332 may be configured to emit a laser light line or plane 338 towards the anatomical structure of interest 314, as shown in FIG. 24. The laser device 332 and/or its attachment mechanism (e.g., at least base member) may be configured such that the projected laser light 338 is aligned with the axis X-X associated with the anatomical structure of interest 314. In some embodiments, the laser device 332 may be adjustable such that the direction and/or orientation of the projected laser light 338 is selectively changed and brought into alignment with the axis X-X (if not already aligned). In some embodiments, the laser device 332 may be manually aligned with the axis X-X via visual inspection. A user may adjust the laser device 332 so that the laser light 338 is aligned with the axis X-X based on visually inspecting the laser light 338 and its projection on or about the anatomical structure of interest 314. For example, with respect to an ankle arthroplasty, the laser device 332 may be manually adjusted so that the laser light 338 is aligned with the axis X-X based on visually inspecting the laser light 338 incident on the resected ankle joint (i.e., the distal tibia and/or talus).

As another example with respect to an ankle arthroplasty, the laser device 332 may be manually adjusted so that the laser light 338 is aligned with the axis X-X based on visually inspecting the laser light 338 incident on the alignment guide 330 that is coupled to the ankle joint (e.g., coupled to the distal tibia and/or talus, which may be resected). In such an embodiment, the alignment guide 330 may include a visual indication that can be aligned with the incident laser light 338 and thereby position and orient the alignment guide 330 in a neutral state such that the alignment guide 330 can be used to facilitate bone resection and/or implant implantation so that the implant is aligned with the axis X-X, as described above. Further, as also described above, the alignment guide 330 may be adjusted in consideration of the configuration of the anatomical structure or construct of interest 314 and/or the implant itself (in addition to alignment of the implant with the axis X-X) to facilitate proper or desired bone resection and/or implant implantation.

FIGS. 25-36 illustrate another exemplary implant alignment or guidance system and method according to the present disclosure. The exemplary implant alignment and guide method and system 410 of FIGS. 25-36 is substantially similar to the exemplary implant alignment and guide method and system 10 described above with respect to FIGS. 1-22, the exemplary implant alignment and guide method and system described above with respect to FIG. 23 and the exemplary implant alignment and guide method and system described above with respect to FIG. 24, and therefore like reference numerals preceded by the numeral "4" are used to indicate like elements, aspects, functions, actions, configurations and the like. The implant alignment and guide system and method 410 of FIGS. 25-36 may include any of the elements, aspects, functions, actions, configurations and the like of the implant alignment and guide system and method 10 of FIGS. 1-22, the implant alignment and guide method and system described above with respect to FIG. 23 and/or the implant alignment and guide method and system described above with respect to FIG. 24. The description above with respect to the implant alignment and guide system and method 10 of FIGS. 1-22, the implant alignment and guide method and system described above with respect to FIG. 23 and/or the implant alignment and guide method and system described above with respect to FIG. 24 thereby equally applies to the exemplary implant alignment system and method of FIGS. 25-36, including description regarding alternative embodiments thereto (i.e., modifications, variations or the like).

As shown in FIGS. 25-28, 32 and 33, the exemplary implant alignment system and method 410 includes a laser device 432. The laser device 432 includes tang, tab or projection portion 433 with an electrical switch 465, at a bottom end that is configured to removably, but securely, fit within a slot or aperture 431 of a guide block 430 of the system 410, as shown on FIGS. 27, 28 and 33. As shown on FIG. 27, the laser device 432 may include a housing or support 434 that extends from the tang 433 that contains and physically supports a power source 464 and a laser line module 436. In some embodiments, the housing 434 and the tang 433 may be integral. The housing 434 may rigidly support the laser line module 436 with respect to the tang 433 such that the laser light 438 emitted therefrom is orientated at a fixed angle and orientation with respect to the tang portion 433. The power source 464 may be configured to store electrical power, and selectively provide the electrical power to the laser line module 436 when a switch 465 is activated.

Figure 27:
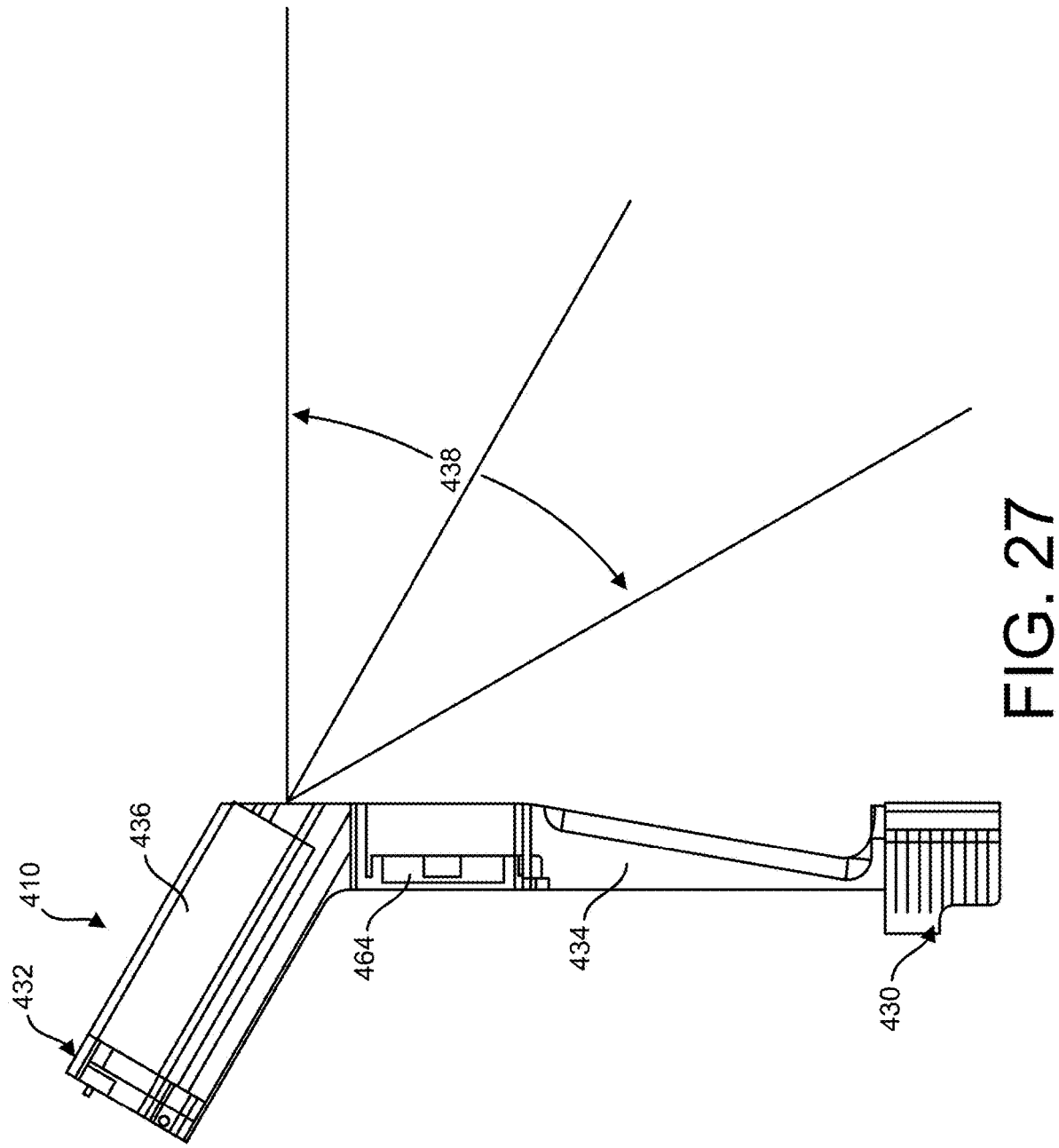
FIG. 27 illustrates a side view of the laser device of FIG. 25 with internal components visible and engaged with an exemplary guide block of the laser-based implant alignment system.
Figure 28:
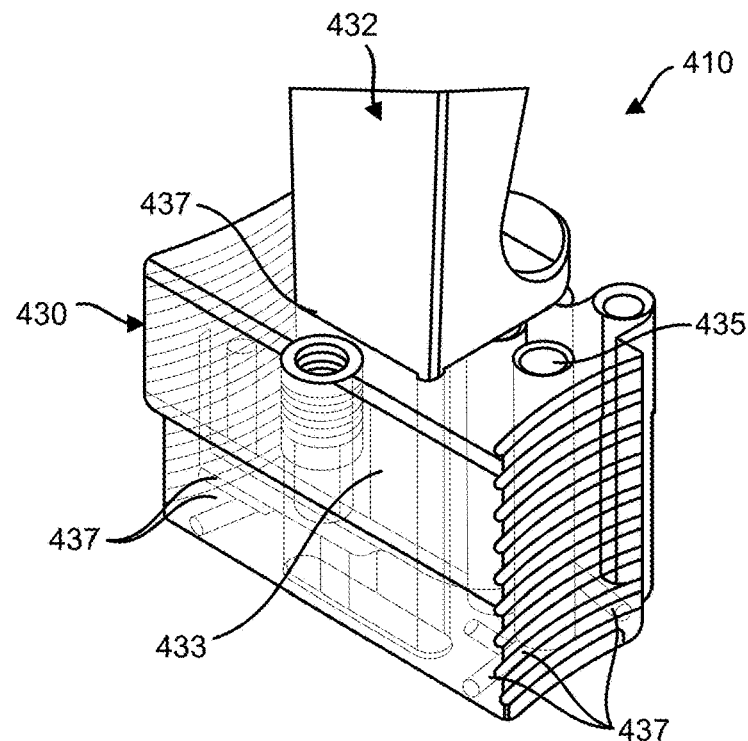
FIG. 28 illustrates an elevational perspective view of a tang portion of the laser device of FIG. 25 mated within the guide block of FIG. 27.
Figure 33:
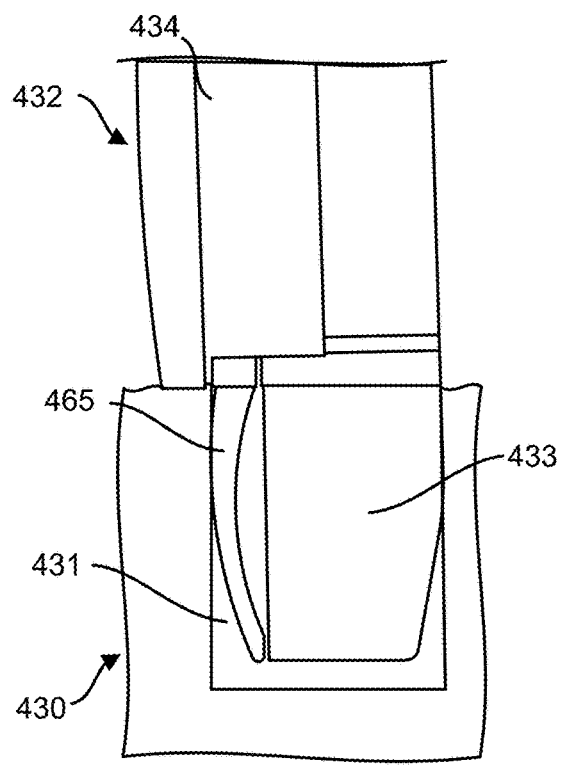
FIG. 33 illustrates a top view of the tang portion of the laser device of FIG. 25 positioned within a slot of the guide block and with the switch thereof in an activated state.

The tang portion 433 of the laser device 432 may be configured such that the laser device 432 can be securely removably or selectively coupled within the slot 431 of the guide block 430, as shown on FIGS. 27, 28 and 33. In some embodiments, the tang portion 433 and the slot 431 may securely couple via a friction fit. In some embodiments, the tang portion 433 may narrow or taper as it extends from the housing 434, and the slot 431 may narrow or taper as it extends through the guide block 430 (i.e., with depth). The housing 434 may include a base surface or portion that engages an outer face of the guide block 430 when the tang portion 433 of the laser device 432 is fully seated within the slot 431 of the guide block 430, as shown in FIGS. 27 and 28, which may assist in securely mounting the laser device 432 to the guide block 430. In some guide embodiments, the slot 431 of the guide block 430 may be configured to represent a joint line of the anatomical configuration/structures of the patient and/or of an implant replacing such configuration/structures.

The guide block 430 and the laser device 432 may be configured such that the laser light line 438 projected from the laser device 432 is aligned with the guide block 430 when the guide block 430 and the laser device 432 are coupled together (e.g., the tang portion 433 is seated within the slot 431). For example, the guide block 430 and the laser device 432 may be configured such that the laser light line 438 is aligned with the center of the resected anatomical structure (e.g., bone) that is resected via the guide block 430, such as along the medial-lateral direction and/or in the coronal plane. The guide block 430 and the laser device 432 may be configured such that the laser light line 438 is aligned with an implant replacing the anatomical configuration/structures that is coupled to the resected anatomical structure (e.g., bone) that is resected via the guide block 430.

As the laser light line 438 can be aligned to the alignment axis (e.g., an anatomical or mechanical axis) of the anatomical configuration/structures of the patient via the guide system (as in detail described above and below), the guide block 430 (and the resected surface(s) formed thereby and/or an implant configured to be implanted therein/thereon), can thereby also be aligned to the alignment axis (e.g., an anatomical or mechanical axis) of the anatomical configuration/structures of the patient, such as at least along the medial-lateral direction and/or in the coronal plane. In some embodiments, such a configuration of the guide block 430 and the laser device 432 comprises the tang 433 and the slot 431 being aligned/centered and/or orthogonal to the light line 438 projected from the laser device 432.

Figure 32:
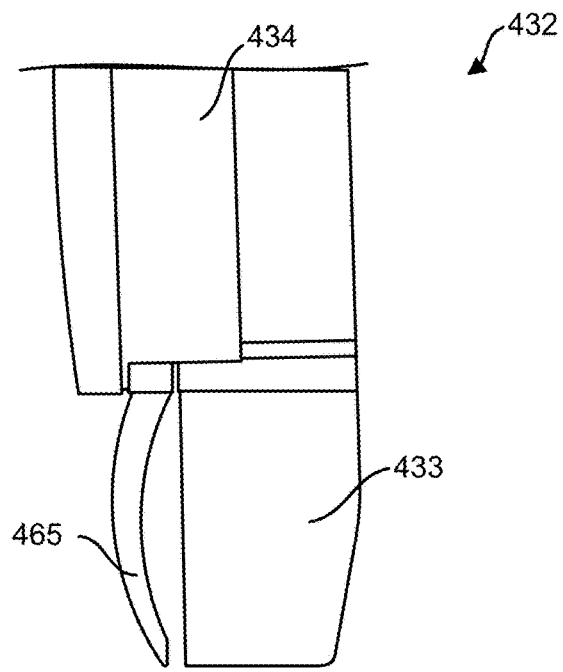
FIG. 32 illustrates a top view of the tang portion of the laser device of FIG. 25 with a switch thereof in a non-activated state.

In some embodiments, the tang portion 433 may include the switch 465 that is configured to activate the laser line module 436, as shown in FIGS. 32 and 33. The switch 465 may be configured to be automatically activated when the tang portion 433 is inserted into the slot 431 of the guide block 430. For example, as shown in FIG. 32, the switch 465 may be in an "open" or non-activated state or position when the tang portion 433 is not inserted within the slot 431 or otherwise exposed such that the power from the power source 464 is not applied to the laser line module 436 (i.e., the laser line module 436 is off). Conversely, as shown in FIG. 33, the tang portion 433 and the slot 431 may be sized or otherwise configured such that the switch 465 is automatically moved or deformed into a "closed" or activated state or position when the tang portion 433 is seated within the slot 431 such that the power from the power source 464 is applied to the laser line module 436 (i.e., the laser line module 436 is on).

The guide block 430 may be a portion or a component of an adjustable guide system that is configured to assist in aligning the guide block 430 to the anatomical configuration/structures of the patient (e.g., to the alignment axis (e.g., an anatomical or mechanical axis) of anatomical structures of interest) via, at least partially, the laser light 438 emitted from the laser device 432, as described above. The guide block 430 (and potentially one or more other guides of the guide system) may be configured as a resection guide that facilitates a specific resection of one or more anatomical configuration/structures of a patient (after being aligned thereto).

Figure 29:
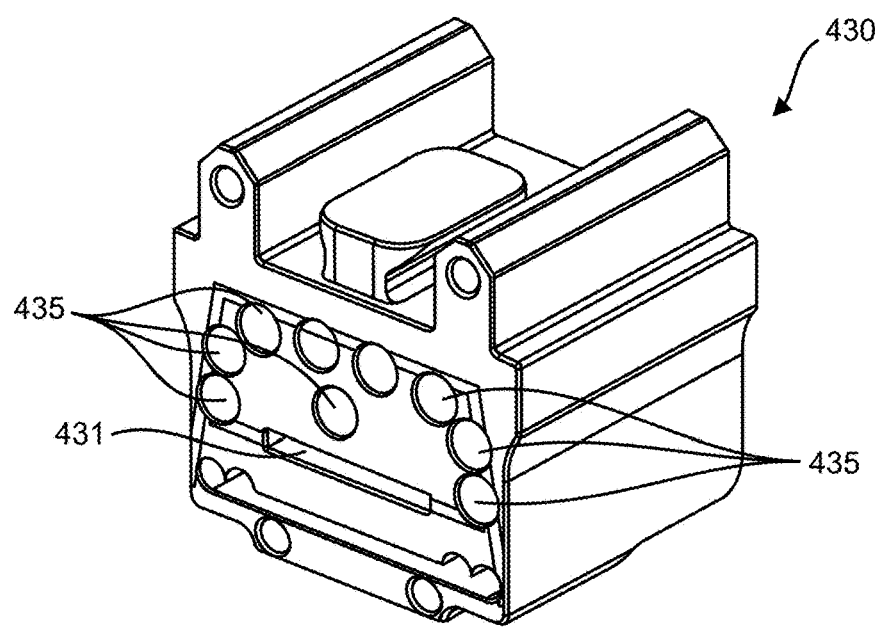
FIG. 29 illustrates an elevational perspective view of the guide block of FIG. 27.
Figure 30:
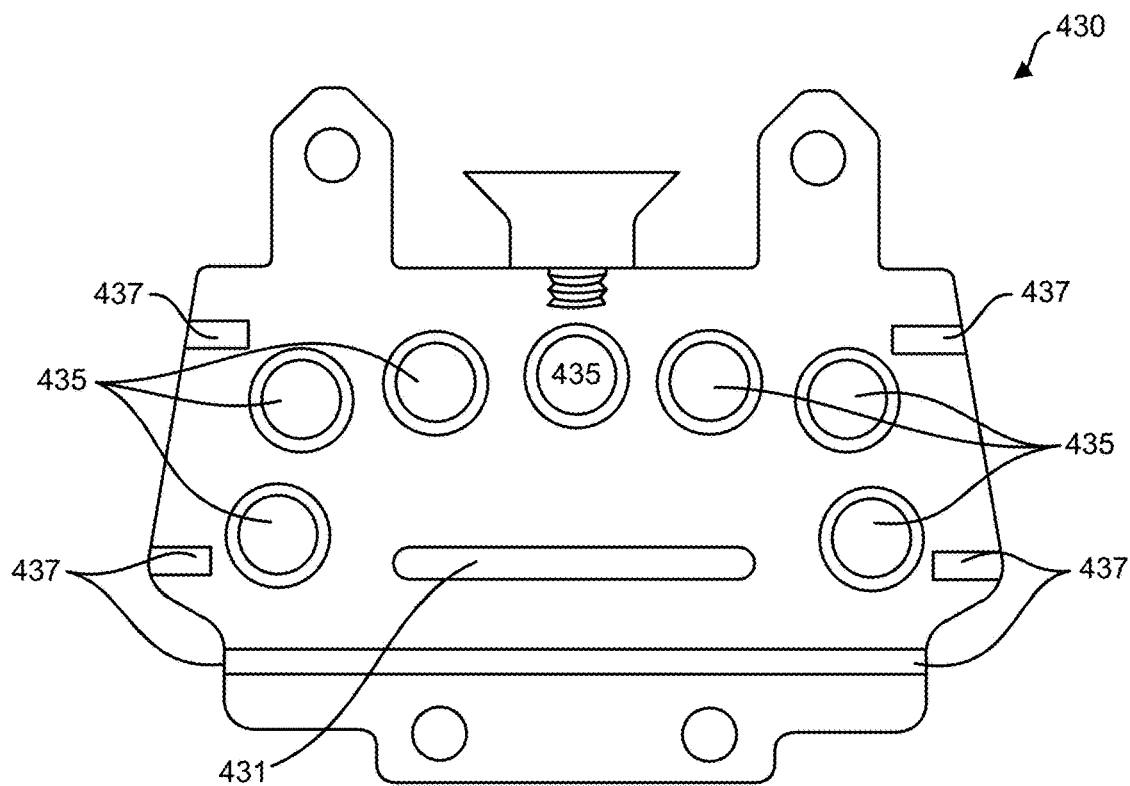
FIG. 30 illustrates a front view of the guide block of FIG. 27.
Figure 31:
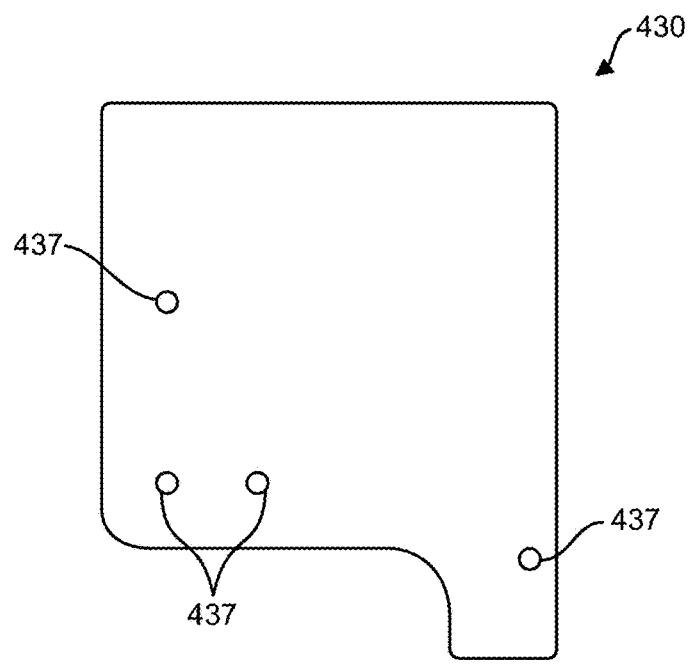
FIG. 31 illustrates a side view of the guide block of FIG. 27.

The guide block 430 may include visual indications that further assist in aligning the guide block 430 to the anatomical configuration/structures of the patient (e.g., to the alignment axis (e.g., an anatomical or mechanical axis) of anatomical structures of interest). For example, as shown in FIGS. 29-31, the guide block 430 may be radiolucent and include radiopaque reference members or portions 437 that allow a user to determine/evaluate the position and orientation of the guide block (and/or one or more resections formed via the guide block 430) with respect to the anatomical configuration/structures of the patient under x-ray/fluoroscopy. For example, the radiopaque reference members 437 may be configured to allow a user to determine/evaluate the position and orientation of the guide block (and/or one or more resections formed via the guide block 430) with respect to the anatomical configuration/structures of the patient (potentially under x-ray/fluoroscopy) when viewed along the anterior-posterior and/or medial-lateral directions.

As another example, as shown in FIGS. 29-31, the guide block 430 may include indications 435 (e.g., externally-visible indications and/or radiopaque indications) that allow a user to determine/evaluate the orientation/position and size of the guide block 430 (and/or one or more resections formed via the guide block 430) with respect to the anatomical configuration/structures of the patient when viewed along the anterior-posterior and/or medial-lateral directions. In some embodiments, the indications 435 may represent or correspond to resection apertures, slots or the like that can be used to (partially) resect the anatomical configuration/structure of the patient, such as a distal tibia. For example, after the guide block 430 is properly positioned and oriented with respect to the anatomical configuration/structures of the patient (e.g., to the alignment axis (e.g., an anatomical or mechanical axis) of anatomical structures of interest) via the laser light 438 of the laser device 432 and the indications 437, 435 of the guide block 430 (and the guide block 430 may be fixedly coupled to the anatomical configuration/structures of the patient (as described further below)), the laser device 432 may be removed or decoupled from the guide block 430, and the guide block 430 (e.g., the indications 435) utilized with a drill or other cutting implement to at least partially resect a portion of the anatomical configuration/structures of the patient (such as a distal tibia).

Figure 34:
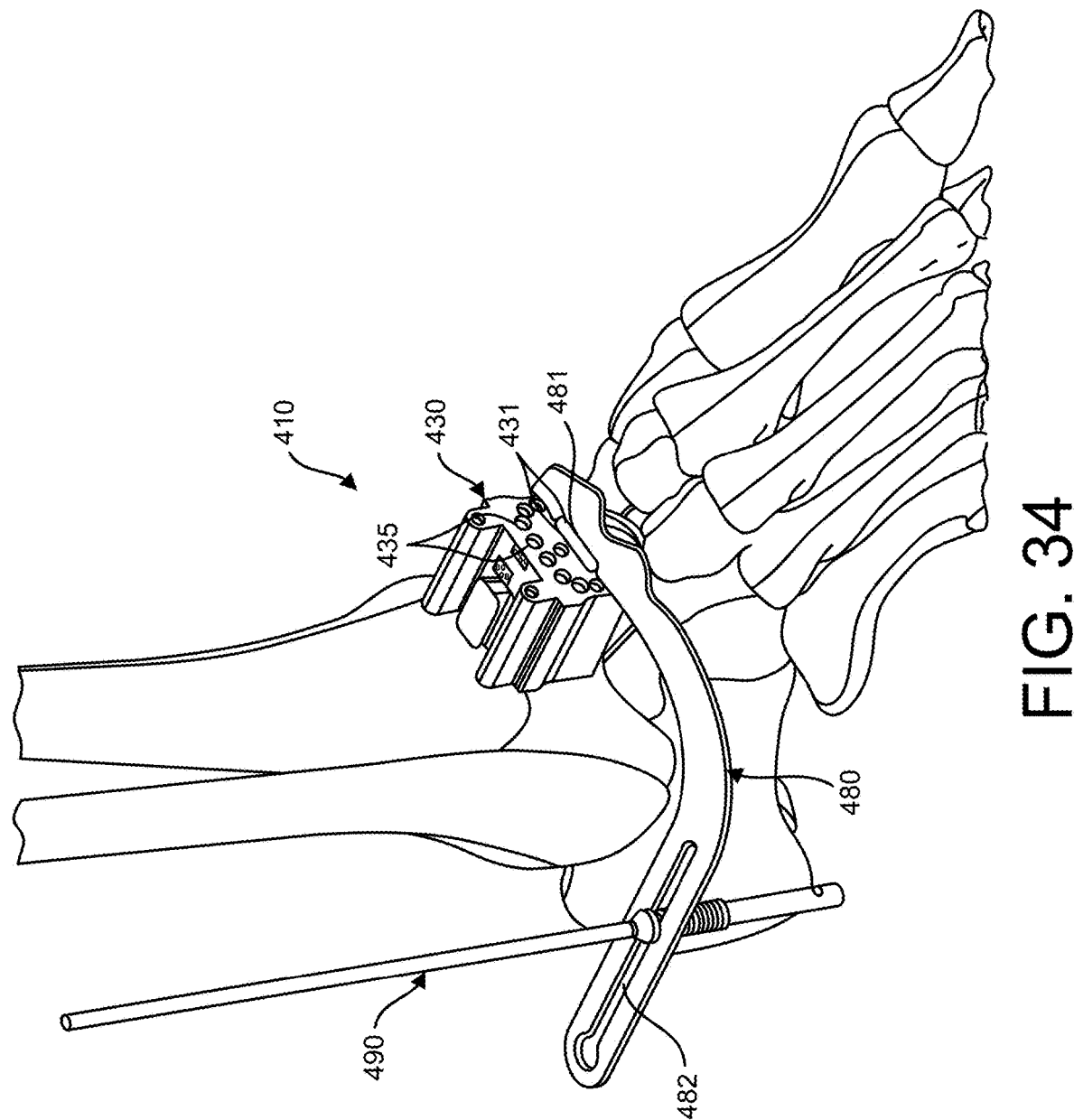
FIG. 34 illustrates a front elevational perspective view of the guide block of FIG. 27 engaged with an exemplary alignment wing member with respect to an ankle joint.
Figure 35:
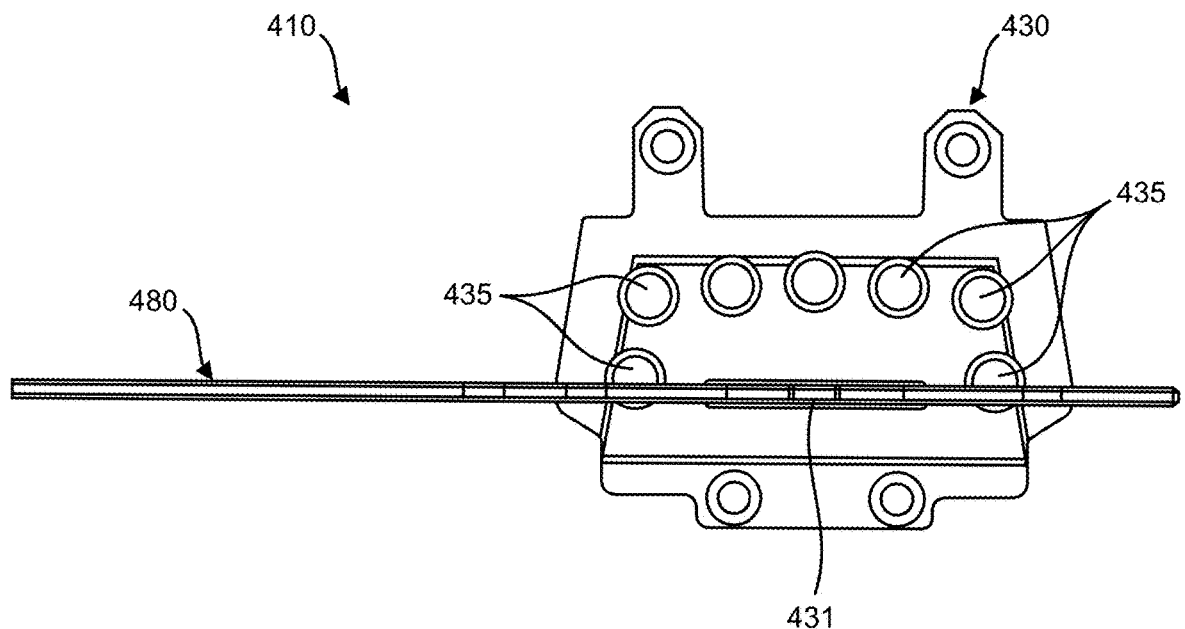
FIG. 35 illustrates a front view of the guide block and alignment wing member of FIG. 34.
Figure 36:
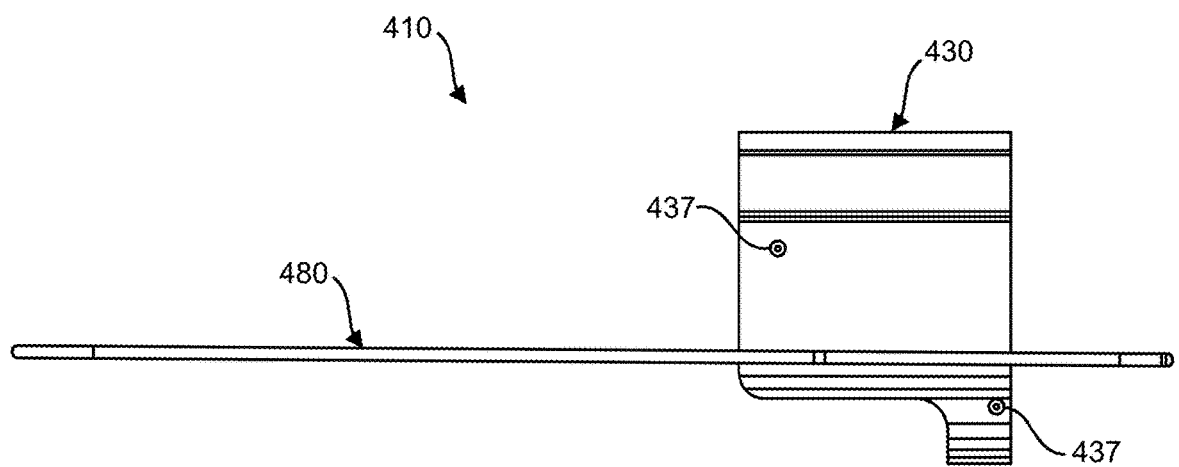
FIG. 36 illustrates a side view of the guide block and alignment wing member of FIG. 34.

As shown in FIGS. 34-36, in some embodiments the implant alignment and guide method and system 410 may further include an alignment wing member 480 that aids in aligning the system 410, and in particular the guide block 430 (and any other guide components of the guide system 410) with the anatomical configuration/structures of the patient (e.g., to the alignment axis (e.g., an anatomical or mechanical axis) of anatomical structures of interest). As shown in FIGS. 34-36, the wing member 480 may be flat/planar wing and configured to extend from the guide block 430 and at least partially about at least one anatomical structure of interest (coupled to the guide block 430) (e.g., extends in at least two directions, such as medial-laterally and anteriorly-posteriorly) to provide a visual reference of the orientation (e.g., slope) of the guide block 430 (and/or one or more resections formed via the guide block 430) with respect to the anatomical configuration/structures of the patient. For example, the wing member 480 (itself or a flat surface thereof) may extend along a plane aligned with the joint line of the anatomical configuration/structures of the patient (e.g., an ankle joint) and/or of a particular implant replacing such configuration/structures (e.g., a total ankle replacement implant) implanted on/in a resected bone that is/are resected (at least partially) via the guide block 430 and/or another component or portion of the guide system 410.

The wing member 480 may thereby allow a user to determine/evaluate the orientation (e.g., slope) of the joint line of the anatomical configuration/structures of the patient (e.g., an ankle joint) and/or of a particular implant replacing such configuration/structures (e.g., a total ankle replacement implant) implanted on/in a resected bone that is resected (at least partially) via the guide block 430 and/or another portion of the guide system 410 along at least two directions (such as medial-laterally and anteriorly-posteriorly), potentially with respect to the mechanical or other alignment axis of the anatomical configuration/structures.

As shown in FIGS. 34-36, the wing member 480 may be configured to removably couple with the guide block 430. For example, in some embodiments the wing member 480 may include a tang, tab or projection portion 481 that is configured to removably, but securely, fit within the slot of the guide block 430 of the system 410, as shown in FIG. 34. In this way, the wing member 480 can be used prior or subsequent to the laser device 432 as another reference guide to align the guide block 430 (and the system 410 as a whole) to the anatomical configuration/structures of the patient (e.g., to the alignment axis (e.g., an anatomical or mechanical axis) of anatomical structures of interest).

As shown in FIG. 34, the system 410 may further include an elongate auxiliary alignment member or rod 490 coupled to the wing member 480. The auxiliary alignment member 490 may be movably coupled to the wing member 480, such as within a slot 482 of the wing member 480 (which may extend anteriorly-posteriorly). The auxiliary alignment member 490 may be oriented perpendicular (in at least one direction) or normal to the wing member 480, and thereby perpendicular (in at least one direction) or normal to the joint line referenced by the slot 431 and the wing member 480 (as discussed above). The auxiliary alignment member 490 may thereby allow a user to determine/evaluate the alignment (e.g., sagittal alignment) and/or orientation (e.g., sagittal slope and/or coronal slope) of the joint line of the anatomical configuration/structures of the patient (e.g., an ankle joint) and/or of a particular implant replacing such configuration/structures (e.g., a total ankle replacement implant) implanted on/in a resected bone that is resected (at least partially) via the guide block 430 or another portion or component of the guide system 410, potentially with respect to the mechanical or other alignment axis thereof.

Figure 37:
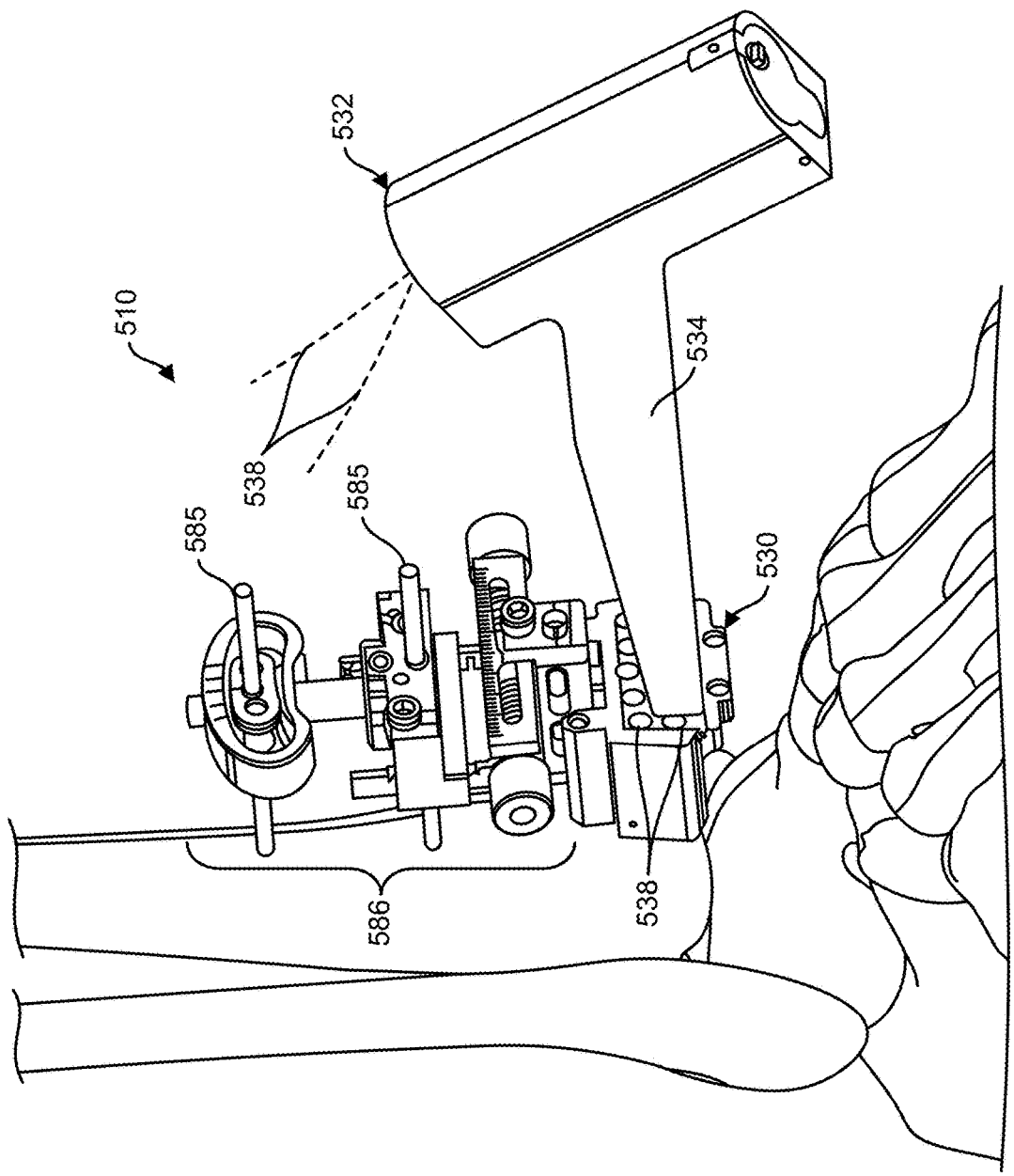
FIG. 37 illustrates an elevational perspective view of another exemplary embodiment of a laser-based implant alignment system according to the present disclosure incorporating the laser device of FIG. 25 and the guide block of FIG. 27 with respect to an ankle joint.
Figure 38:
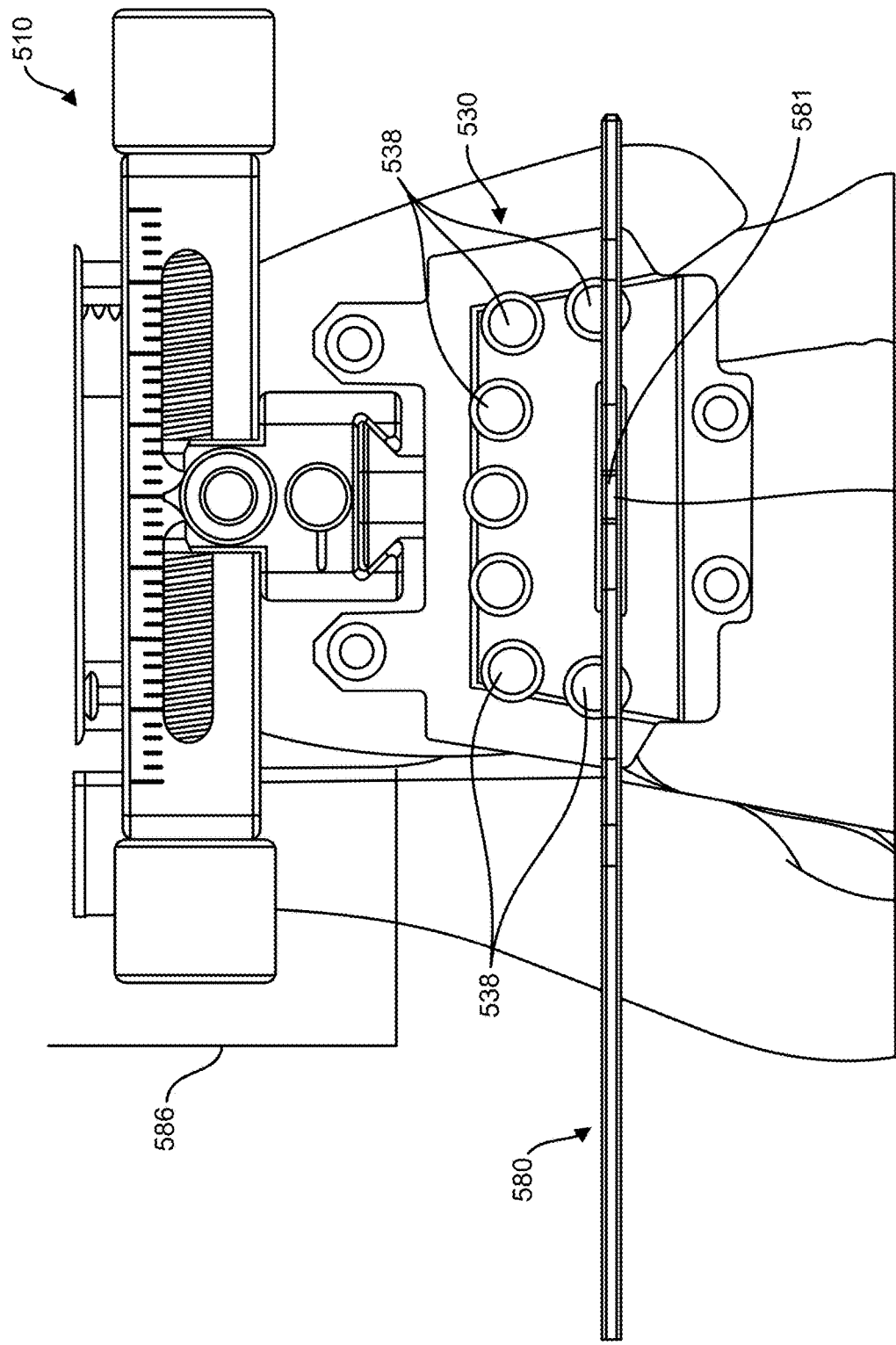
FIG. 38 illustrates a front view of a portion of the laser-based implant alignment system of FIG. 37.

FIGS. 37 and 38 illustrate another exemplary implant alignment or guidance system and method according to the present disclosure. The exemplary implant alignment and guide method and system 510 of FIGS. 37 and 38 is substantially similar to the exemplary implant alignment and guide methods 10 and systems described above with respect to FIGS. 1-22, the exemplary implant alignment and guide method and system described above with respect to FIG. 23, the exemplary implant alignment and guide method and system described above with respect to FIG. 24 and the exemplary implant alignment and guide method and system 410 described above with respect to FIGS. 25-36, and therefore like reference numerals preceded by the numeral "5" are used to indicate like elements, aspects, functions, actions, configurations and the like. The implant alignment and guide system and method of FIGS. 37 and 38 may include any of the elements, aspects, functions, actions, configurations and the like of the implant alignment and guide system and method 10 of FIGS. 1-22, the implant alignment and guide method and system described above with respect to FIG. 23, the implant alignment and guide method and system described above with respect to FIG. 24 and/or the exemplary implant alignment and guide method and system 410 described above with respect to FIGS. 25-36. The description above with respect to the implant alignment and guide system and method 10 of FIGS. 1-22, the implant alignment and guide method and system described above with respect to FIG. 23, the implant alignment and guide method and system described above with respect to FIG. 24 and/or the exemplary implant alignment and guide method and system 410 described above with respect to FIGS. 25-36 thereby equally applies to the exemplary implant alignment system and method 510 of FIGS. 37 and 38, including description regarding alternative embodiments thereto (i.e., modifications, variations or the like).

As shown in FIGS. 37 and 38, the implant and guide alignment system 510 comprises a laser device that is the same or substantially similar to the laser device 432 described above with respect to FIGS. 25-36, a guide block 530 that is the same or substantially similar to the guide block 430 described above with respect to FIGS. 25-36, and a guide wing member 580 that is the same or substantially similar to the guide wing member 580 described above with respect to FIGS. 25-36 (and potentially an elongate auxiliary alignment member coupled thereto that is the same or substantially similar to the elongate auxiliary alignment member 490 described above with respect to FIGS. 25-36). The implant alignment and guide method and system 510 includes additional guide components 586 that are coupled to and extend from the guide block 530, as shown in FIGS. 37 and 38.

As shown in FIG. 37, one or more of the additional guide components 586 may extend to and be affixed or coupled to anatomical configuration/structures of a patient (e.g., a tibia of an ankle joint) via a pin, k-wire or other like fixation member 585 substantially proximate to the guide block 530. For example, the guide block 530 may be positioned at a distal tibia when the guide method and system 510 is utilized to prepare a tibia for an ankle arthroplasty and the guide components 586 may extend to, and potentially be couple to, the distal tibia or a medial portion of the tibia, as shown in FIGS. 37 and 38. As least one initial fixation member 585 may initially be implanted into the anatomical configuration/structures of the patient, and at least one of the guide components 586 positioned thereon (loosely or securely). The guide components 586 may then adjusted such that the laser light 538 of the laser device 532 extending from the guide block 530 is aligned with a target indication (e.g., of target member or an anatomical structure of the patient) to align the guide block 530 (and thereby the resected surface(s) formed thereby, and the implant implanted therein/thereon) with the anatomical configuration/structures of the patient (e.g., to the alignment axis (e.g., an anatomical or mechanical axis) of the anatomical configuration/structures of interest). Further, as discussed above, the laser device 532 may be decoupled from the guide block 530, and the alignment wing member 580 may also be utilized to align the guide block 530 (and thereby the resected surface(s) formed thereby, and the implant implanted therein/thereon) with the anatomical configuration/structures of the patient (e.g., to the alignment axis (e.g., an anatomical or mechanical axis) of the anatomical.

After the alignment guide method and system 510 is fully properly aligned with the anatomical configuration/structures of the patient (e.g., to the alignment axis (e.g., an anatomical or mechanical axis) of the anatomical configuration/structures of interest) via the laser device 532 and/or the alignment wing member 580 for example, at least one additional fixation member 585 may be implanted into the anatomical configuration/structures of the patient and through at least one component or portion of the guide components 586 and/or the guide components 586 may be securely affixed to the previously implanted at least one initial fixation member 585 to fix the guide block 530 to the anatomical configuration/structures of the patient such that is can be utilized to at least partially resect a portion of the anatomical configuration/structures of the patient. In some embodiments, after the guide block 530 is utilized to at least partially resect a portion of the anatomical configuration/ structures of the patient, the guide block 530 may be removed or decoupled from the guide method and system 510 and at least one secondary guide block or other resection guide may be utilized with the guide method and system 510 (e.g., secured or coupled to the guide components 586) to further resect a portion of the anatomical configuration/structures of the patient.

The guide components 586 may be configured to adjust the guide block 530 (and thereby the resected surface(s) formed thereby, and the implant implanted therein/thereon) with respect to the anatomical configuration/structures of the patient (e.g., to the alignment or mechanical axis thereof) in a plurality of degrees of freedom. For example, the guide components 586 may be configured to adjust in five (5) degrees of freedom. In some embodiments, the guide components 586 of the alignment guide method and system 510 may be adjustable in or with respect to a first direction or plane, which may extend along or correspond to a sagittal plane when the alignment guide method and system 510 is positioned on an anterior side of a patient (e.g., proximal-distal and/or flexion/extension adjustment) (e.g., when utilized in an ankle arthroplasty). In some embodiments, the guide components 586 of the alignment guide method and system 510 may be adjustable in or with respect to a second direction or plane, which may extend along or correspond to the transverse plane when the alignment guide method and system 510 are positioned on the anterior side of the patient (e.g., internal/external adjustment) (e.g., when utilized in an ankle arthroplasty). In some embodiments, the guide components 586 of the alignment guide method and system 510 may be adjustable in or with respect to a third direction or plane, which may extend along or correspond to the coronal plane when the alignment guide method and system 510 are positioned on the anterior side of the patient (e.g., varus/valgus adjustment) (e.g., when utilized in an ankle arthroplasty). In some embodiments, the guide components 586 of the alignment guide method and system 510 may be adjustable in or with respect to a fourth direction or plane, which may extend along or correspond to the superior-inferior direction when the alignment guide method and system 510 is positioned on the anterior side of the patient (e.g., when utilized in an ankle arthroplasty). In some embodiments, the guide components 586 of the alignment guide method and system 510 may be adjustable in or along a fifth direction or plane, which may extend along or correspond to the medial-lateral direction when the alignment guide method and system 510 is positioned on the anterior side of the patient (e.g., when utilized in an ankle arthroplasty).

Figure 39:
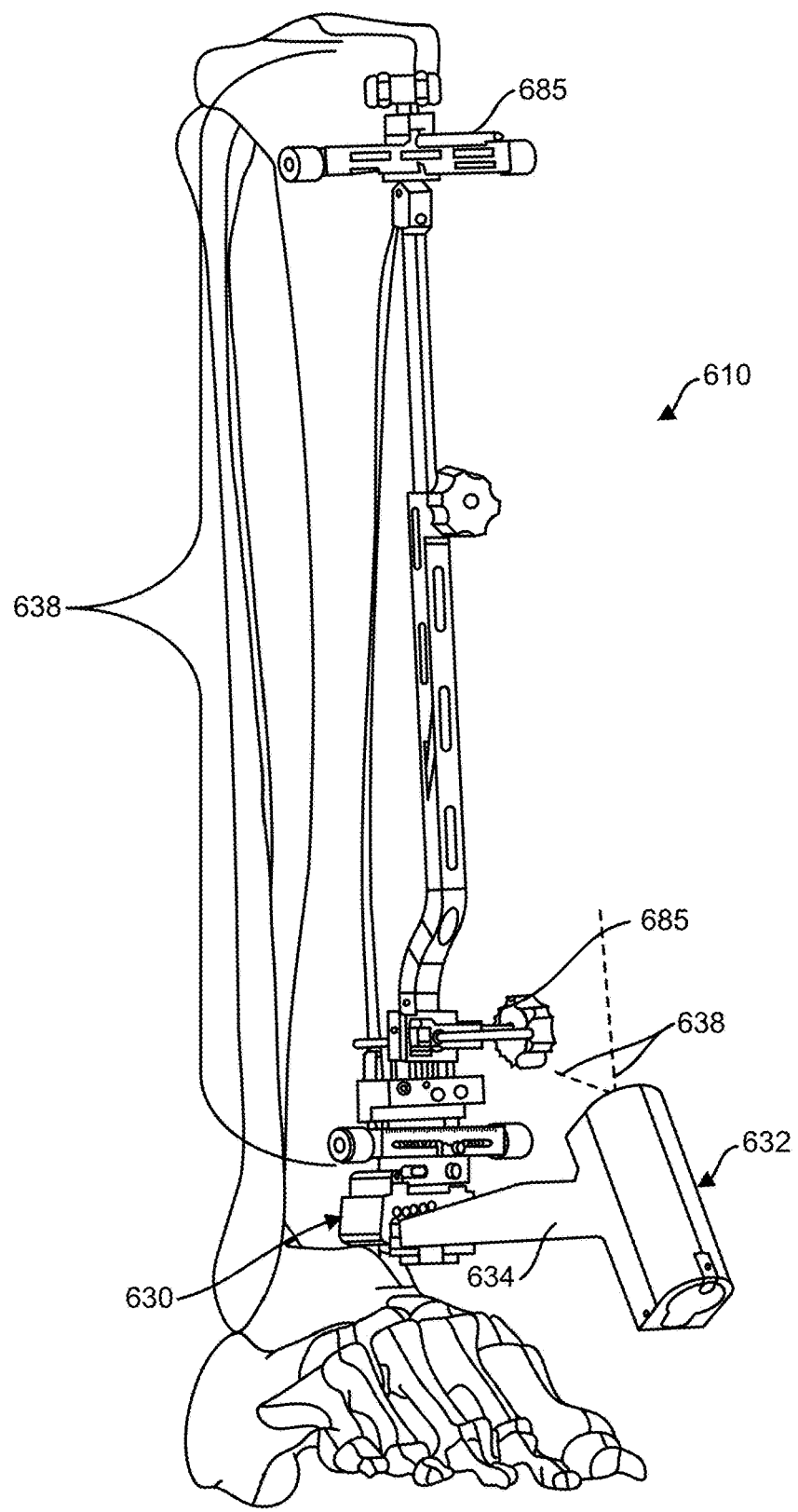
FIG. 39 illustrates an elevational perspective view of another exemplary embodiment of a laser-based implant alignment system according to the present disclosure incorporating the laser device of FIG. 25 and the guide block of FIG. 27 with respect to an ankle joint.
Figure 40:
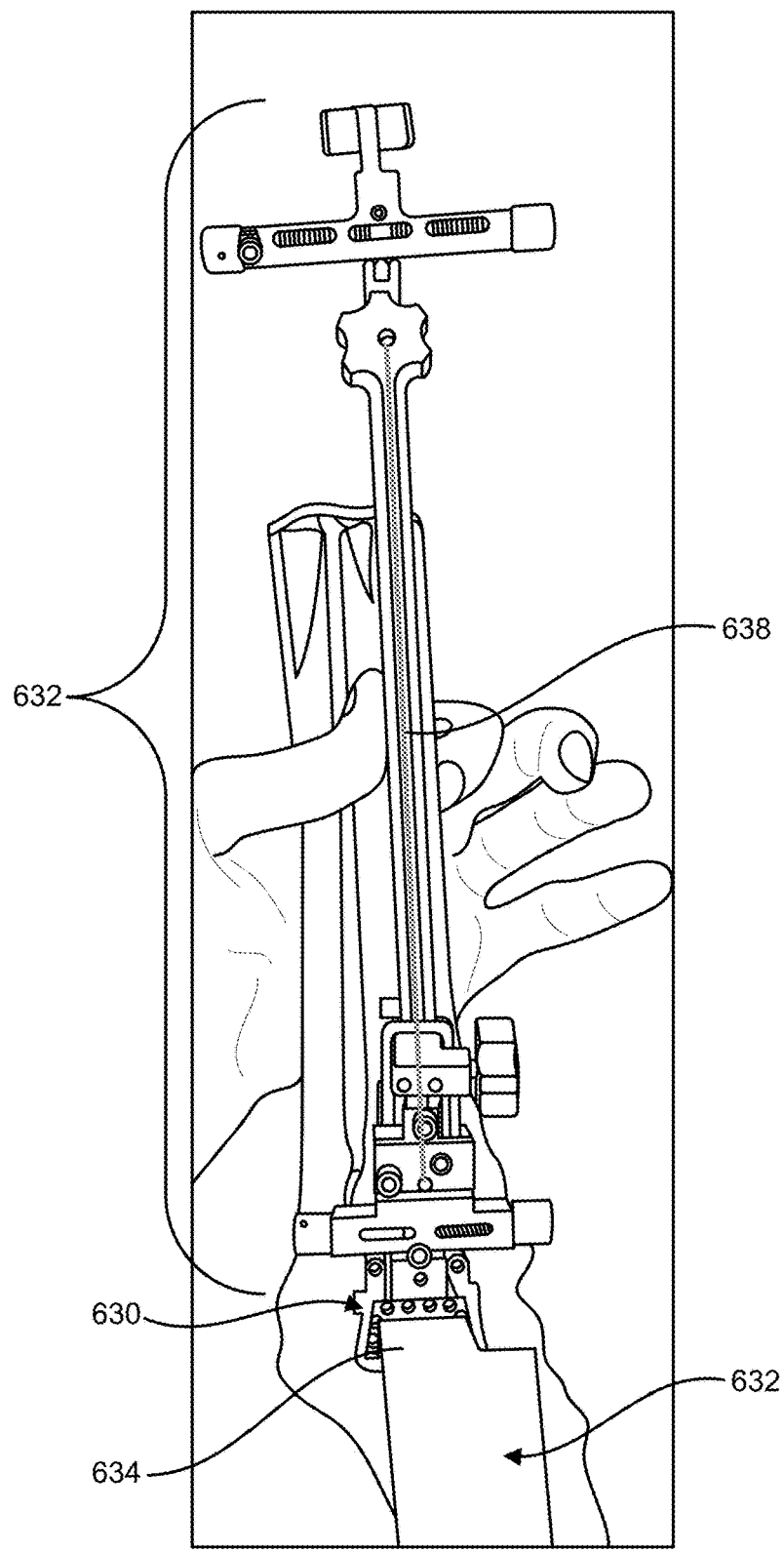
FIG. 40 illustrates a front view of a portion of the laser-based implant alignment system of FIG. 39.

FIGS. 39 and 40 illustrate another exemplary implant alignment or guidance system and method according to the present disclosure. The exemplary implant alignment and guide method and system 610 of FIGS. 39 and 40 is substantially similar to the exemplary implant alignment and guide methods 10 and systems described above with respect to FIGS. 1-22, the exemplary implant alignment and guide method and system described above with respect to FIG. 23, the exemplary implant alignment and guide method and system described above with respect to FIG. 24, the exemplary implant alignment and guide method and system 410 described above with respect to FIGS. 25-36 and the exemplary implant alignment and guide method and system 510 described above with respect to FIGS. 37 and 38, and therefore like reference numerals preceded by the numeral "6" are used to indicate like elements, aspects, functions, actions, configurations and the like. The implant alignment and guide system and method 610 of FIGS. 39 and 40 may include any of the elements, aspects, functions, actions, configurations and the like of the implant alignment and guide system and method 10 of FIGS. 1-22, the implant alignment and guide method and system of FIG. 23, the implant alignment and guide method and system of FIG. 24, the exemplary implant alignment and guide method and system 410 of FIGS. 25-36 and/or the exemplary implant alignment and guide method and system 510 of FIGS. 37 and 38. The description above with respect to the implant alignment and guide system and method 10 of FIGS. 1-22, the implant alignment and guide method and system of FIG. 23, the implant alignment and guide method and system of FIG. 24, the exemplary implant alignment and guide method and system 410 of FIGS. 25-36 and/or the exemplary implant alignment and guide method and system 510 of FIGS. 37 and 38 thereby equally applies to the exemplary implant alignment system and method 610 of FIGS. 39 and 40, including description regarding alternative embodiments thereto (i.e., modifications, variations or the like).

As shown in FIGS. 39 and 40, the implant alignment and guide system 610 is substantially similar to the implant and guide alignment system 510 described above with respect to FIGS. 37 and 38. Implant alignment system 610 differs from implant alignment system 510 in that one or more of the guide components 686 of the implant alignment and guide system 610 may extend to and be affixed or coupled to anatomical configuration/structures of a patient (e.g., a tibia of an ankle joint) via a pin, k-wire or other like fixation member 585 substantially distal to the guide block 530. For example, the guide block 530 may be positioned at a distal tibia when the guide method and system 510 is utilized to prepare a tibia for an ankle arthroplasty and the guide components 586 may extend to, and potentially be couple to, the proximal end of the tibia (e.g., the tibia tubercle thereof), as shown in FIGS. 37 and 38.

Figure 41:
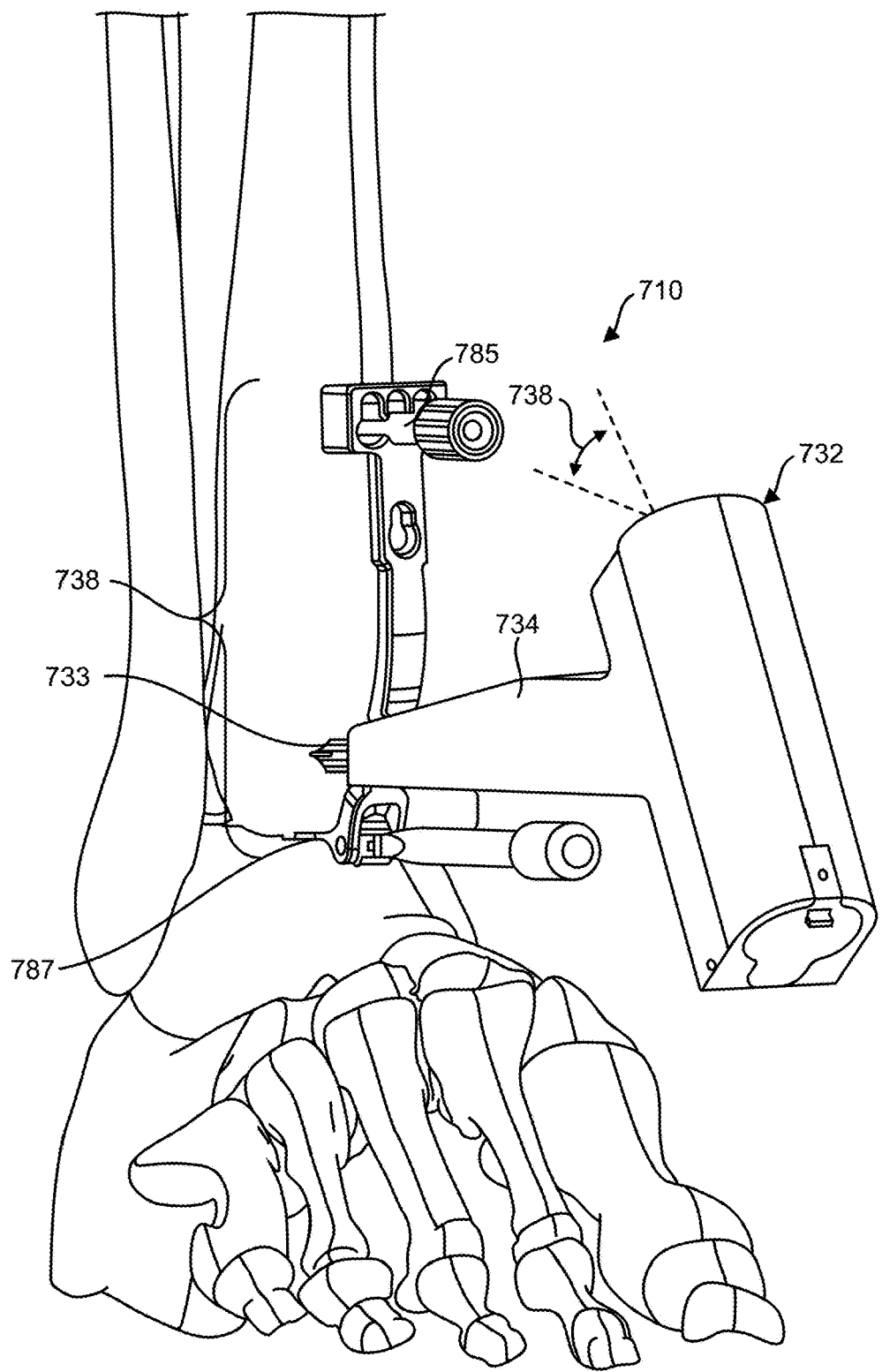
FIG. 41 illustrates an elevational perspective view of another exemplary embodiment of a laser-based implant alignment system according to the present disclosure incorporating the laser device of FIG. 25.
Figure 42:
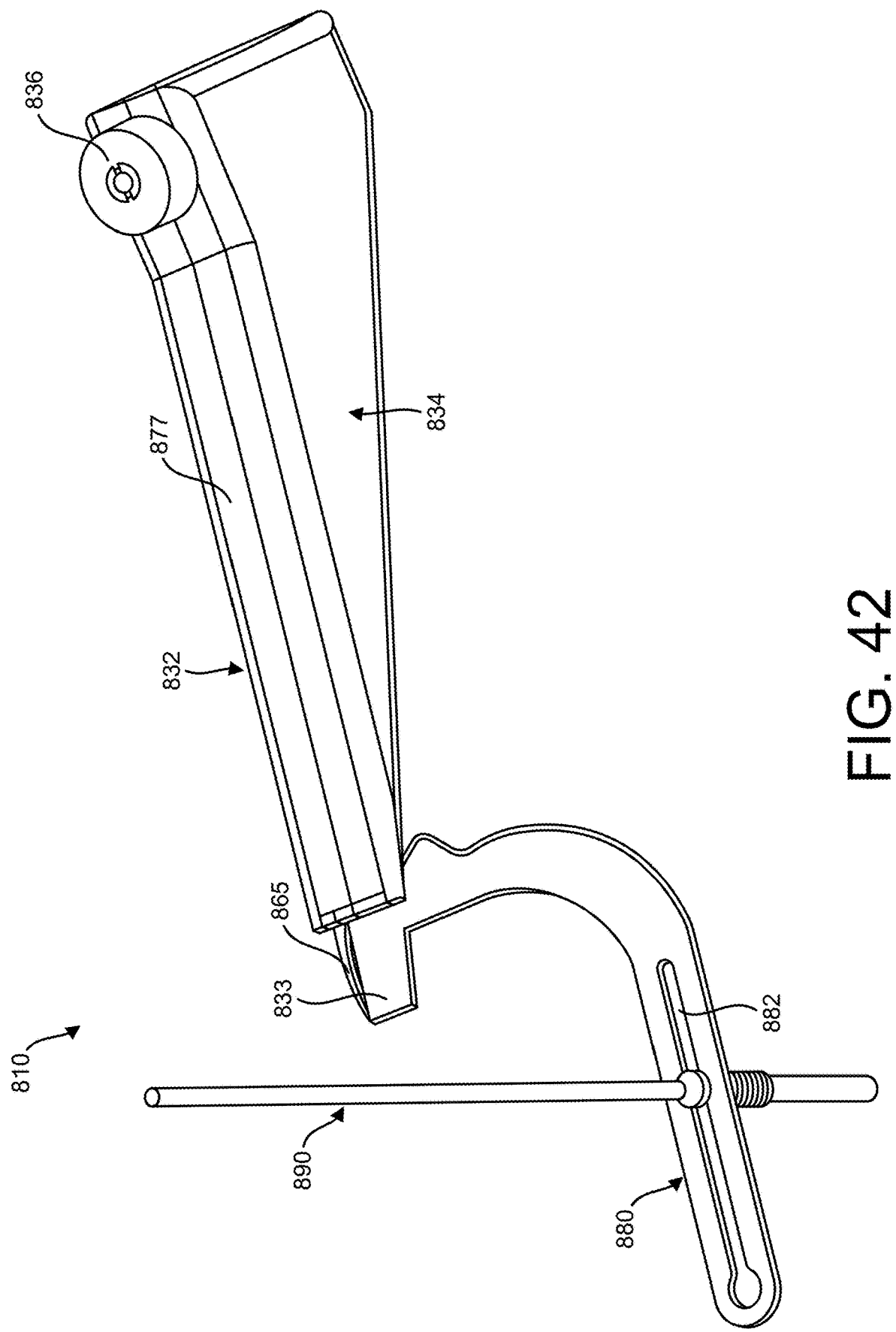
FIG. 42 illustrates an elevational perspective view another exemplary embodiment of a laser device of a laser-based implant alignment system according to the present disclosure.
Figure 43:
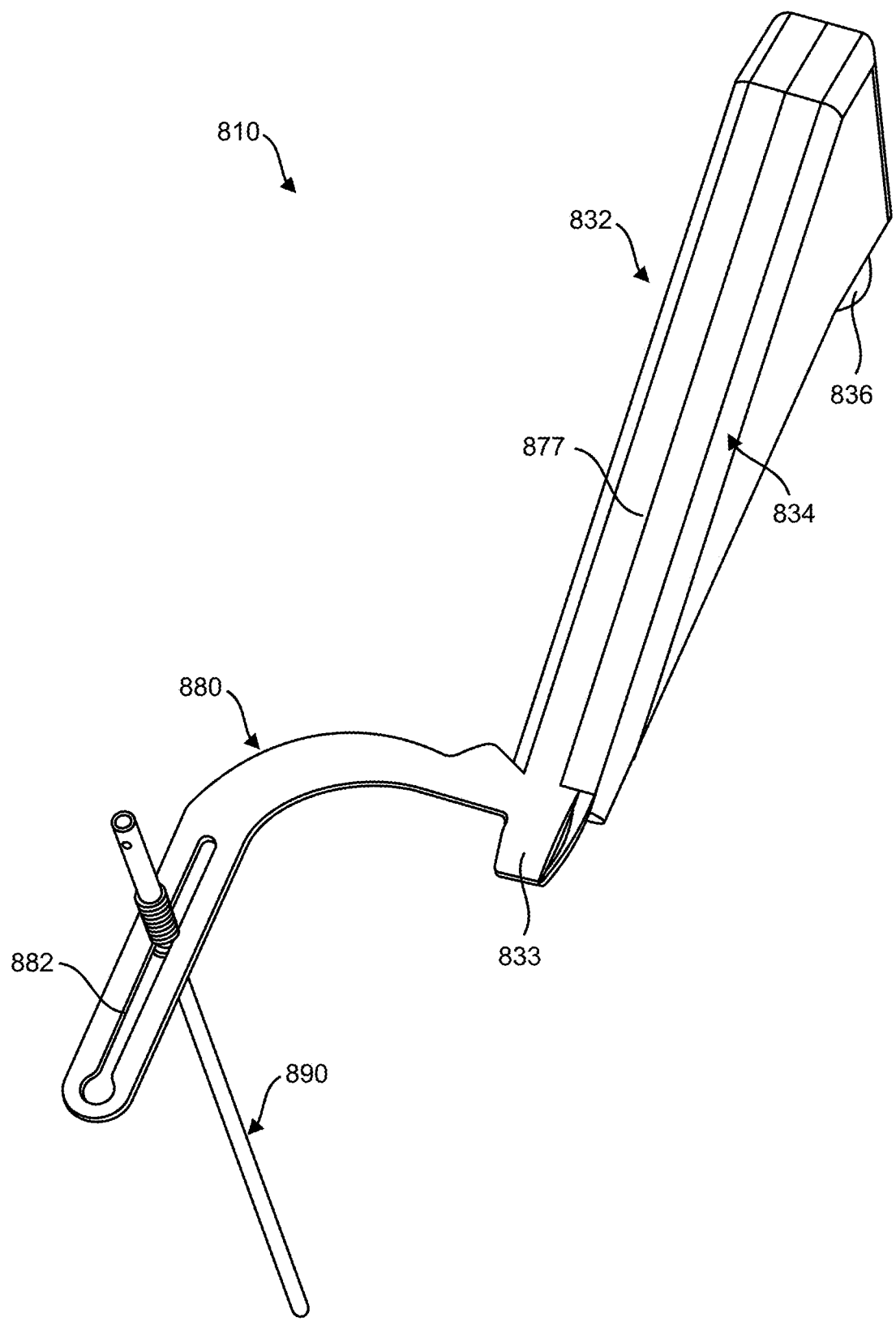
FIG. 43 illustrates a bottom perspective view of the laser device of FIG. 42.
Figure 44:
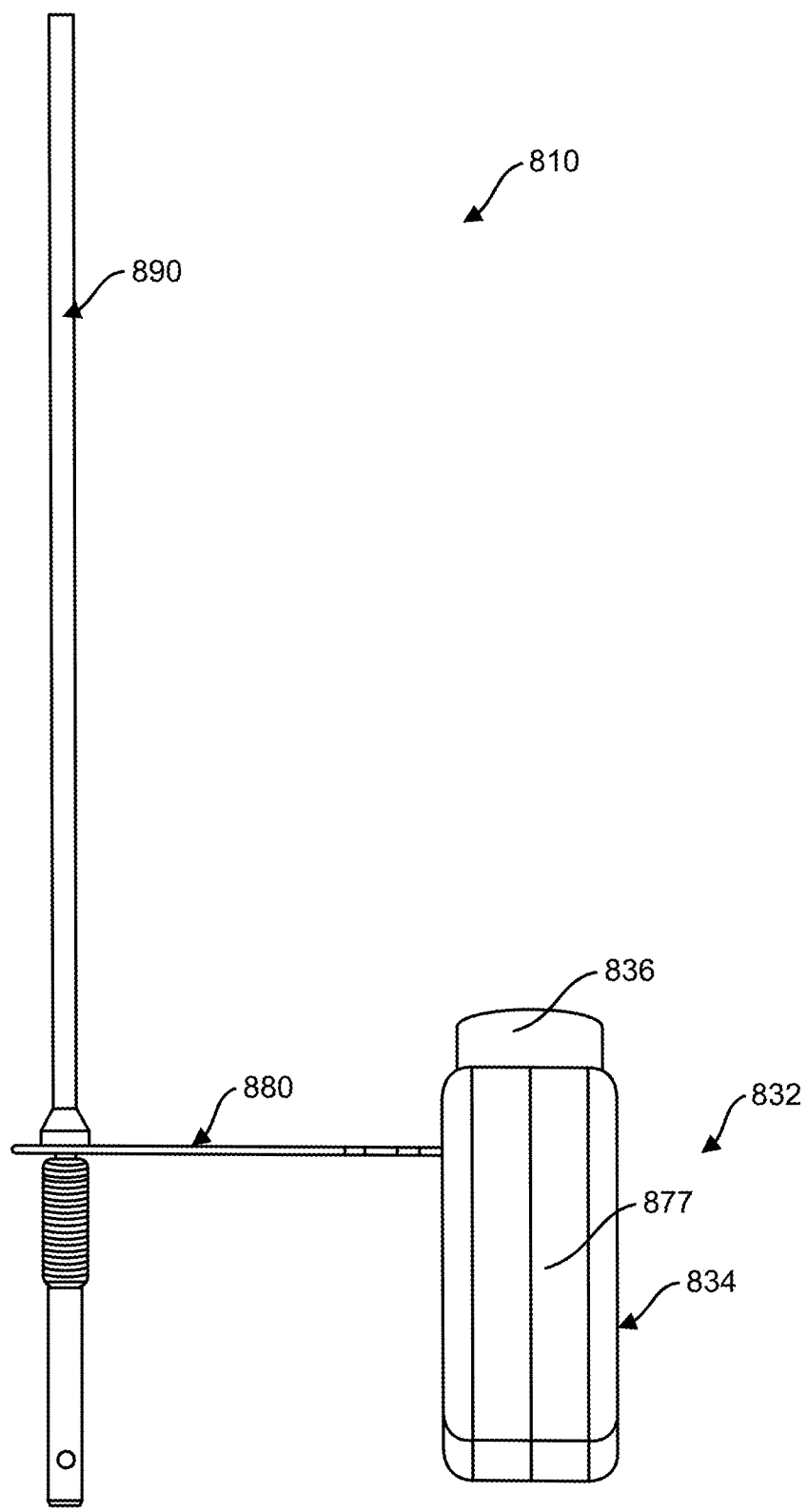
FIG. 44 illustrates a front view of the laser device of FIG. 42.
Figure 45:
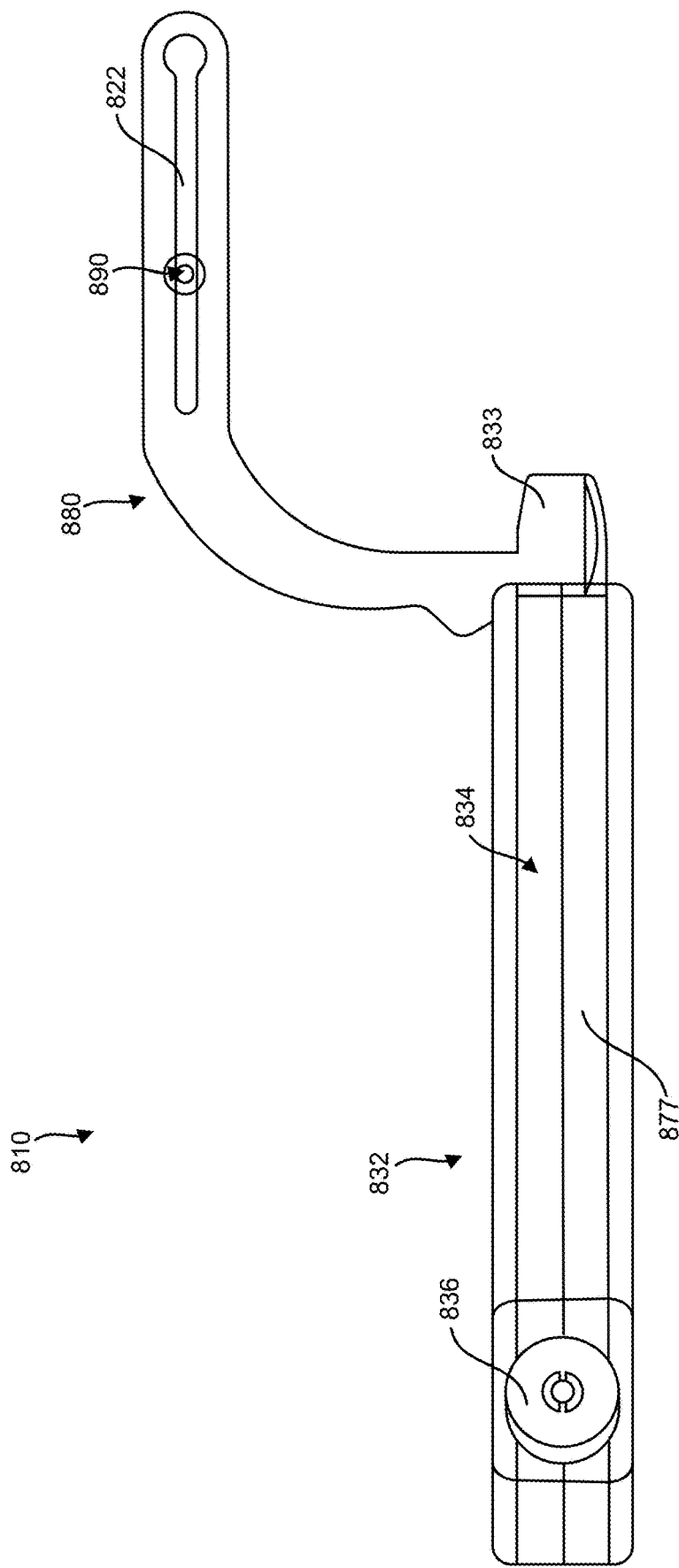
FIG. 45 illustrates a top view of the laser device of FIG. 42.

FIG. 41 illustrates another exemplary implant alignment or guidance system and method according to the present disclosure. The exemplary implant alignment and guide method and system 710 of FIG. 41 is substantially similar to the exemplary implant alignment and guide methods 10 and systems described above with respect to FIGS. 1-22, the exemplary implant alignment and guide method and system described above with respect to FIG. 23, the exemplary implant alignment and guide method and system described above with respect to FIG. 24, the exemplary implant alignment and guide method and system 410 described above with respect to FIGS. 25-36, the exemplary implant alignment and guide method and system 510 described above with respect to FIGS. 37 and 38 and the exemplary implant alignment and guide method and system 710 of FIGS. 39 and 40, and therefore like reference numerals preceded by the numeral "7" are used to indicate like elements, aspects, functions, actions, configurations and the like. The implant alignment and guide system and method 710 of FIG. 41 may include any of the elements, aspects, functions, actions, configurations and the like of the implant alignment and guide system and method 10 of FIGS. 1-22, the implant alignment and guide method and system of FIG. 23, the implant alignment and guide method and system of FIG. 24, the exemplary implant alignment and guide method and system 410 of FIGS. 25-36, the exemplary implant alignment and guide method and system 510 of FIGS. 37 and 38 and/or the implant alignment and guide system and method 610 of FIGS. 39 and 40. The description above with respect to the implant alignment and guide system and method 10 of FIGS. 1-22, the implant alignment and guide method and system of FIG. 23, the implant alignment and guide method and system of FIG. 24, the exemplary implant alignment and guide method and system 410 of FIGS. 25-36, the exemplary implant alignment and guide method and system 510 of FIGS. 37 and 38 and/or the implant alignment and guide system and method 610 of FIGS. 39 and 40 thereby equally applies to the exemplary implant alignment system and method 710 of FIG. 41, including description regarding alternative embodiments thereto (i.e., modifications, variations or the like).

As shown in FIG. 41, the implant alignment and guide method and system 710 comprises a laser device 732 that is the same or substantially similar to the laser device 432 described above with respect to FIGS. 25-36, but does not include or is void of the guide block 430 described above with respect to FIGS. 25-36. The implant alignment and guide method and system 710 includes additional guide components 786 that are coupled to and extend from the laser device 732, as shown in FIG. 41. Specifically, as shown in FIG. 41, the tang 733 of the laser device 732 engages or couples (fixedly or removably) within a slot (not shown) of the guide components 786 as shown in FIG. 41.

As also shown in FIG. 41, the guide components 786 form a shim device that includes a shim portion 787 that engages an end or end portion of an anatomical configuration/structure of a patient and a proximal portion that extends from and is affixed or coupled to the outer side or surface of the anatomical configuration/structures of the patient via a pin, k-wire or other like fixation member 785. For example, when the guide method and system 510 is utilized to prepare a tibia for an ankle arthroplasty, the shim portion 787 may engage a distal end of the tibia and the proximal portion of the guide components 786 may be affixed or coupled to the outer side or surface (e.g., an anterior side) of the tibia proximal from the shim portion 787 and distal end of the tibia via a fixation member 785, as also shown in FIG. 41.

FIGS. 42-52 illustrate another exemplary implant alignment or guidance system and method according to the present disclosure. The exemplary implant alignment and guide method and system 810 of FIGS. 42-52 is substantially similar to the exemplary implant alignment and guide methods 10 and systems described above with respect to FIGS. 1-22, the exemplary implant alignment and guide method and system described above with respect to FIG. 23, the exemplary implant alignment and guide method and system described above with respect to FIG. 24, the exemplary implant alignment and guide method and system 410 described above with respect to FIGS. 25-36, the exemplary implant alignment and guide method and system 510 described above with respect to FIGS. 37 and 38, the exemplary implant alignment and guide method and system 710 of FIGS. 39 and 40 and exemplary implant alignment and guide method and system 710 of FIG. 41, and therefore like reference numerals preceded by the numeral "8" are used to indicate like elements, aspects, functions, actions, configurations and the like. The implant alignment and guide system and method 810 of FIGS. 42-52 may include any of the elements, aspects, functions, actions, configurations and the like of the implant alignment and guide system and method 10 of FIGS. 1-22, the implant alignment and guide method and system of FIG. 23, the implant alignment and guide method and system of FIG. 24, the exemplary implant alignment and guide method and system 410 of FIGS. 25-36, the exemplary implant alignment and guide method and system 510 of FIGS. 37 and 38, the implant alignment and guide system and method 610 of FIGS. 39 and 40 and/or the implant alignment and guide method and system 710 of FIG. 41. The description above with respect to the implant alignment and guide system and method 10 of FIGS. 1-22, the implant alignment and guide method and system of FIG. 23, the implant alignment and guide method and system of FIG. 24, the exemplary implant alignment and guide method and system 410 of FIGS. 25-36, the exemplary implant alignment and guide method and system 510 of FIGS. 37 and 38, the implant alignment and guide system and method 610 of FIGS. 39 and 40 and/or alignment method and system 710 of FIG. 41 thereby equally applies to the exemplary implant alignment system and method 810 of FIGS. 42-52, including description regarding alternative embodiments thereto (i.e., modifications, variations or the like).

As shown in FIGS. 42-52, the exemplary implant alignment and guide method and system 810 comprises a laser device portion 832 that is the same or substantially similar to the laser device 432 of the guide method and system 510 described above with respect to FIGS. 25-36 and an alignment guide wing 880 that is the same or substantially similar to the alignment guide wing 580 of the implant alignment and guide method and system 510 described above with respect to FIGS. 34-36. The implant alignment and guide method and system 810 differs from the implant alignment and guide method and system 810 in that the laser device portion 832 and the alignment guide wing 880 are fixedly attached or integral. The implant alignment and guide system 810 may thereby comprise a one-piece device. In some embodiments, however, the system 810 may include an auxiliary alignment member (see auxiliary alignment member 490 of FIG. 34) as a separate and distinct component that is coupled (potentially removably coupled) to the alignment guide wing portion 880. As shown in FIGS. 42-52, the alignment guide wing 880 may extend from, and potentially include as a portion thereof, the tang 833 of the laser device portion 832. Stated differently, the laser device portion 832 may extend from, and potentially include as a portion thereof, the tang 833 of the alignment guide wing 880.

Figure 46:
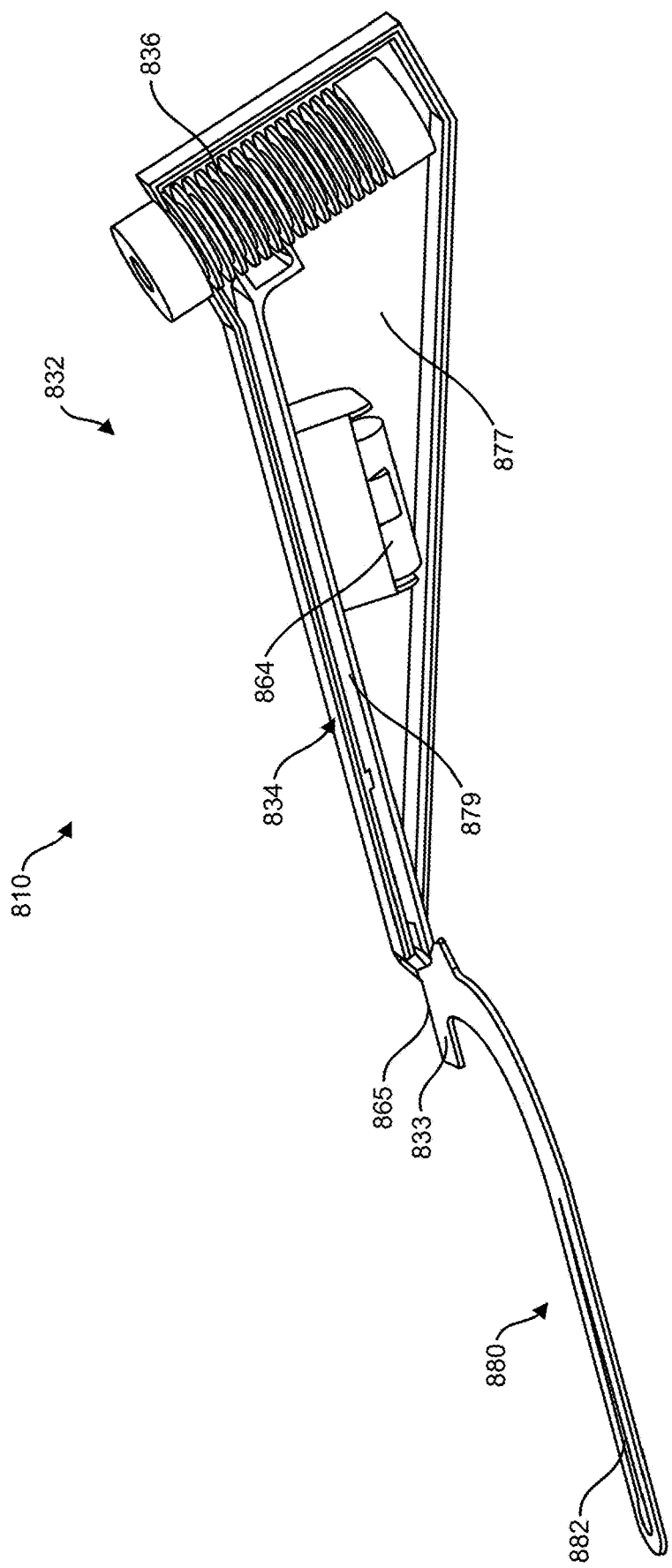
FIG. 46 illustrates a perspective view of the laser device of FIG. 42 with a portion of the housing thereof removed.
Figure 47:
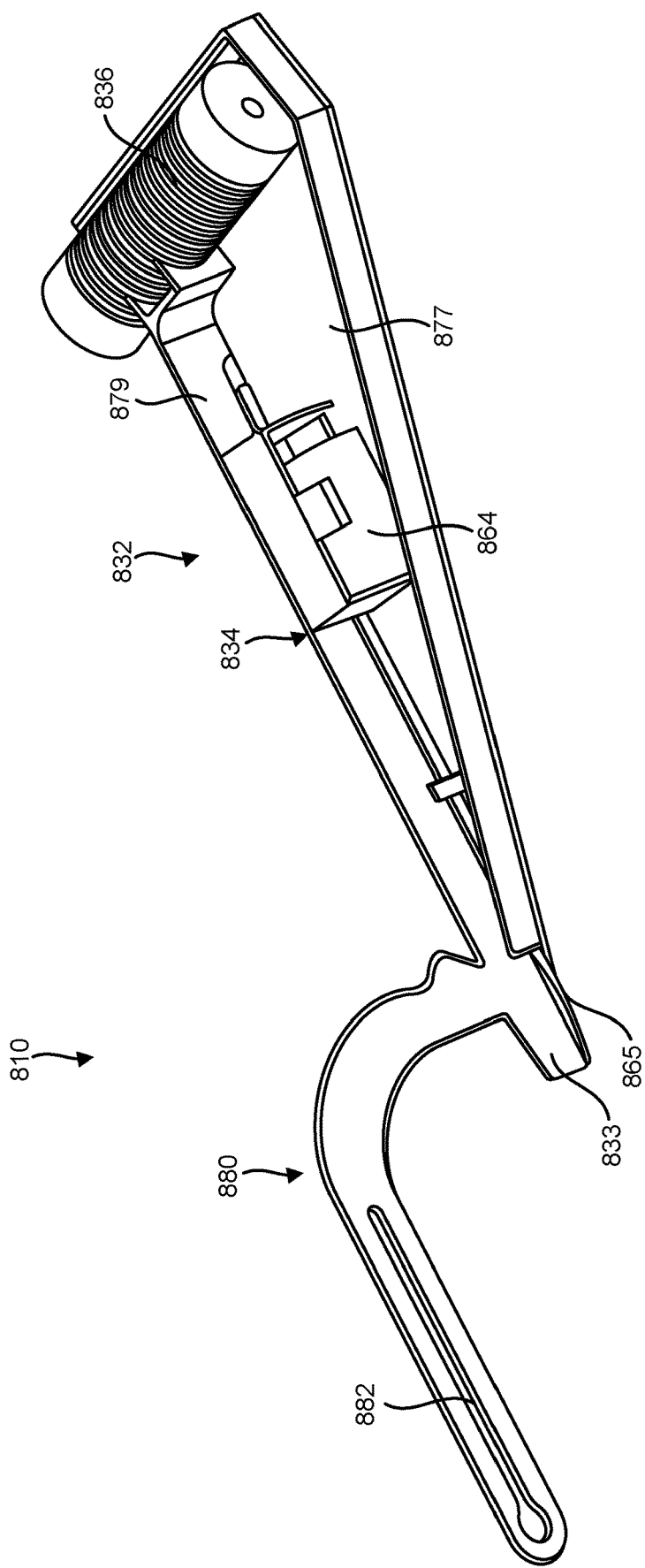
FIG. 47 illustrates an elevational perspective view of the laser device of FIG. 42 with a portion of the housing thereof removed.
Figure 48:
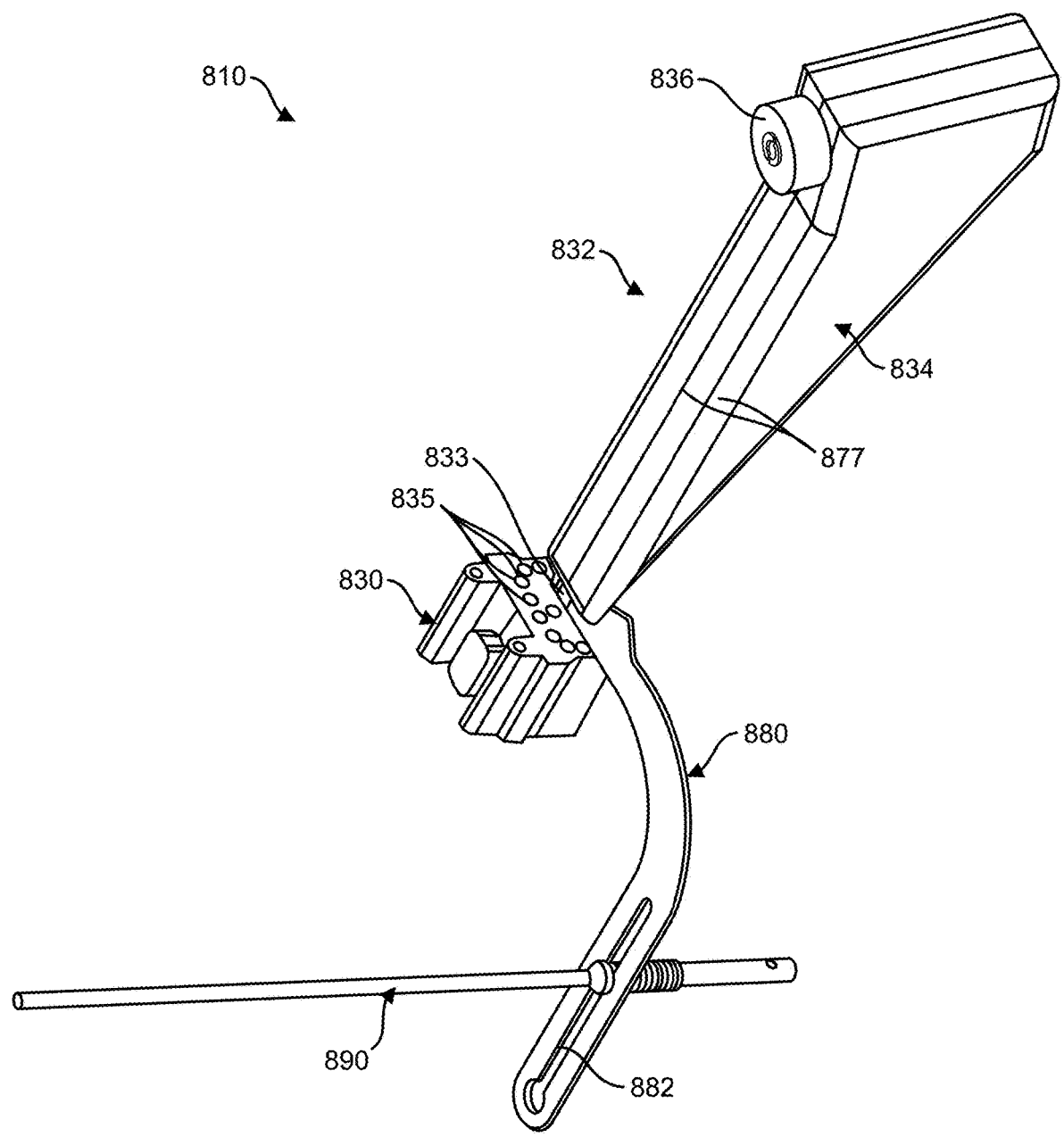
FIG. 48 illustrates an elevational perspective view of the laser device of FIG. 42 engaged with the guide block of FIG. 27.
Figure 49:
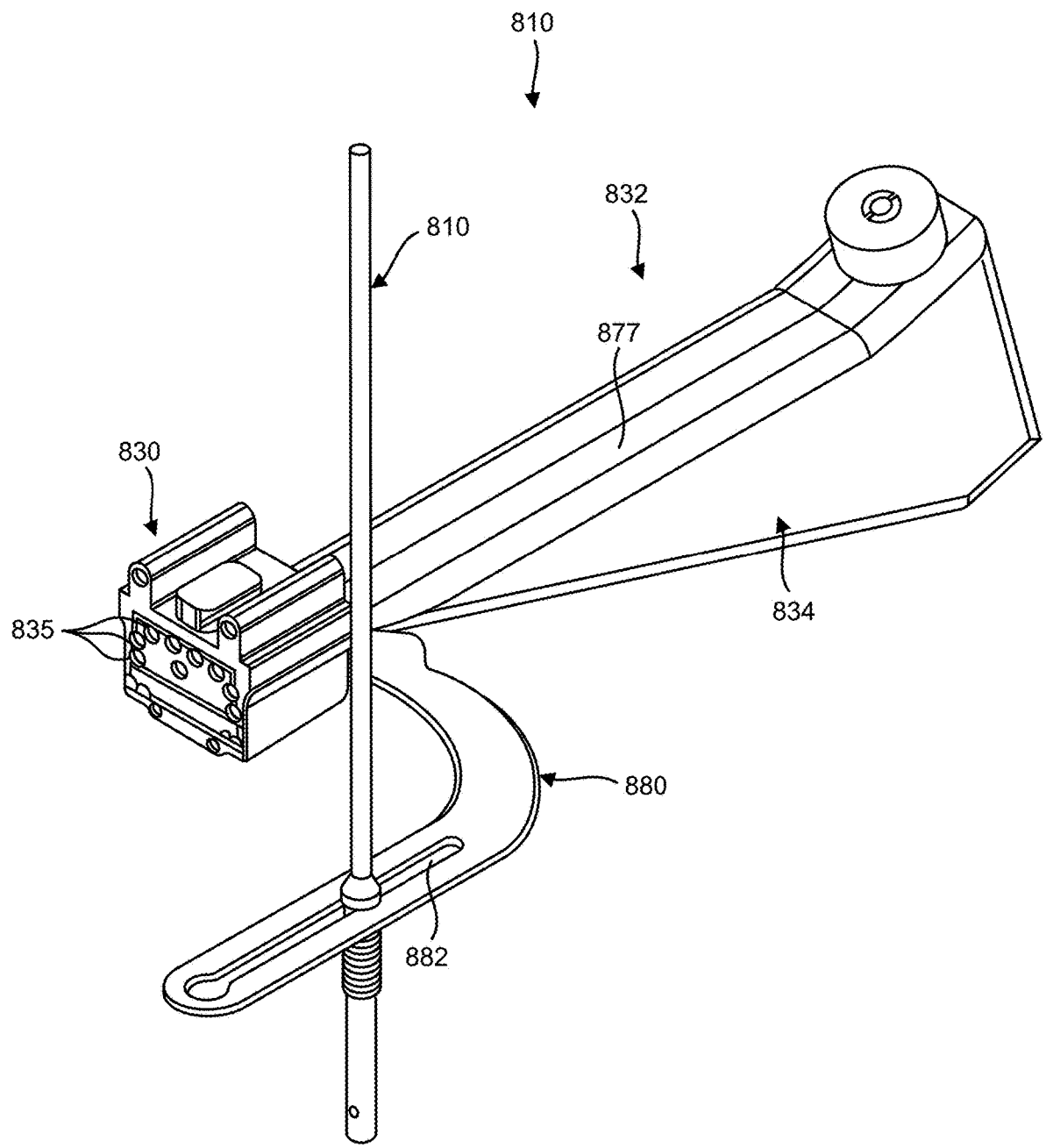
FIG. 49 illustrates a perspective view of the laser device of FIG. 42 engaged with the guide block of FIG. 27.
Figure 50:
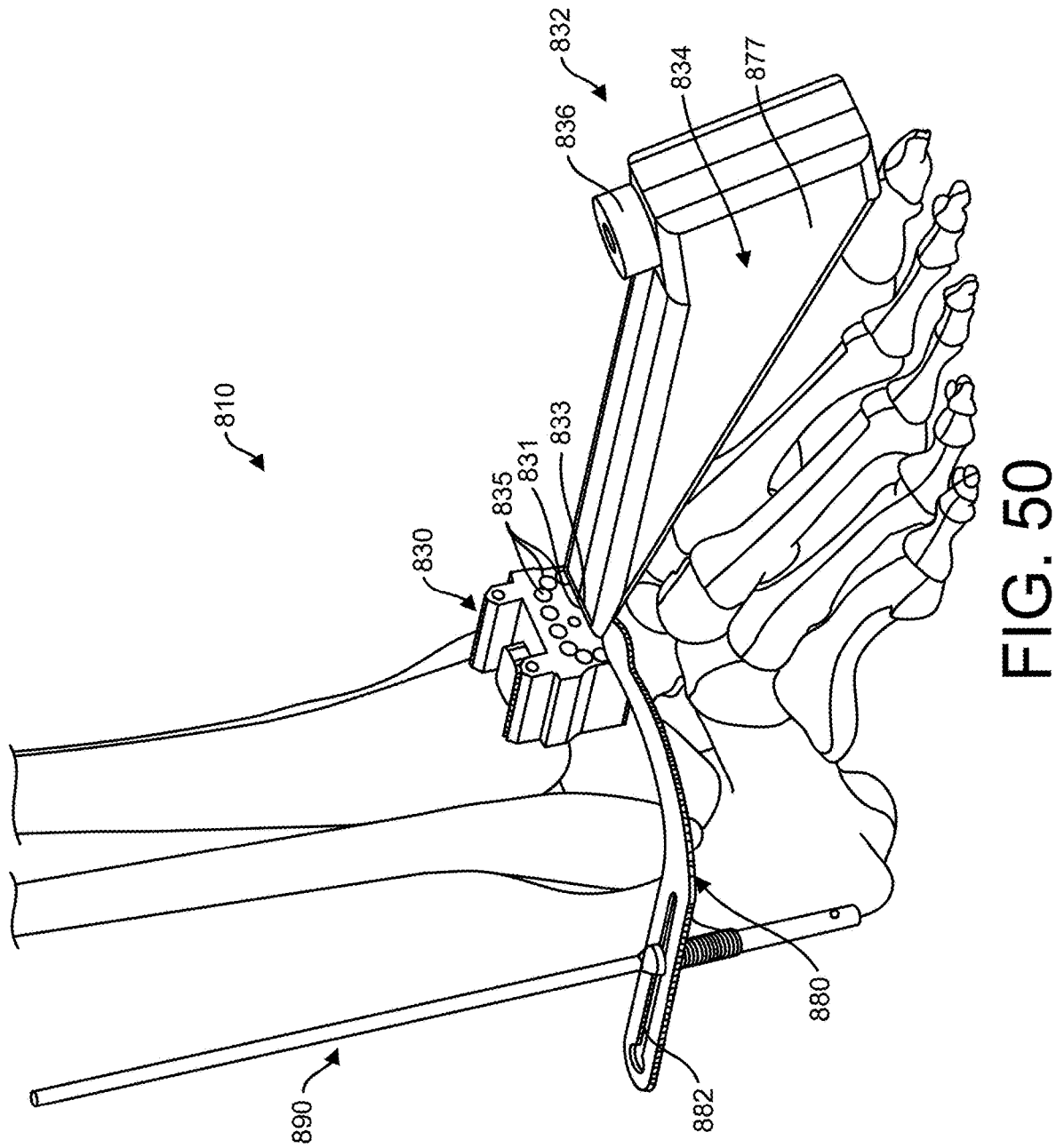
FIG. 50 illustrates an elevational perspective view of the laser device of FIG. 42 engaged with the guide block of FIG. 27 with respect to an ankle joint.
Figure 51:
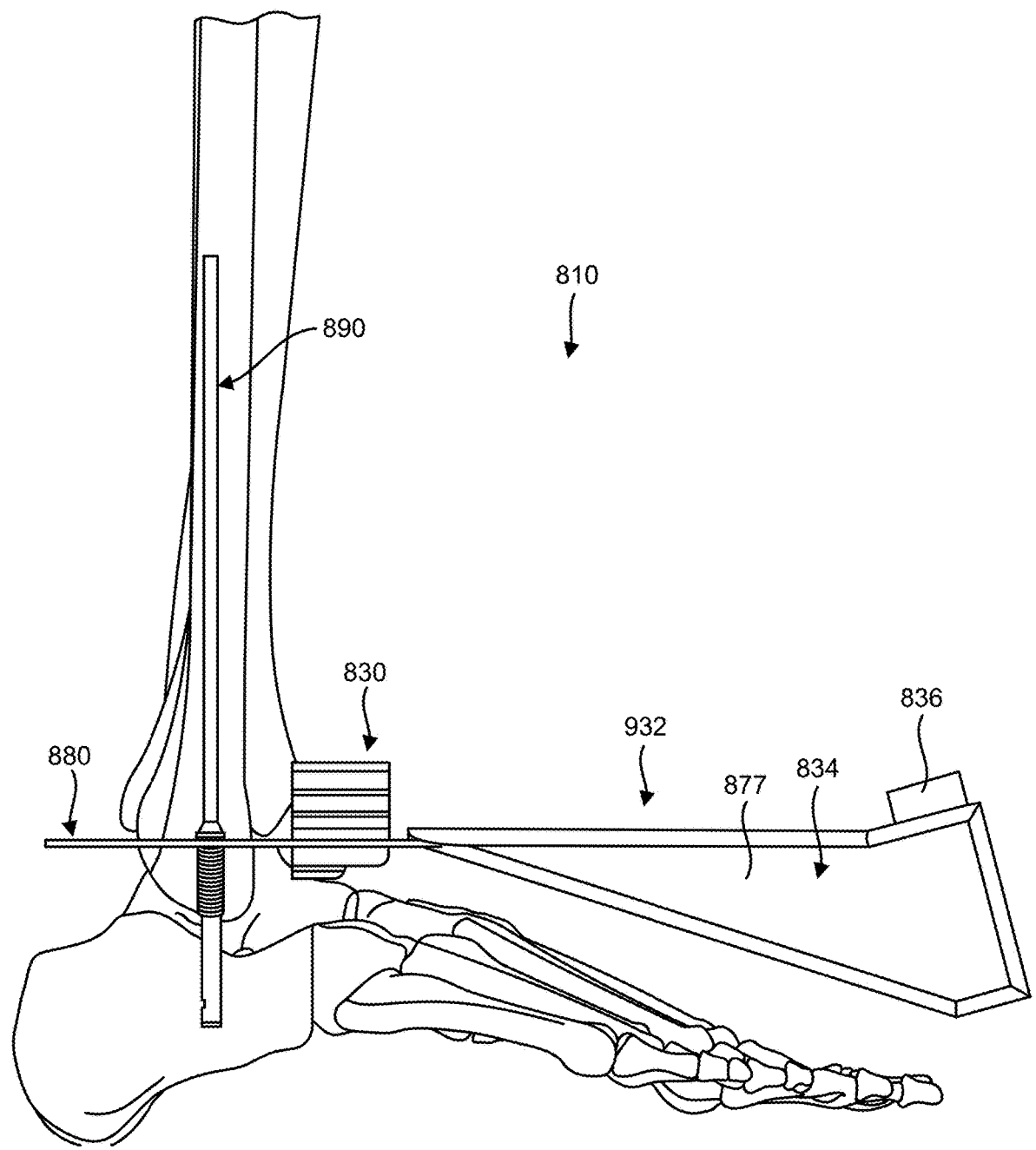
FIG. 51 illustrates a side view of the laser device of FIG. 42 engaged with the guide block of FIG. 27 with respect to an ankle joint.
Figure 52:
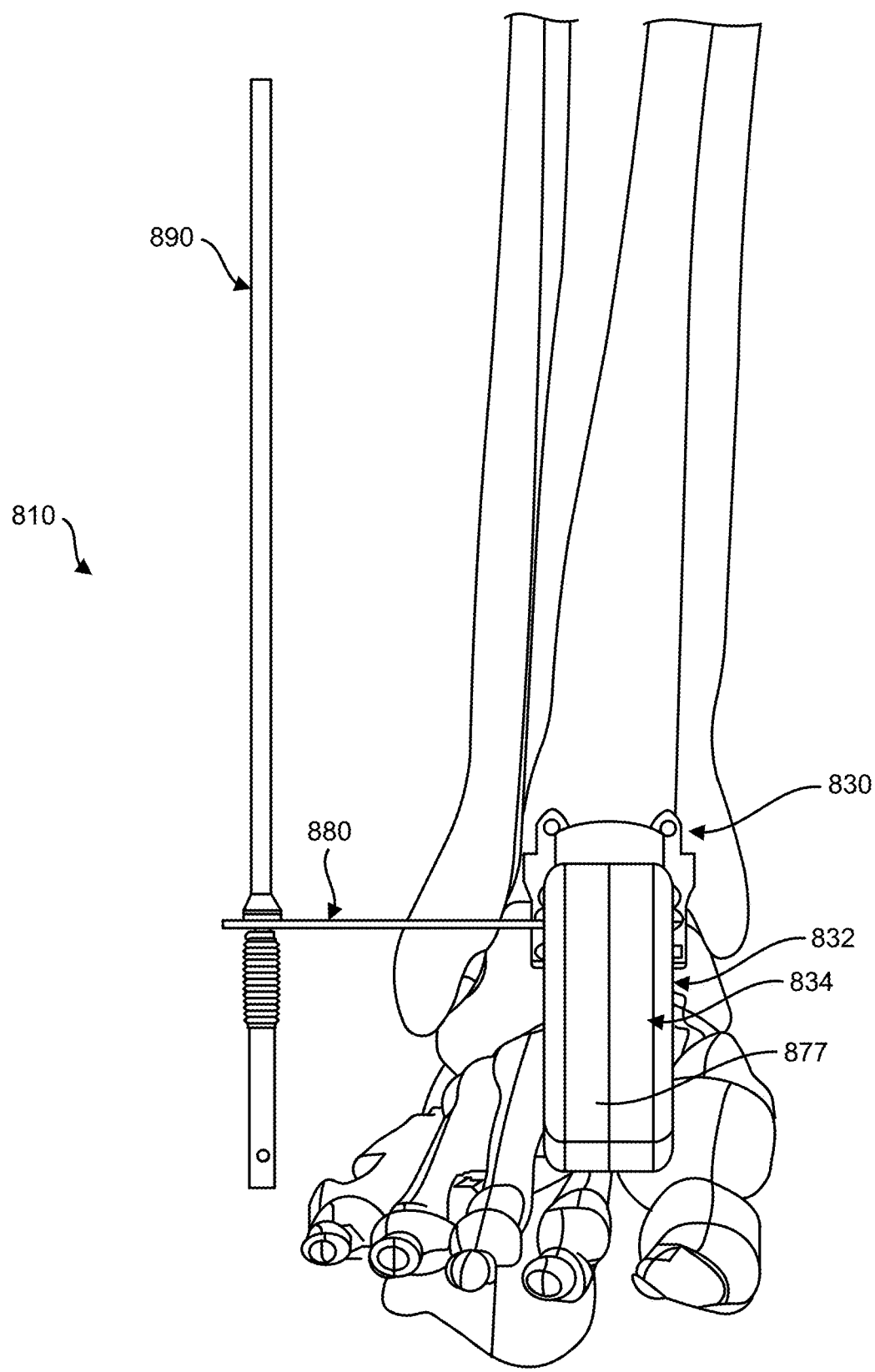
FIG. 52 illustrates a front view of the laser device of FIG. 42 engaged with the guide block of FIG. 27 with respect to an ankle joint.

As shown in FIGS. 46 and 47, the housing 834 of the implant alignment and guide system 810 comprises a structural support member or portion 879 that extends from the tang portion 833 to the laser generating and/or projecting device 836. The structural support member 879 may be fixedly coupled to or integral with the tang portion 833. The structural support member 879 may be fixedly coupled to the tang portion 833 of the laser generating and/or projecting device 836. The housing 834 may also include at least one outer cover or casing 877 that extends, at least partially, about the structural support member 879, the laser generating and/or projecting device 836, the power source 864 and/or other related components of the laser device portion 832. In some embodiments, the outer casing 877 may be removable from the laser device portion 832 such that the structural support member 879, the laser generating and/or projecting device 836, the power source 864 and/or other related components of the laser device portion 832 are exposed. In some embodiments, the outer casing 877 may be flexible, such as being formed from silicone, rubber or another flexible material.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features. Any examples of parameters are not exclusive of other parameters of the disclosed embodiments.

As used herein, the terms "comprising," "has," "including," "containing," and other grammatical variants thereof encompass the terms "consisting of" and "consisting essentially of." The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments.

Components, aspects, features, configurations, arrangements, uses and the like described, illustrated or otherwise disclosed herein with respect to any particular embodiment may be similarly applied to any other embodiment disclosed herein. Accordingly, the inventions are not to be seen as limited by the foregoing description, but is only limited by the scope of the appended claims.

This written description uses examples to disclose the inventions, including the best mode, and also to enable any person skilled in the art to practice the inventions, including making and using any devices or systems and performing any incorporated methods. The patentable scope of the inventions are defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An implant alignment and resection guide system, comprising: a target base configured to couple to the exterior of a patient in a first location that is in substantial alignment with an alignment axis associated with an anatomical structure of interest of a patient; a target member configured to couple to the target member, comprising a visual indication of the location of the alignment axis; a laser device configured to project a laser light; and an implant guide configured to couple to the patient proximate to the anatomical structure of interest and couple with the laser device, wherein the implant guide comprises a resection guide configured to resect at least one portion of the anatomical structure of interest, wherein the implant guide is configured such that when the laser line is substantially aligned with the visual indication of the target member, resection of the anatomical structure of interest via the resection guide facilities implantation of an implant in the resected anatomical structure of interest such that the implant is in alignment with the alignment axis, wherein the implant guide comprises a guide block that comprises a slot and the resection guide, the resection guide comprising at least one resection guide aperture configured to resect a portion of the anatomical structure of interest, wherein the laser device comprises a tang configured to removably mate within the slot of the guide block to removably couple the laser device and the guide block together.

2. The system of claim 1, further comprising a sterility barrier configured to extend over the patient and the target base, and wherein the target base and the target member are configured to couple such that the sterility barrier is positioned therebetween.

3. The system of claim 1, wherein the implant guide is configured such that when the laser line is substantially aligned with the visual indication of the target member, resection of the anatomical structure of interest via the resection guide facilities placement of the implant such that at least one outer engagement surface of the implant that engages with a bone and/or tissue of the anatomical structure of interest is substantially centered along the alignment axis.

4. The system of claim 1, wherein the implant guide is configured to adjust the laser device and the resection guide along at least one of a medial-lateral direction and a *varus*-valgus direction such that the laser line is substantially aligned with the visual indication of the target member.

5. The system of claim 1, wherein the implant guide is further configured to adjust at least one of the position and the orientation of the laser device and the resection guide with respect to the anatomical structure of interest and the visual indication of the target member.

6. The system of claim 1, wherein the target base comprises a radiopaque portion that facilitates alignment of the target base along the alignment axis.

7. The system of claim 1, wherein the laser device is configured to project a fan shaped laser light plane such that the laser light forms a substantially linear line.

8. The system of claim 1, wherein the laser device is removably coupled with the implant guide.

9. The system of claim 1, wherein at least one of the laser device and the resection guide are configured to removably couple with the implant guide.

10. The system of claim 1, wherein the tang comprises a switch configured to energize the laser device from an energy storage device of the laser device such that the laser device projects the laser light therefrom in an activated state thereof and deenergizes the laser device such it does not project the laser light therefrom in a deactivated state thereof, and wherein the tang and the slot are configured such that the switch is moved into the activated state from the deactivated state when the tang is seated within the slot.

11. The system of claim 1, further comprising a planar wing member configured to removably couple with the slot of the guide block, the wing member being elongated along a pathway that extends in a first direction and a second direction.

12. The system of claim 11, wherein the wing member comprises a second tang configured to removably mate within the slot of the guide block to removably couple the wing member and the guide block together.

13. The system of claim 11, wherein the wing member extends from the tang of the laser device to removably couple the laser device and the wing member and the guide block together.

14. The system of claim 11, further comprising an elongate alignment rod configured to engage with the planar wing member in a normal orientation.

15. The system of claim 1, wherein the guide block and the laser device are configured such that when the laser device and the guide block are coupled together, the laser device projects a laser light line that is aligned with a center of the resected portion of the anatomical structure of interest.

16. The system of claim 1, wherein the resected portion of the anatomical structure of interest is configured to engage with an implant, and wherein the guide block and the laser device are configured such that when the laser device and the guide block are coupled together, the laser device projects a laser light line that is aligned with a center of the implant when the implant is mated with the resected portion of the anatomical structure of interest.

17. The system of claim 1, wherein the implant guide is further configured to adjust at least one of the position and the orientation of the laser device and the resection guide with respect to the anatomical structure of interest and the visual indication of the target member.

18. The system of claim 1, wherein the guide block comprises a radiolucent material, and wherein the guide block comprises a plurality of radiopaque guide members that identify at least one of an outer edge, position and orientation of the resected portion of the anatomical structure of interest.

19. The system of claim 18, wherein the alignment guide further comprises adjustment components configured to adjust at least one of the position and the orientation of the laser device and the guide block when the laser device and the guide block are coupled together along a plurality of degrees of freedom.

20. The system of claim 18, wherein the alignment guide further comprises adjustment components configured to adjust at least one of the position and the orientation of the laser device and the guide block when the laser device and the guide block are coupled together along a medial-lateral direction and a varus-valgus direction.

21. The system of claim 1, wherein the implant is an ankle joint implant, and wherein the alignment guide is configured such that when the laser line is substantially aligned with the visual indicator of the target member, resection of a distal tibia and/or talus of an ankle of the patient's leg via the resection guide facilities positioning of the implant therein along a mechanical axis of the patient's leg.

22. The system of claim 1, further comprising a reference member configured to couple to the patient such that the laser light projects thereon, and wherein the reference member includes a plurality of visual indications as reference points to at least one of the position and orientation of the laser light.

23. The system of claim 1, wherein the alignment axis is a mechanical axis or an anatomical axis of the anatomical structure of interest.

\* \* \* \* \*

UNITED STATES PATENT AND TRADEMARK OFFICE
CERTIFICATE OF CORRECTION

PATENT NO. : 11,389,253 B2
APPLICATION NO. : 17/084155
DATED : July 19, 2022
INVENTOR(S) : Barmes et al.

It is certified that error appears in the above-identified patent and that said Letters Patent is hereby corrected as shown below:

In the Claims

Column 38, Line 49: Claim 1, Delete "a target member configured to couple to the target member" and insert -- a target member configured to couple to the target base --

Signed and Sealed this
Twenty-eighth Day of March, 2023

Katherine Kelly Vidal
Director of the United States Patent and Trademark Office